United States Patent [19]

Smith

[11] 4,104,474

[45] Aug. 1, 1978

[54] 5-OXA-13,14-DIDEHYDRO-11-DEOXY-17-PHENYL-18,19,20-TRINOR-PGF$_{1\alpha}$ COMPOUNDS

[75] Inventor: Herman W. Smith, Kalamazoo, Mich.

[73] Assignee: The Upjohn Company, Kalamazoo, Mich.

[21] Appl. No.: 821,008

[22] Filed: Aug. 1, 1977

Related U.S. Application Data

[62] Division of Ser. No. 657,740, Feb. 13, 1976.

[51] Int. Cl.$^2$ .............................. C07C 177/00
[52] U.S. Cl. ..................... 560/53; 560/121; 260/514 D; 260/520 R; 260/520 B
[58] Field of Search ........... 560/53; 260/520 R, 520 B

[56] References Cited

PUBLICATIONS

Derwent Abstract 47293U-B DT.-2305044-Q (09-08-73).
Derwent Abst. 18176y/11 BE-846-080 (10-3-77).
Derwent Abst. 6189x/33, DT 2603-172 (5-8-76).
Derwent Abst. 59715x/32, BE 839-533 (1-7-76).
Derwent Atst. 79219x/42, U.S. 3984400 (5-10-76).

*Primary Examiner*—Paul J. Killos
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

73 Claims, No Drawings

5-OXA-13,14-DIDEHYDRO-11-DEOXY-17-PHENYL-18,19,20-TRINOR-PGF$_{1\alpha}$ COMPOUNDS This is a division, of application Ser. No. 657,740, filed Feb. 13, 1976.

BACKGROUND OF THE INVENTION

This invention provides novel compositions of matter. This invention further provides novel processes for producing these compositions of matter. This invention further provides novel chemical intermediates useful in the above processes.

Particularly this invention provides novel analogs of some of the known prostaglandins which differ from corresponding known prostaglandins in that these prostaglandin analogs have a triple bond between C-13 and C-14, that is the C-13 to C-14 moiety is —C≡C—.

The known prostaglandins include the PGE compounds, e.g. prostaglandin E$_1$ (PGE$_1$), prostaglandin E$_2$ (PGE$_2$), prostaglandin E$_3$ (PGE$_3$), and dihydroprostaglandin E$_1$ (dihydro-PGE$_1$).

The known prostaglandins include PGF$_\alpha$ compounds, e.g. prostaglandin F$_{1\alpha}$ (PGF$_{1\alpha}$), prostaglandin F$_{2\alpha}$ (PGF$_{2\alpha}$), prostaglandin F$_{3\alpha}$ (PGF$_{3\alpha}$), and dihydroprostaglandin F$_{1\alpha}$ (dihydro-PGF$_{1\alpha}$).

The known prostaglandins include PGF$_\beta$ compounds, e.g. prostaglandin F$_{1\beta}$ (PGF$_{1\beta}$), prostaglandin F$_{2\beta}$ (PGF$_{2\beta}$), prostaglandin F$_{3\beta}$ (PGF$_{3\beta}$), and dihydroprostaglandin F$_{1\beta}$ (dihydro-PFG$_{1\beta}$).

The known prostaglandins include PGA compounds, e.g. prostaglandin A$_1$ (PGA$_1$), prostaglandin A$_2$ (PGA$_2$), prostaglandin A$_3$ (PGA$_3$), and dihydroprostaglandin A$_1$ (dihydro-PGA$_1$).

The known prostaglandins include PGB compounds, e.g. prostaglandin B$_1$ (PGB$_1$), prostaglandin B$_2$ (PGB$_2$), prostaglandin B$_3$ (PGB$_3$), and dihydroprostaglandin B$_1$ (dihydro-PGB$_1$).

Each of the above mentioned known prostaglandins (PG's) is a derivative of prostanoic acid which has the following structure and carbon atom numbering

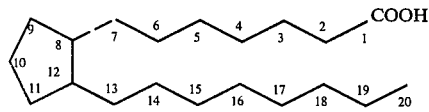

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_1$ has the following structure:

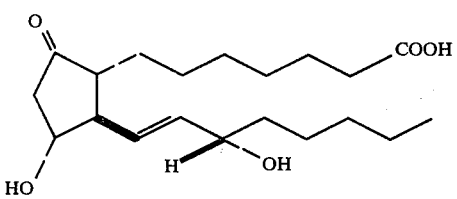

PGE$_2$ has the following structure:

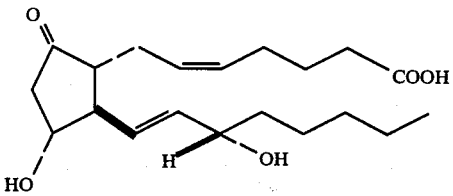

PGE$_3$ has the following structure:

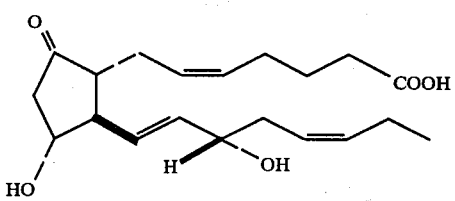

Dihydro-PGE$_1$ has the following structure:

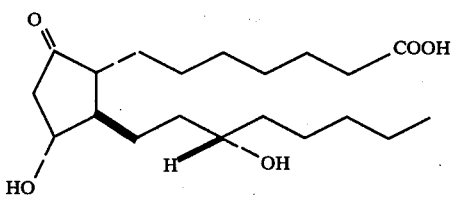

PGF$_{1\alpha}$ has the following structure:

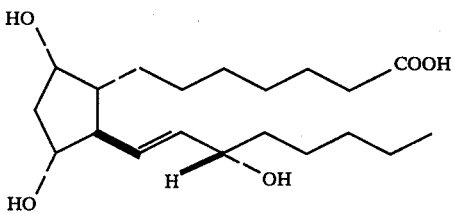

PGF$_{2\alpha}$ has the following structure:

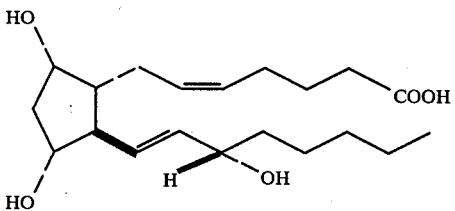

PGF$_{3\alpha}$ has the following structure:

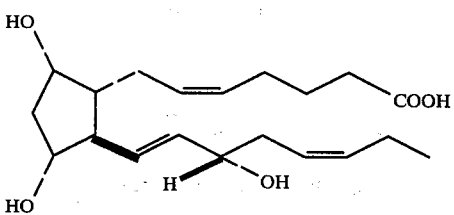

Dihydro-PGF$_{1\alpha}$ has the following structure:

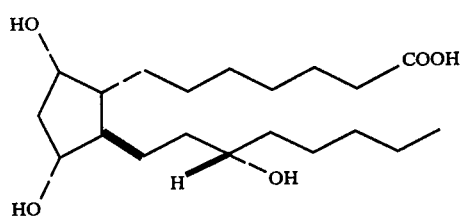

PGF$_{1\beta}$ has the following structure:

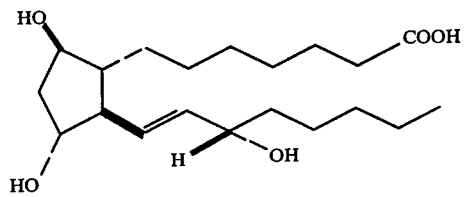

PGF$_{2\beta}$ has the following structure:

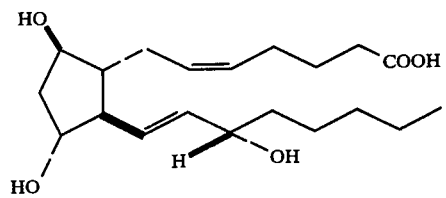

PGF$_{3\beta}$ has the following structure:

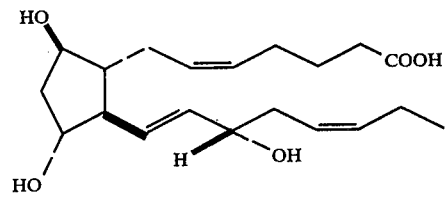

Dihydro-PGF$_{1\beta}$ has the following structure:

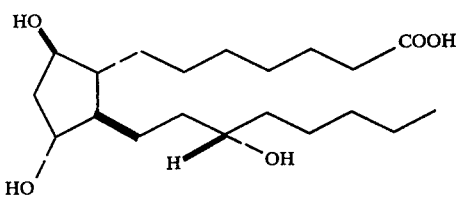

PGA$_1$ has the following structure:

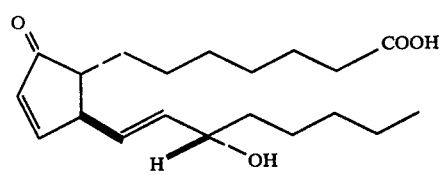

PGA$_2$ has the following structure:

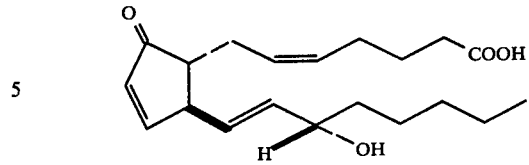

PGA$_3$ has the following structure:

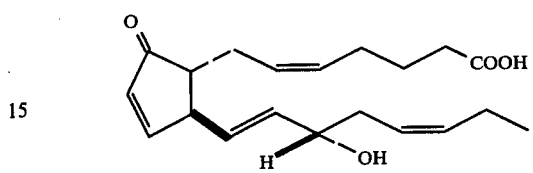

Dihydro-PGA$_1$ has the following structure:

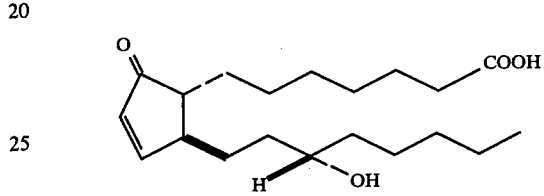

PGB$_1$ has the following structure:

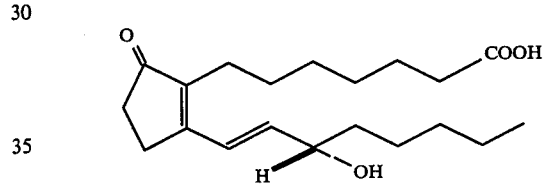

PGB$_2$ has the following structure:

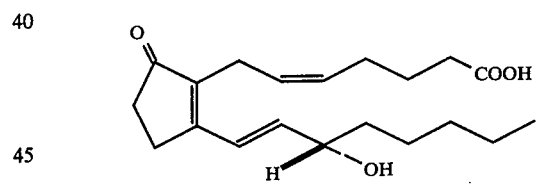

PGB$_3$ has the following structure:

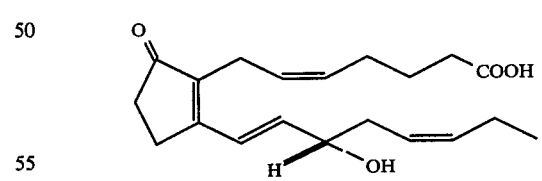

Dihydro-PGB$_1$ has the following structure:

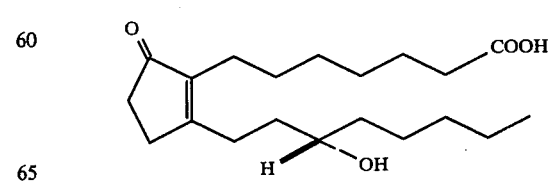

In the above formulas, as well as in the formulas hereinafter given, broken line attachments to the cyclopentane ring indicate substituents in alpha configuration i.e., below the plane of the cyclopentane ring. Heavy solid line attachments to the cyclopentane ring indicate substituents in beta configuration, i.e., above the plane of the cyclopentane ring. The use of wavy lines ($\sim$) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins. Expressions such as C-13, C-14, C-15, and the like, refer to the carbon atom in the prostaglandin analog which is in the position corresponding to the position of the same number in prostanoic acid.

Molecules of the known prostaglandins each have several centers of asymmetry, and can exist in racemic (optically inactive) form and in either of the two enantiomeric (optically active) forms, i.e. the dextrorotatory and levorotatory forms. As drawn, the above formulas each represent the particular optically active form of the prostaglandin as is obtained from mammalian tissues, for example, sheep vesicular glands, swine lung, or human seminal plasma, from carbonyl and/or double bond reduction of the prostaglandin so obtained. See, for example, Bergstrom et al., cited above. The mirror image of each of these formulas represents the other enantiomer of that prostaglandin. The racemic form of a prostaglandin contains equal numbers of both enantiomeric molecules, and one of the above formulas and the mirror image of that formula is needed to represent correctly the corresponding racemic prostaglandin. For convenience hereinafter, use of the term, prostaglandin or "PG" will mean the optically active form of that prostaglandin thereby referred to with the same absolute configuration as $PGE_1$ obtained from mammalian tissues. When reference to the racemic form of one of those prostaglandins is intended, the word "racemic" or "dl" will precede the prostaglandin name.

The term "prostaglandin-type" (PG-type) product, as used herein, refers to any cyclopentane derivative which is useful for at least one of the same pharmacological purposes as the prostaglandins, as indicated herein.

The term prostaglandin-type intermediate, as used herein, refers to any cyclopentane derivative useful in preparing a prostaglandin-type product.

The formulas, as drawn herein, which depict a prostaglandin-type product or an intermediate useful in preparing a prostaglandin-type product, each represent the particular stereoisomer of the prostaglandin-type product which is of the same relative stereochemical configuration as a corresponding prostaglandin obtained from mammalian tissues, or the particular stereoisomer of the intermediate which is useful in preparing the above stereoisomer of the prostaglandin-type product.

The term "prostaglandin analog", as used herein, represents that stereoisomer of a prostaglandin-type product which is of the same relative stereochemical configuration as a corresponding prostaglandin obtained from mammalian tissues or a mixture comprising that stereoisomer and the enantiomer thereof. In particular, where a formula is used to depict a prostaglandin-type compound herein, the term prostaglandin analog refers to the compound of that formula, or a mixture comprising that compound and the enantiomer thereof.

The various PG's named above, their esters, acylates and pharmacologically acceptable salts, are extremely potent in causing various biological responses. For that reason, these compounds are useful for pharmacological purposes. See, for example, Bergstrom et al., Pharmacol. Rev. 20, 1 (1968) and references cited therein.

For the PGE compounds these biological responses include:

(a) decreasing blood pressure (as measured, for example, in anesthetized, pentolinium-treated rats);

(b) stimulating smooth muscle (as shown be tests, for example, on guinea pig ileum, rabbit duodenum, or gerbil colon);

(c) effecting lipolytic activity (as shown by antagonism of epinephrine induced release of glycerol from isolated rat fat pads);

(d) inhibiting gastric secretion and reducing undesirable gastrointestinal effects from systematic administration of prostaglandin synthetase inhibitors;

(e) controlling spasm and facilitating breathing in asthmatic conditions;

(f) decongesting nasal passages;

(g) decreasing blood platelet adhesion (as shown by platelet to glass adhesiveness) and inhibiting blood platelet aggregation and thrombus formation induced by various physical stimuli (e.g., arterial injury) or chemical stimuli (e.g., ATP, ADP, serotinin, thrombin, and collagen);

(h) affecting the reproductive organs of mammals as labor inducers, abortifacients, cervical dilators, regulators of the estrus, and regulators of the menstrual cycle; and (j) accelerating growth of epidermal cells and keratin in animals.

For the $PGF_\alpha$ compound these biological responses include:

(a) increasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organs of mammals as labor inducers, abortifacients, cervical dilators, regulators of the estrus, and regulators of the menstral cycle.

For the $PGF_\beta$ compounds these biological responses include:

(a) decreasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages;

(f) decreasing blood platelet adhesion (as shown by platelet to glass adhesiveness) and inhibiting blood platelet aggregation and thrombus formation induced by various physical stimuli (e.g., arterial injury) or chemical stimuli (e.g., ADP, ATP, serotinin, thrombin, and collagen); and (g) affecting the reproductive organs of mammals as labor inducers, abortifacients, cervical dilators, regulators of the estrus, and regulators of the menstrual cycle.

For the PGA compounds these biological responses include:

(a) decreasing blood pressure (as measured, for example, in anesthetized, pentolinium-treated rats);

(b) stimulating smooth muscle (as shown by tests on guinea pig ileum, rabbit duodenum, or gerbil colon);

(c) inhibiting gastric secretion and reducing undesirable gastrointestinal effects from systematic administration of prostaglandin synthetase inhibitors;

(d) controlling spasm and facilitating breathing in asthmatic conditions;

(e) decongesting nasal passages; and (f) increasing kidney blood flow.

For the PGB compounds these biological responses include:

(a) stimulating smooth muscle (as shown by tests on guinea pig ileum, rabbit duodenum, or gerbil colon); and (b) accelerating growth of epidermal cells and keratin in animals.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

The prostaglandins so cited above as hypotensive agents are useful to reduce blood pressure in mammals, including man. For this purpose, the compounds are administered by intravenous infusion at the rate about 0.01 to about 50 $\mu$g. per kg. of body weight per minute or in single or multiple doses of about 25 to 500 $\mu$g. per kg. of body weight total per day.

The PGF$_\alpha$ compounds are useful in increasing blood pressure in mammals, including man. Accordingly, these compounds are useful in the treatment of shock (hemorrhagic shock, endotoxin shock, cardiogenic shock, surgical shock, or toxic shock). Shock is marked by pallor and clamminess of the skin, decreased blood pressure, feeble and rapid pulse, decreased respiration, restlessness, anxiety, and sometimes unconsciousness. Shock usually follows cases of injury and trauma. Expert and fast emergency measures are required to successfully manage such shock conditions. Accordingly, prostaglandins, combined with a pharmaceutical carrier which adapts the prostaglandin for intramuscular, intravenous, or subcutaneous use, are useful, especially in the early stages of shock where the need to increase blood pressure is a critical problem, for aiding and maintaining adequate blood flow, perfusing the vital organs, and exerting a pressor response by constricting veins and raising blood pressure to normal levels. Accordingly, these prostaglandins are useful in preventing irreversible shock which is characterized by a profound fall in blood pressure, dilation of veins, and venus blood pooling. In the treatment of shock, the prostaglandin is infused at a dose of 0.1 – 25 mcg./kg./min. The prostaglandin may advantageously be combined with known vasoconstrictors; such as phenoxy-benzamine, norepinephrine, and the like. Further, when used in the treatment of shock the prostaglandin is advantageously combined with steroids (such as, hydrocortisone or methylprednisolone), tranquilizers, and antibiotics (such as, lincomycin or clindamycin).

The compounds so cited above as extremely potent in causing stimulation of smooth muscle are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the prostaglandin is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection of infusion during puerperium in the range 0.01 to 2 mg. per kg. of body weight per day, the exact dose depending on the age, weight, and condition of the patient or animal.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular disease, and hyperthyroidism.

The prostaglandins so cited above as useful in mammals, including man and certain useful animals, e.g., dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the prostaglandin and the antiinflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including PGE$_1$, PGE$_2$, PGE$_3$, 13,14-dihydro-PGE$_1$, and the corresponding 11-deoxy-PGE and PGA compounds. Prostaglandins are useful, for example, in reducing the undesirable gastrointestinal effects resulting from systemic administration of indomethacin, phenylbutazone, and aspirin. These are substances specifically mentioned in Partridge et al. as non-steroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

The prostaglandin is administered along with the anti-inflammatory prostaglandin synthetase inhibitor either by the same route of administration or by a different route. For example, if the anti-inflammatory substance is being administered orally, the prostaglandin is also administered orally or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostaglandin is also administered rectally. Further, the prostaglandin can be conveniently administered orally or, in the case of women, vaginally. It is especially convenient when the administration route is to be the same for both anti-inflammatory substance and prostaglandin, to combine both into a single dosage form.

The dosage regimen for the prostaglandin in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular individual mammal to the particular synthetase inhibitor with regard to gastrointestinal effects, and the particular prostaglandin to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the prostaglandin to reduce and then substantially to eliminate those undesirable effects.

The prostaglandins so cited above as useful in the treatment of asthma, are useful, for example, as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone). Regarding use of these compounds see M. E. Rosenthale, et al., U.S. Pat. No. 3,644,638.

The prostaglandins so cited above as useful in mammals, including man, as nasal decongestants are used for this purpose, in a dose range of about 10 $\mu$g. to about 10 mg. per ml. of a pharmacologically suitable liquid vehicle or as an aerosol spray, both for topical application.

The prostaglandins so cited above are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to the lipemia, and other clinial conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

The prostaglandins so cited above as useful in place of oxytocin to induce labor are used in pregnant female animals including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks postmature and natural labor has not started, or 12 to 60 hours after the membranes have ruptured and natural labor has not yet started. An alternative route of administration is oral.

These compounds are further useful for controlling the reproductive cycle in menstruating female mammals, including humans. By the term menstruating female mammals is meant animals which are mature enough to menstruate, but no so old that regular menstruation has ceased. For that purpose the prostaglandin is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the prostaglandin is administered locally or systemically.

The prostaglandin, for example, is administered orally or vaginally at doses of about 5 to 50 mg. per treatment of an adult female human, with from one to five treatments per 24 hour period. Alternatively the prostaglandin is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostaglandin is injected or applied in a feed at doses of 0.1–100 mg. per animal and may be combined with other agents such as steroids. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

The PGA compounds and derivatives and salts thereof increase the flow of blood in the mammalian kidney, thereby increasing volume and electrolyte content of the urine. For that reason, PGA compounds are useful in managing cases of renal dysfunction, especially those involving blockage of the renal vascular bed. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

The compounds so cited above as promoters and accelerators of growth of epidermal cells and keratin are useful in animals, incuding humans, useful domestic animals, pets, zoological specimens, and laboratory animals for this purpose. For this reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For the above purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqueous solution containing 1 to 500 $\mu$g. per ml. of the prostaglandin. Especially for topical use, these prostaglandins are useful in combination with antibiotics, for example, gentamycin, neomycin, polymixin, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Certain $PG_2$-type compounds wherein the C-13 to C-14 moiety is —C≡C— are known in the art. For example, see Gandolfi C., et al., Il Farmaco, 27, 1125, wherein 13,14-didehydro-$PGF_{2\alpha}$ and 13,14-didehydro-$PGE_2$ and their 15-epimers are described. See futher, South African Pat. No. 73-2329, Derwent Farmdoc CPI 54179U, wherein 13,14-didehydro-$PGF_{2\alpha}$-, $PGF_{2\beta}$-, $PGE_2$-, and $PGA_2$-type compounds are disclosed with optional C-16 alkyl substitution and with optional oxa or thia substitution at the C-3 position. Further, the above South African Patent discloses the 8$\beta$,12$\alpha$-stereoisomer of the above-described compounds. See also J. Fried, et al., Tetrahedron Letters, 3899 (1963), which discloses 13,14-dihydro-$PGF_{2\alpha}$.

Additionally certain 13-didehydro-$PG_1$-type compounds are known in the prior art. See, for example, J. Fried, et al., Annals, of the New York Academy of Science 18, 38 (1971), which discloses 7-oxa-13,14-didehydro-$PGF_{1\alpha}$. See also R. Pappo, et al., Tetrahedron Letters, 2627, 2630 (1972), which discloses racemic 13,14-dihydro-11β-$PGE_1$; and R. Pappo, et al., Annals, of the New York Academy of Science 18, 64 (1971), which discloses 13,14-didehydro-11β-$PGB_1$. Finally, see the following patents which disclose 13,14-dihydro-$PGB_1$-type compounds: Belgian Pat. No. 777,022 (Derwent Farmdoc CPI 43791T) German Offenlegungsschrift No. 1,925,672 (Derwent Farmdoc CPI No. 41,084), and German Offenlegungsschrift No. 2,357,781 (Derwent Farmdoc No. 42046V).

SUMMARY OF THE INVENTION

This invention provides novel prostaglandin analogs, esters of these analogs, and pharmacologically acceptable salts of these analogs.

This invention further provides lower alkanoates of these analogs.

This invention further provides novel processes for preparing these analogs.

This invention further provides novel chemical intermediates useful in the preparation of these analogs.

The present invention discloses:

(1) a prostaglandin analog of the formula

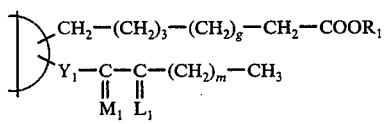

wherein D is

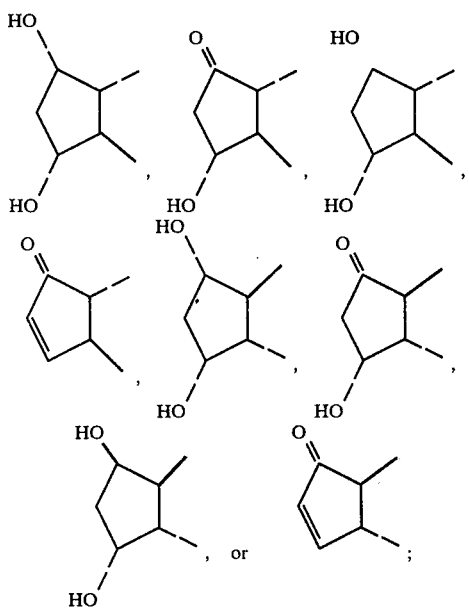

wherein $Y_1$ is —C≡C—;
wherein g is one, 2, or 3;
wherein m is one to 5, inclusive;
wherein $M_1$ is

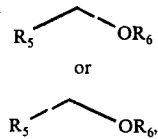

wherein $R_5$ and $R_6$ are hydrogen or methyl, with the proviso that one of $R_5$ and $R_6$ is methyl only when the other is hydrogen;

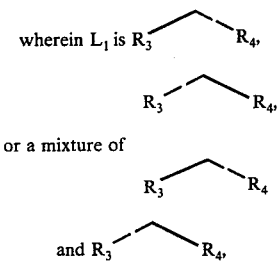

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation;

(2) a prostaglandin analog of the formula:

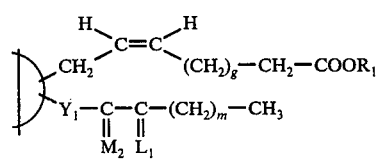

wherein D is

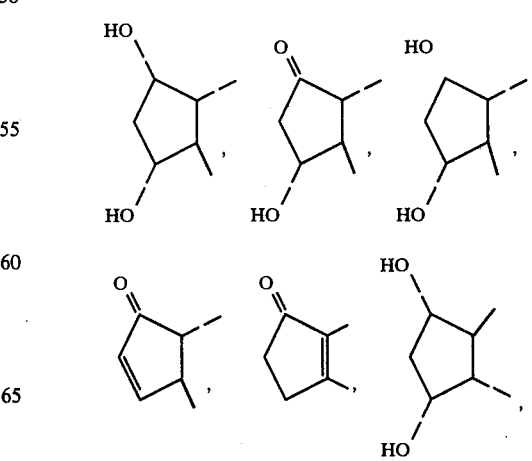

-continued

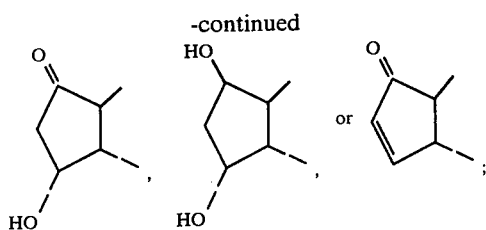

wherein $L_1$, $R_1$, $Y_1$, g, and m are as defined above; and wherein $M_2$ is

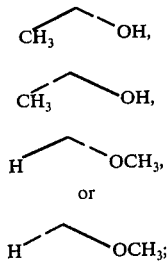

(3) a prostaglandin analog of the formula:

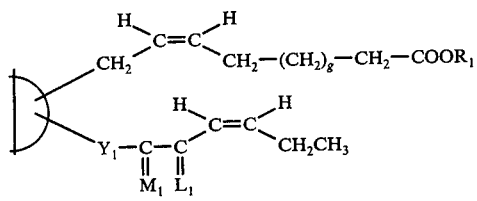

wherein D is

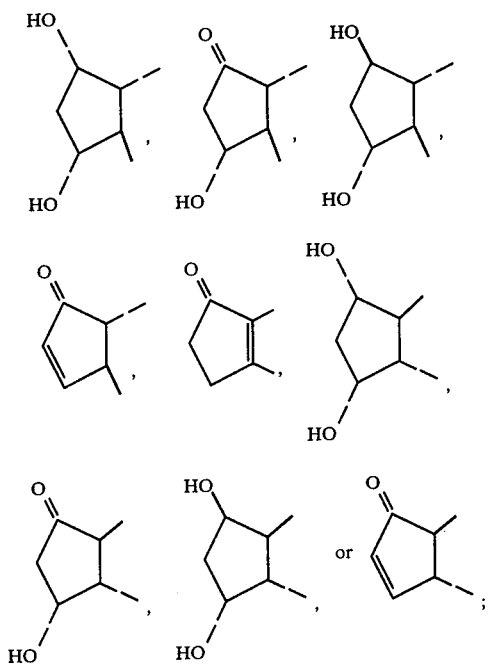

wherein $L_1$, $M_1$, $R_1$, $Y_1$, and g are as defined above;
(4) a prostaglandin analog of the formula

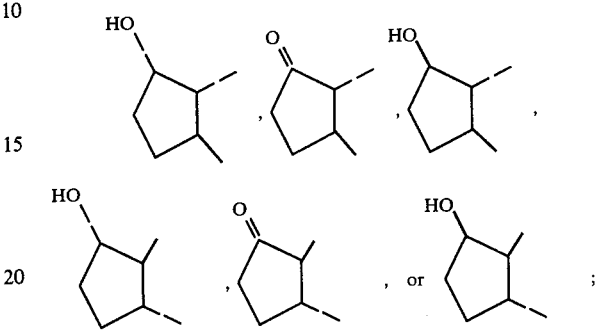

wherein D is wherein $L_1$, $M_1$, $R_1$, and $Y_1$ are as defined above;
wherein $Z_1$ is
(1) cis—CH=CH—CH$_2$—(CH$_2$)$_g$—CH$_2$—;
(2) cis—CH=CH—CH$_2$—(CH$_2$)$_g$—CF$_2$—;
(3) cis—CH$_2$—CH=CH—(CH$_2$)$_g$—CH$_2$—;
(4) —(CH$_2$)$_3$—(CH$_2$)$_g$—CH$_2$—;
(5) —(CH$_2$)$_3$—(CH$_2$)$_g$—CF$_2$—;
(6) —CH$_2$—O—CH$_2$—(CH$_2$)$_g$—CH$_2$—, (7) —(CH$_2$)$_2$—O—(CH$_2$)$_g$—CH$_2$—;
(8) —(CH$_2$)$_3$—O—(CH$_2$)$_g$—;

(9)

—⟨phenyl⟩—CH$_2$—(CH$_2$)$_g$—, or (10)

—⟨phenyl⟩—O—(CH$_2$)$_g$—, wherein g is as defined above;
wherein $R_7$ is
(1) —(CH$_2$)$_m$—CH$_3$, (2) —O—⟨phenyl⟩—(T)$_s$, (3) —CH$_2$—⟨phenyl⟩—(T)$_s$, or (4) cis—CH=CH—CH$_2$—CH$_3$,
wherein m is one to 5, inclusive, T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl, with the further proviso that $R_7$ is

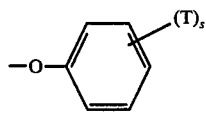

wherein T and s are as defined above, only when $R_3$ and $R_4$ are hydrogen or methyl, being the same or different; and (5) a prostaglandin analog of the formula

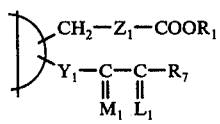

wherein D is

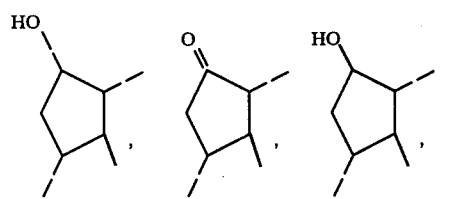

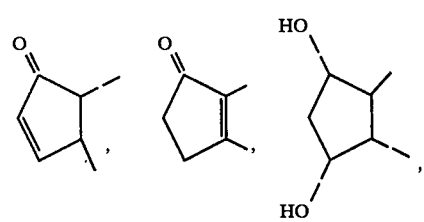

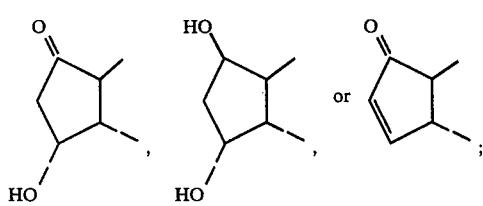

wherein $L_1$, $M_1$, $R_1$, $R_7$, $Y_1$, and $Z_1$ are as defined above; with the proviso that $Z_1$ is cis—CH=CH—CH$_2$—(CH$_2$)$_g$—CH$_2$— or —(CH$_2$)$_3$—(CH$_2$)$_g$—CH$_2$—; only when $R_7$ is

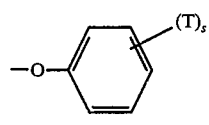

or

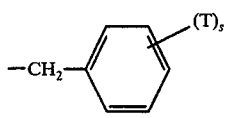

where T and s are as defined above.

Within the scope of the novel prostaglandin analogs of this invention, there are represented above:

(a) PGE-type compounds when the cyclopentane moiety is:

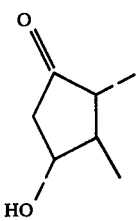

(b) PGF$_\alpha$-type compounds when the cyclopentane moiety is:

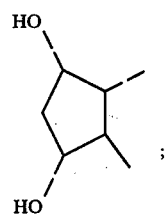

(c) PGF$_\beta$-type compounds when the cyclopentane moiety is:

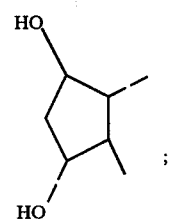

(d) PGA-type compounds when the cyclopentane moiety is:

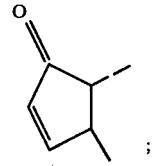

(e) PGB-type compounds when the cyclopentane moiety is:

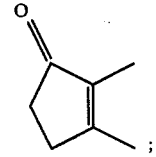

(f) 11-deoxy-PGE-type compounds when the cyclopentane moiety is:

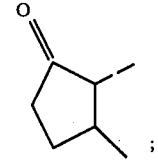

(g) 11-deoxy-PGF$_\alpha$-type compounds when the cyclopentane moiety is:

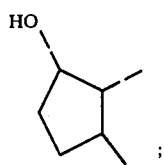

(h) 11-deoxy-PGF$_\beta$-type compounds when the cyclopentane moiety is:

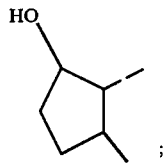

(i) 8β,12α-PGE-type compounds when the cyclopentane moiety is:

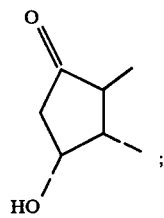

(j) 8β,12α-PGF$_\alpha$-type compounds when the cyclopentane moiety is:

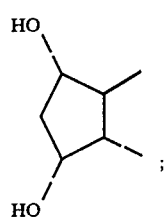

(k) 8β,12α-PGF$_\beta$-type compounds when the cyclopentane moiety is:

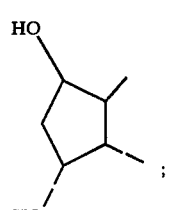

(l) 8β,12α-PGA-type compounds when the cyclopentane moiety is:

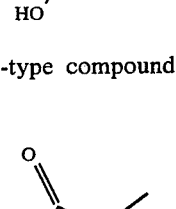

(m) 8β,12α-11-deoxy-PGF$_\beta$-type compounds when the cyclopentane moiety is:

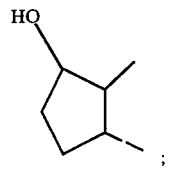

(n) 8β,12α-11-deoxy-PGE-type compounds when the cyclopentane moiety is:

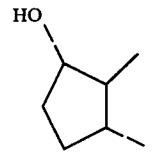

and (o) 8β,12α-11-deoxy-PGF$_\alpha$-type compounds when the cyclopentane moiety is:

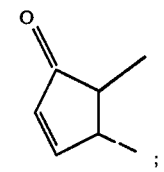

Those prostaglandin analogs herein wherein $Z_1$ is cis—CH=CH—CH$_2$-(CH$_2$)$_g$—cH$_2$— or cis—CH=•CH—CH$_2$—(CH$_2$)$_g$—CF$_2$— are named as "PG$_2$" compounds. The latter compounds are further characterized as "2,2-difluoro" PG-type compounds.

When g is 2 or 3, the prostaglandin analogs so described are "2a-homo" or "2a,2b-dihomo" compounds, since in this event the carboxy terminated side chain contains 8 or 9 carbon atoms, respectively, in place of the 7 carbon atoms contained in PGE$_1$. These additional carbon atoms are considered as though they were inserted between the C-2 and C-3 positions. Accordingly, these additional carbon atoms are referred to as C-2a and C-2b, counting from the C-2 to the C-3 position.

Further when $Z_1$ is —(CH$_2$)$_3$—(CH$_2$)$_g$—CH$_2$— or —(CH$_2$)$_3$—(CH$_2$)$_g$—CF$_2$, wherein g is as defined above, the compounds so described are "PG$_1$" compounds. When g is 2 or 3, the "2a-homo" and "2a,2b-dihomo" compounds are described as is discussed in the preceding paragraph.

When $Z_1$ is —CH$_2$—O—CH$_2$—(CH$_2$)$_g$—CH$_2$— the compounds so described are named as "5-oxa-PG$_1$" compounds. When g is 2 or 3, the compounds so described are "2a-homo" or "2a,2b-dihomo" compounds, respectively, as discussed above.

When $Z_1$ is —(CH$_2$)$_2$—O—(CH$_2$)$_g$—CH$_2$—, wherein g is as defined above, the compounds so described are named as "4-oxa-PG$_1$" compounds. When g is 2 or 3, the compounds so described are additionally characterized as "2a-homo" or "2a,2b-dihomo" compounds, respectively, as is discussed above.

When $Z_1$ is —(CH$_2$)$_3$—O—(CH$_2$)$_g$—, wherein g is as defined above, the compounds so described are named as "3-oxa-PG$_1$" compounds. When g is 2 or 3, the compounds so described are further characterized as "2a-homo" or "2a,2b-dihomo" compounds, respectively, as is discussed above.

When $Z_1$ is cis—$CH_2$—CH=CH—$(CH_2)_g$—$CH_2$—; wherein g is as defined above, the compounds so described are named "cis-4,5-didehydro-PG$_1$" compounds. When g is 2 or 3, the compounds so described are further characterized as "2a-homo" or "2a,2b-dihomo" compounds, respectively, as discussed above.

For the novel compounds of this invention wherein $Z_1$ is

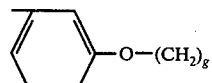

or

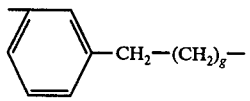

there are described, respectively, 3-oxa-3,7-inter-m-phenylene-4,5,6-trinor- or 3,7-inter-m-phenylene-4,5,6-trinor-PG-type compounds, when g is 1. When g is 2 or 3, the above compounds are additionally described as "2a-homo" or "2a,2b-dihomo" PG-type compounds, respectively.

The novel prostaglandin analogs of this invention contain a —C≡C— moiety at the C-13 to C-14 position, and are accordingly, referred to as "13,14-didehydro" compounds.

When $R_7$ is —$(CH_2)_m$—$CH_3$, wherein m is as defined above, the compounds so described are named as "19,20-dinor", "20-nor", "20-methyl", or "20-ethyl" compounds when m is one, 2, 4, or 5, respectively.

When $R_7$ is

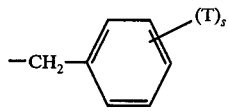

wherein T and s are as defined above, the compounds so described are named as "17-phenyl-18,19,20-trinor" compounds, when s is 0. When s is one, 2, or 3, the corresponding compounds are named as "17-(substituted phenyl)-18,19,20-trinor" compounds.

When $R_7$ is

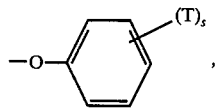

wherein T and s are as defined above, and neither $R_3$ nor $R_4$ is methyl, the compounds so described are named as "16-phenoxy-17,18,19,20-tetranor" compounds, when s is zero. When s is one, 2, or 3, the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When $R_7$ is cis—CH=CH—$CH_2$—$CH_3$, the compounds so described are "PG$_3$" or "17,18,-didehydro-PG$_1$" compounds depending on whether $Z_1$ is cis—CH=CH—$(CH_2)_g$—$C(R_2)_2$, wherein $R_2$ is hydrogen or fluoro; or another moiety, respectively.

When at least one of $R_3$ and $R_4$ is not hydrogen then (except for the 16-phenoxy compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $R_5$ is methyl, the compounds so described are named as "15-methyl" compounds. When $R_6$ is methyl, the compounds so described are named as "15-methyl ether" compounds.

There is further provided by this invention both epimeric configurations of the hydroxy or methoxy at C-15. As discussed herein, PGE$_1$, as obtained from mammalian tissues, has the "S" configuration at C-15. Further, as drawn herein PGE$_1$, as obtained from mammalian tissues, has the 15-hydroxy moiety in the "alpha" configuration.

For the 13,14-didehydro derivative of PGE$_1$ as obtained from mammalian tissues, the S configuration at C-15 represents the α-hydroxy configuration, using the convention by which the side chains of the novel prostaglandin analogs of this invention are drawn herein, as indicated above. Further, (15R)-PGE$_1$, by the convention used for drawing the prostaglandins herein, has the 15-hydroxy substituent in the beta configuration. The corresponding (15R)-13,14-didehydro-PGE$_1$ compound, drawn using the convention herein for the representation of the novel prostaglandin analogs of this invention, likewise has the 15-hydroxy in the beta configuration. Thus, the novel prostaglandin analogs of this invention wherein the 15-hydroxy or 15-methoxy moiety has the same absolute configuration as (15R)-13,14-didehydro-PGE$_1$ at C-15 will be named "15-epi" compounds. When the designation "15-epi" is absent, those compounds wherein the configuration of the 15-hydroxy or 15-methoxy is the same as the absolute configuration of 15(S)-13,14-didehydroPGE$_1$ are represented, i.e. the 15α-hydroxy configuration.

Accordingly, as indicated by the preceeding paragraphs, the novel PG analogs disclosed herein are named according to the system described in Nelson, N.A., J. Med. Chem. 17, 911 (1974).

Examples of alkyl of one to 12 carbon atoms, inclusive, are methyl, ethyl, propyl, butyl, pentyl, hexyl, heptyl, octyl, nonyl, decyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of

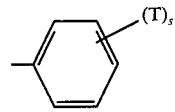

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, p-)fluorophenyl, 2,3,6-, or 2,4,5-)trimethylphenyl, (o-, m-, or p-(fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-(chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4chloro-3-fluorophenyl, (3- or 4-(chloro-2-fluorophenyl, o-, m-, or p-trifluoromethylphenyl, (o-m-, or p-)methoxyphenyl, (o-, m-, or p-)ethoxyphenyl, (4- or 5-)chloro-2-methoxyphenyl, and 2,4-dichloro(5- or 6-)methylphenyl.

The novel prostaglandin analogs of this invention correspond to the prostaglandins described above, in that the novel prostaglandin analogs exhibit prostaglandin-like activity.

Specifically the $8\beta,12\alpha$-PGE-, 11-deoxy-$8\beta,12\alpha$-PGE-, PGE-, and 11-deoxy-PGE-type compounds of this invention correspond to the PGE compounds described above, in that these novel PGE- and 11-deoxy-PGE-type compounds are useful for each of the above-described purposes for which the PGE compounds are used, and are used in the same manner as the PGE compounds, as described above.

The $8\beta,12\alpha$-$PGF_\alpha$-, 11-deoxy-$8\beta,12\alpha$-$PGF_\alpha$-, $PGF_\alpha$- and 11-deoxy-$PGF_\alpha$-type compounds of this invention correspond to the $PGF_\alpha$ compounds described above, in that these novel $PGF_\alpha$- and 11-deoxy-$PGF_\alpha$-type compounds are useful for each of the above-described purposes for which the $PGF_\alpha$ compounds are used, and are used in the same manner as the $PGF_\alpha$ compounds, as described above.

The $8\beta,12\alpha$-$PGF_\beta$-, 11-deoxy-$8\beta,12\alpha$-$PGB_\beta$, $PGF_\beta$- and 11-deoxy-$PGF_\beta$-type compounds of this invention correspond to the $PGF_\beta$ compounds described above, in that these novel $PGF_\beta$- and 11-deoxy-$PGF_\beta$-type compounds are useful for each of the above-described purposes for which the $PGB_\beta$ compounds are used, and are used in the same manner as the $PGF_\beta$ compounds, as described above.

The $8\beta,12\alpha$-PGA- and PGA-type compounds of this invention correspond to the PGA compounds described above, in that these novel PGA-type compounds are useful for each of the above described purposes for which the PGA compounds are used, and are used in the same manner as the PGA compounds, as described above.

The PGB-type compounds of this invention correspond to the PGB compounds described above, in that these PGB-type compounds are useful for each of the above described purposes for which the PGB compounds are used, and are used in the same manner as the PGB compounds, as described above.

The prostaglandins described above, are all potent in causing multiple biological responses even at low doses. Moreover, for many applications, these prostaglandins have an inconveniently short duration of biological activity. In striking contrast, the novel prostaglandin analogs of this invention are substantially more selective with regard to potency in causing prostaglandin-like biological responses, and have a substantially longer duration of biological activity. Accordingly, each of these novel prostaglandin analogs is surprisingly and unexpectedly more useful than one of the corresponding prostaglandins described above for at least one of the pharmacological purposes indicated above for the latter, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Another advantage of the novel prostaglandin analogs of this invention, especially the preferred PG analogs defined hereinbelow, compared with the corresponding prostaglandins, is that these novel PG analogs are administered effectively orally, sublingually, intravaginally, buccally, or rectally in those cases wherein the corresponding prostaglandin is effective only by the intravenous, intramuscular, or subcutaneous injection or infusion methods of administration indicated above as uses of these prostaglandins. These alternate routes of administration are advantageous because they facilitate maintaining uniform levels of these compounds in the body with fewer, shorter, or smaller doses and make possible self-administration by the patient.

Accordingly, the novel prostaglandin analogs of this invention are administered in various ways for various purposes: e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For intravenous injectionor infusion, sterile aqueous isotonic solutions are preferred. For that purpose, it is preferred because of increased water solubility that $R_1$ in the novel compounds of this invention be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The chemical structure of the novel 11-deoxyPGE-type compounds of this invention renders them less sensitive to dehydration and rearrangement than the corresponding prostaglandins, and these compounds accordingly exhibit a surprising and unexpected stability and duration of shelf life.

The novel PG analogs of this invention are used for the purposes described above in the free acid form, in ester form, in pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araaliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, Nbutylethanolamine, 2-amino-1-butanol,2-amino-2-ethyl-1,3-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylgycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

The novel PG analogs of this invention are used for the purposes described above in free hydroxy form or also in the form wherein the hydroxy moieties are transformed to lower alkanoate moieties such as acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

To obtain the optimum combination of biological response specificity, potency, and duration of activity, certain compounds within the scope of this invention are preferred.

It is preferred that the carboxy-terminated side chain contain either 7 or 9 carbon (or carbon and oxygen) atoms, especially preferred that it contain 7, i.e., the natural chain length of the prostaglandins. Further when the other side chain contains —$(CH_2)_m$—$CH_3$, it is preferred that $m$ be 3. For those compounds wherein $R_7$ is

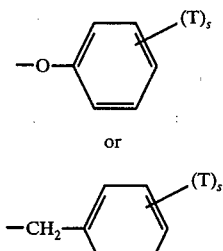

it is preferred that s be zero or one and T be chloro, fluoro, or trifluoromethyl.

For those compounds wherein at least one of $R_3$ and $R_4$ is methyl or fluoro, it is preferred that $R_5$ and $R_6$ both be hydrogen. For those compounds wherein at least one of $R_5$ and $R_6$ is methyl, it is preferred that $R_3$ and $R_4$ both be hydrogen. For those compounds wherein $R_7$ is

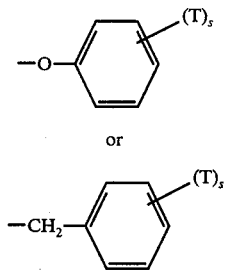

it is preferred that $R_3$, $R_4$, $R_5$, and $R_6$ all be hydrogen.

For those compounds wherein an oxa is substituted for a methylene (i.e., —O— for —$CH_2$—), it is preferred that such substitution occur at C-5.

It is further preferred that the 15-hydroxy or 15-methoxy not be of the 15-epi configuration, i.e., that the hydroxy be in the alpha configuration when the formulas of the novel 13,14-didehydro-PG analogs are as drawn herein.

Especially preferred are those compounds which satisfy two or more of the above preferences. Further, the above preferences are expressly intended to describe the preferred compounds within the scope of any generic formula of novel prostaglandin analogs disclosed herein. Thus, for example the above preferences describe preferred compounds within the scope of each formula of a prostaglandin analog provided in the Tables hereinafter.

In another aspect of the interpretation of the preferences herein, the various prostaglandin cyclopentane ring structures as employed herein are each representative of a particular "parent structure" which is useful in naming and catagorizing the novel prostaglandin analogs disclosed herein. Further, where a formula depicts a general of PG analogs disclosed herein evidencing a single cyclopentane ring structure, then each corresponding genus of PG analogs evidencing one of the remaining cyclopentane ring structures cited herein for novel prostaglandin analogs is intended to represent an equally preferred genus of compounds. Thus, for example, for each genus of $PGF_{60}$-type products depicted by a formula herein, the corresponding genus of $PGF_{62}$-, PGE, and 11-deoxy-$PGF_{60}$-type products are equally preferred embodiments of the invention as the genus of $PGF_{60}$-type products.

Finally where subgeneric grouping of PG analogs of any cyclopentane ring structure are described herein, then the corresponding subgeneric groupings of PG analogs of each of the remaining cyclopentane ring structures are intended to represent equally preferred embodiments of the present invention.

The Charts herein describe methods whereby the novel prostaglandin analogs of this invention are prepared.

With respect to the Charts $R_1$, $Y_1$, $R_7$, $M_1$, $L_1$, $Z_1$, and $g$ are as defined above; D is as variously defined above $M_5$ is

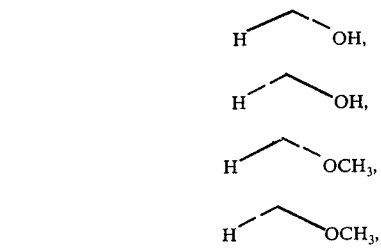

or a mixture of

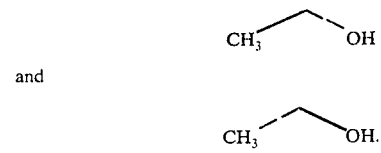

and

$M_6$ is

CHART A

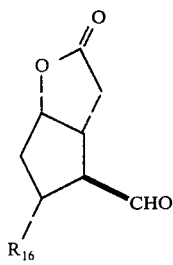

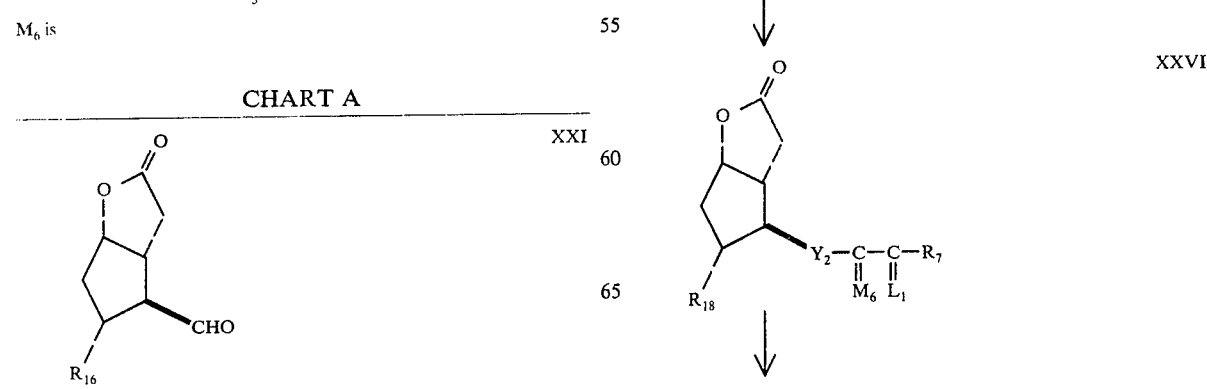

CHART A-continued
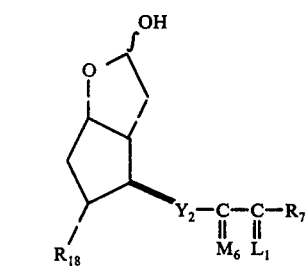
XXVII
CHART B
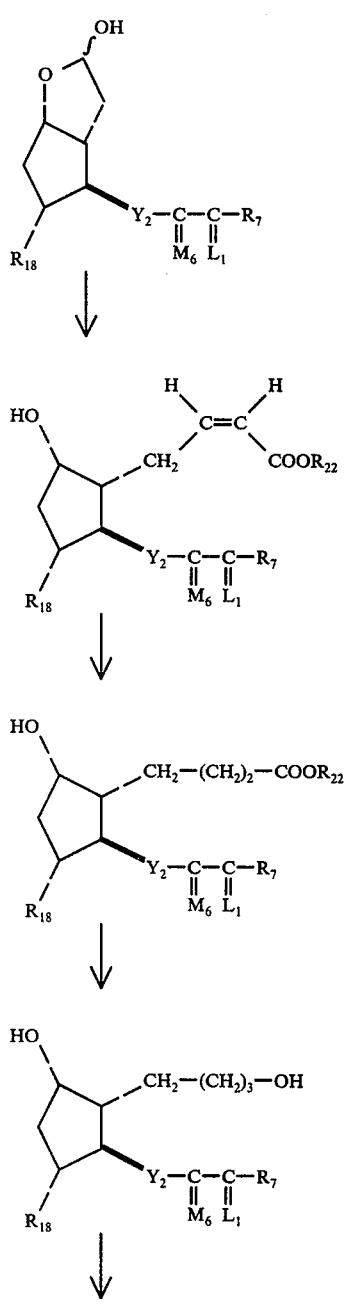
XXXI
XXXII
XXXIII
XXXIV
CHART B-continued
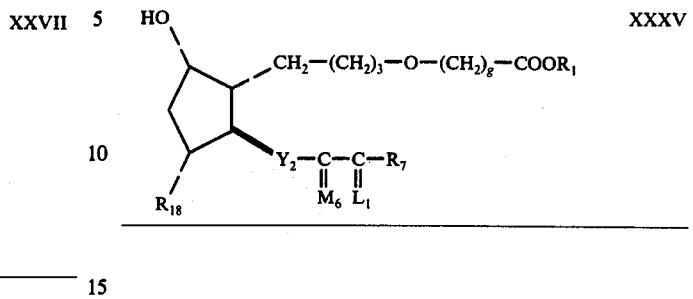
XXXV
CHART C
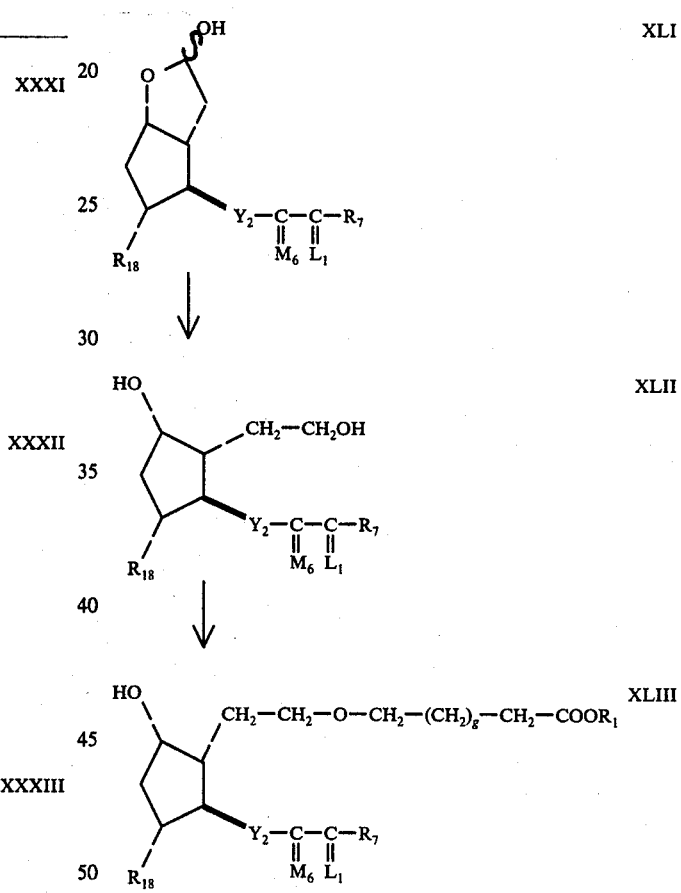
XLI
XLII
XLIII
CHART D
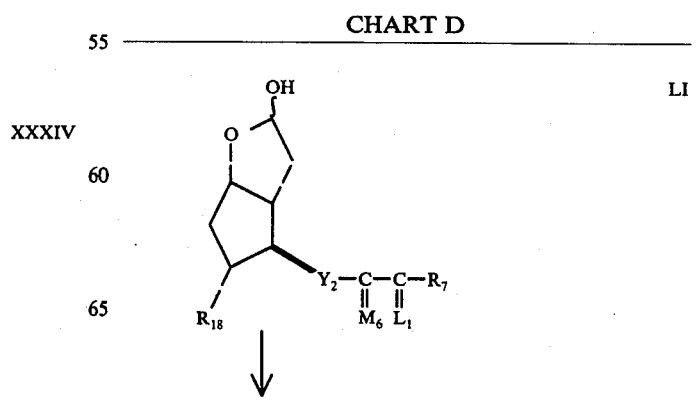
LI

CHART D-continued
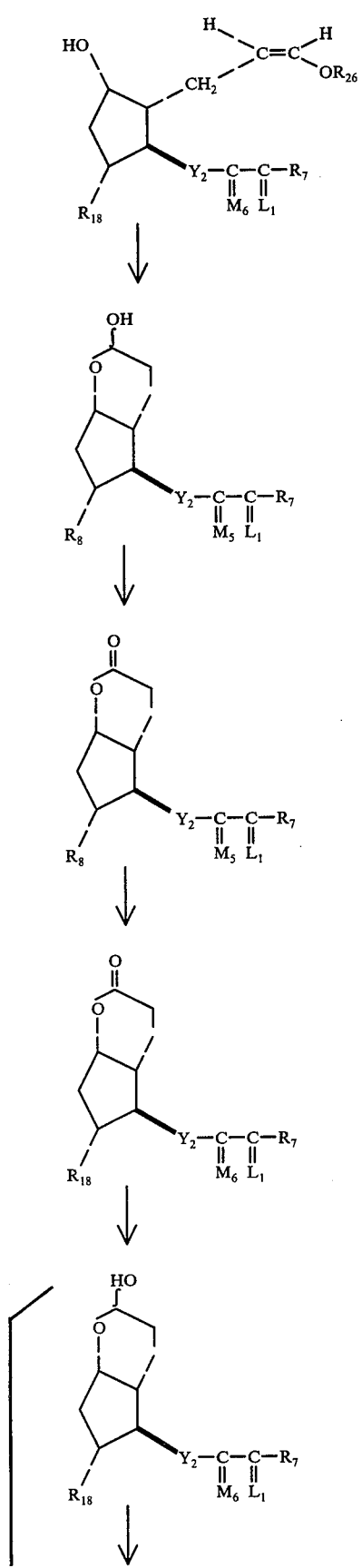
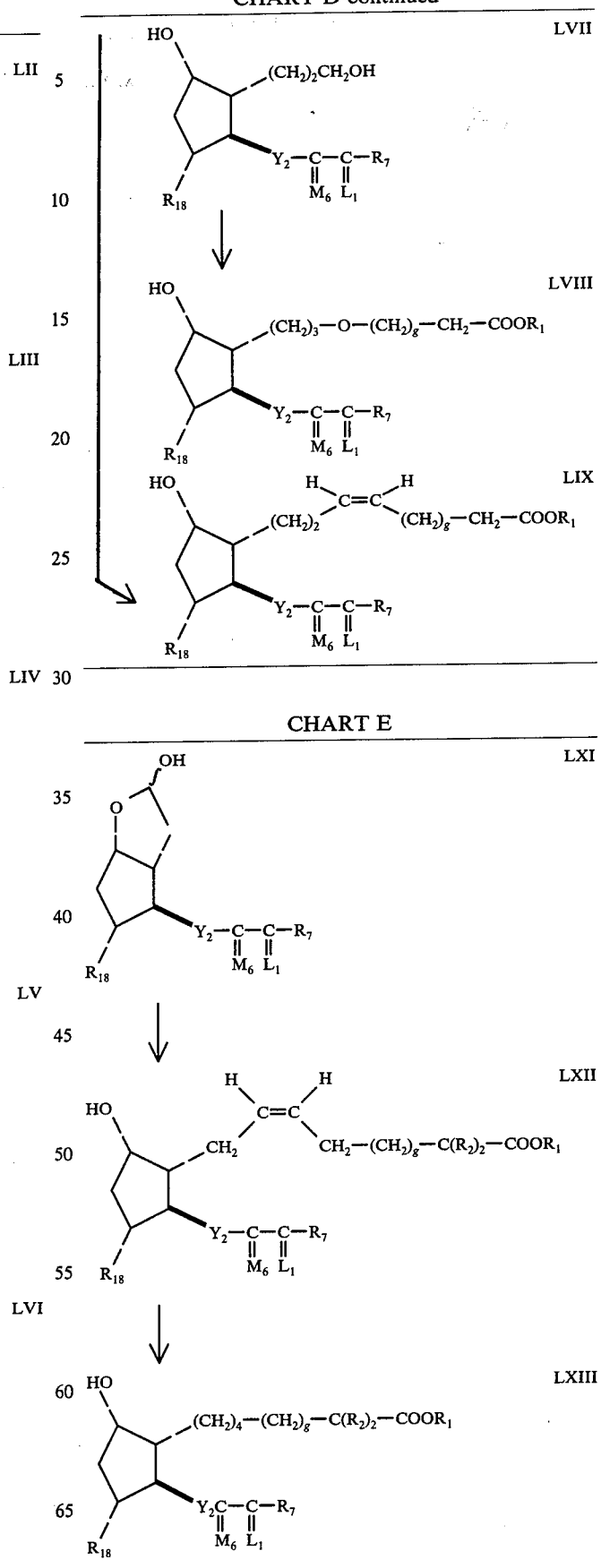

33 34
CHART F | CHART F-continued
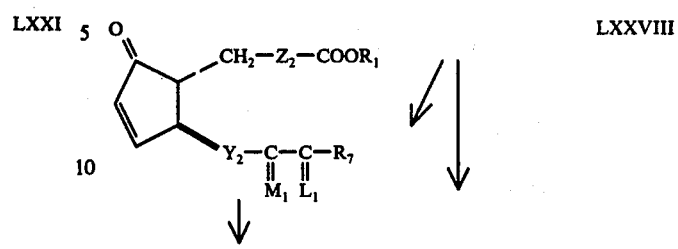
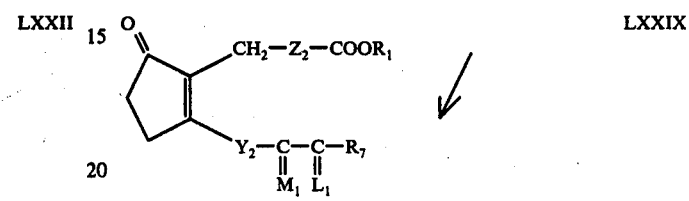
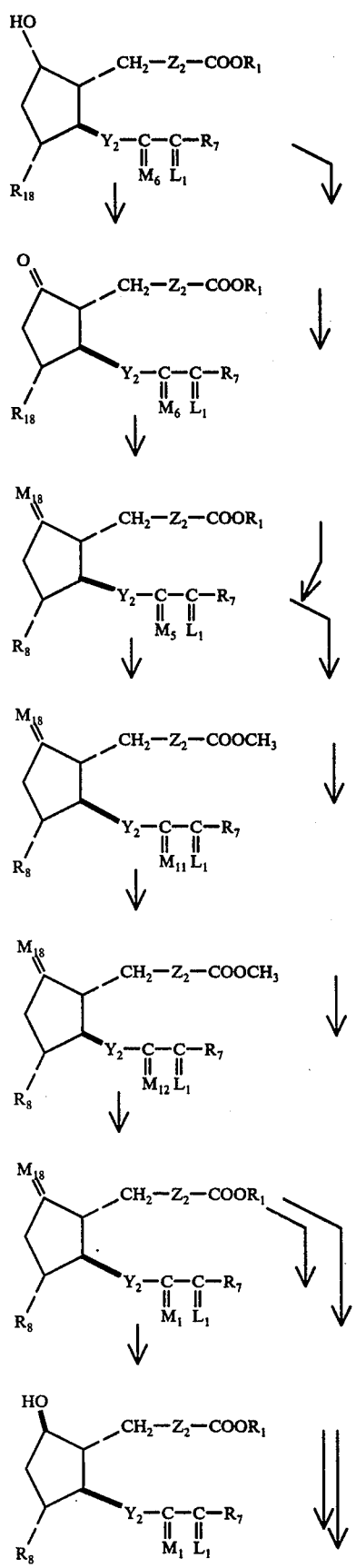
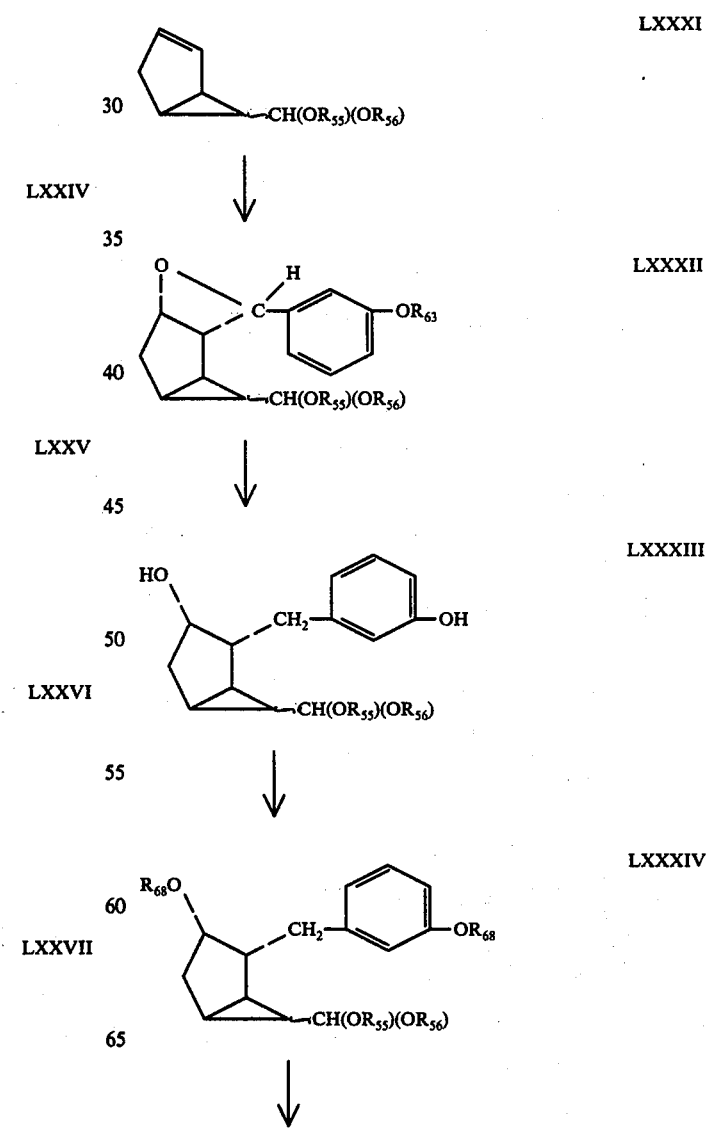
CHART G

CHART G-continued
LXXXV
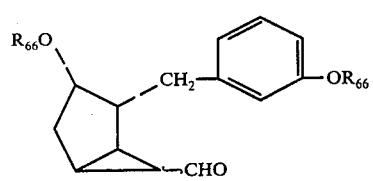
LXXXVI
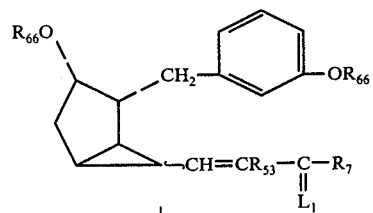
LXXXVII
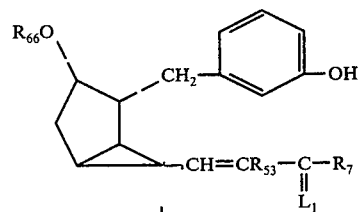
LXXXVIII
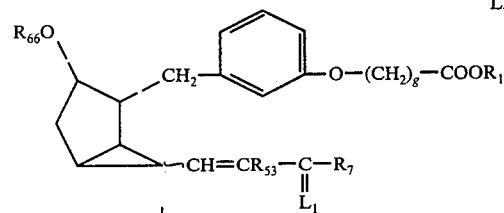
LXXXIX
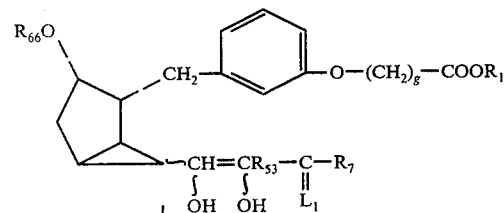
XC
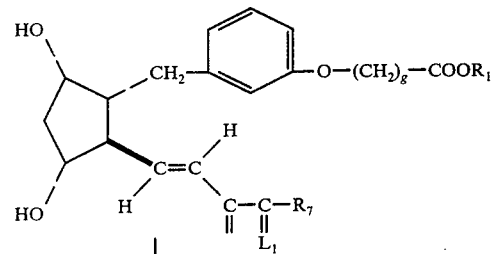
CHART G-continued
XCI
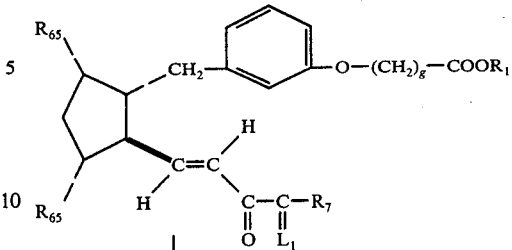
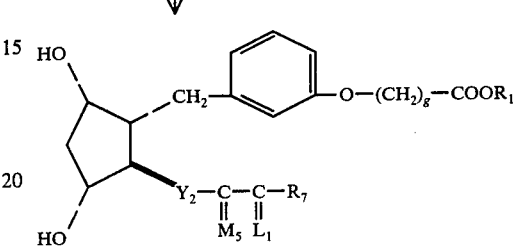
XCII
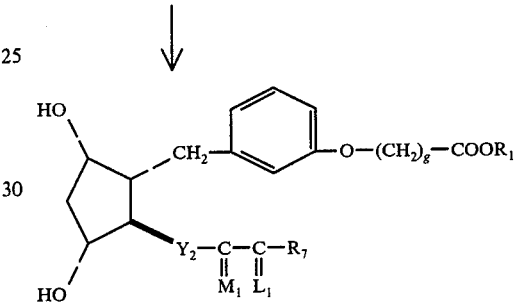
XCIII
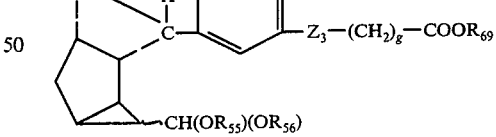
CHART H
XCVI
XCVII
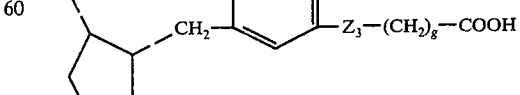
XCVIII

-continued
CHART H
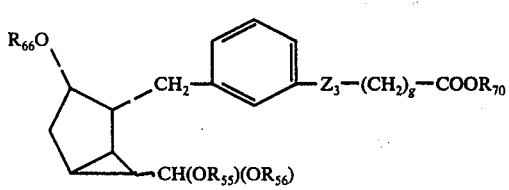
XCIX
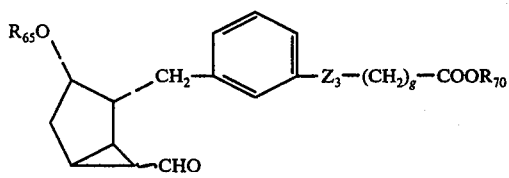
C
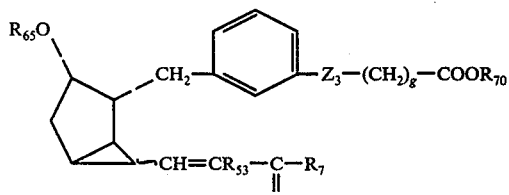
CI
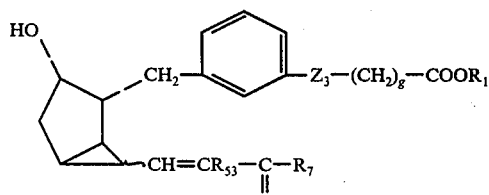
CII
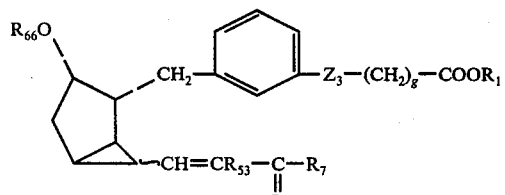
CIII
-continued
CHART H
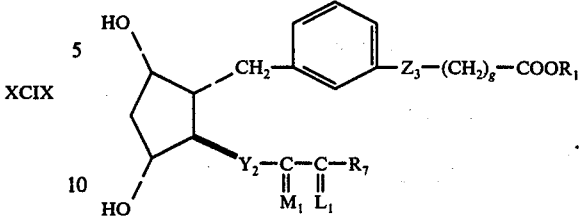
CIV
CHART I
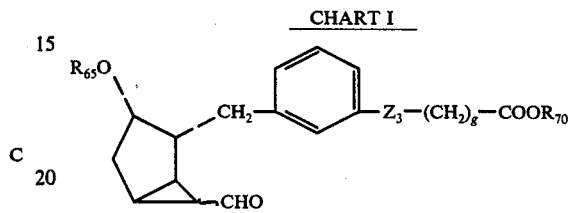
CVI
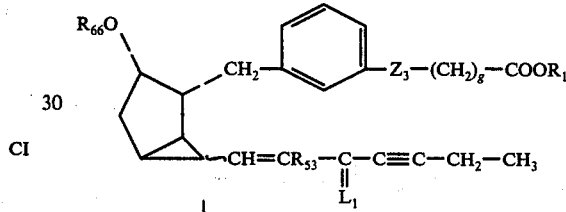
CVII
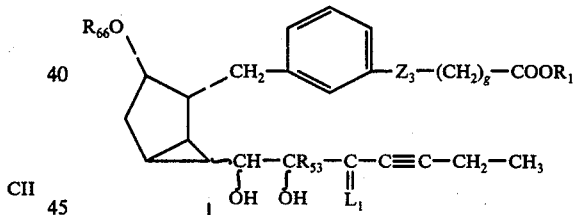
CVIII
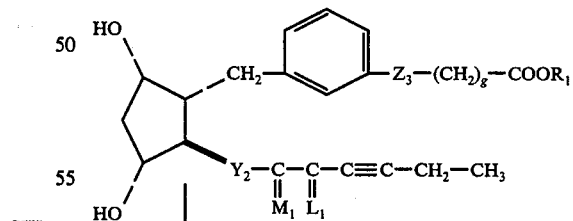
CIX
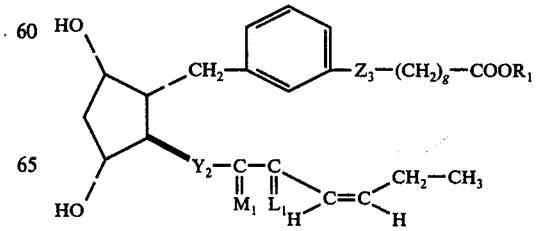
CX

Chart J
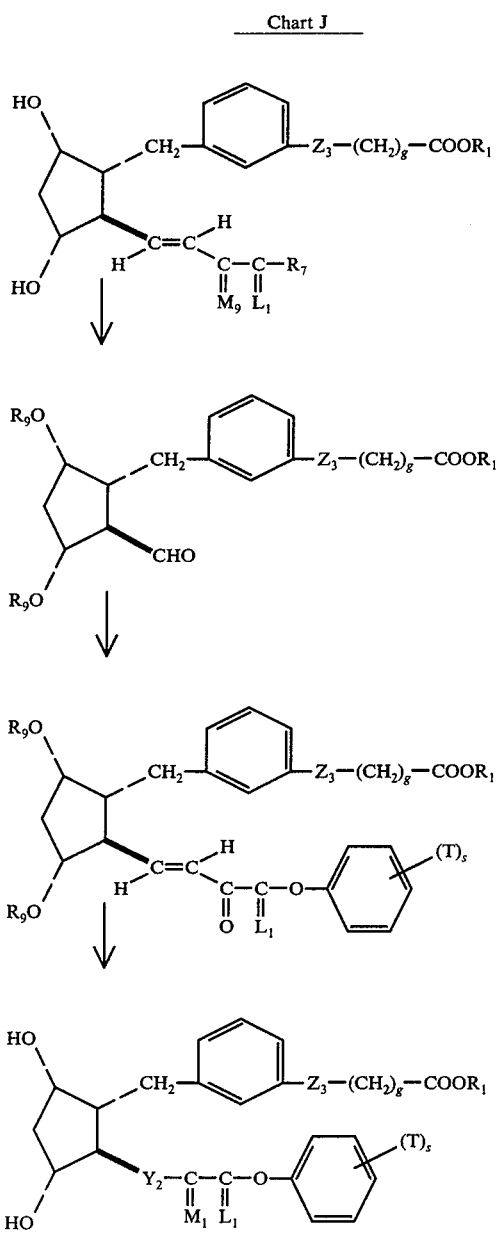
Chart K
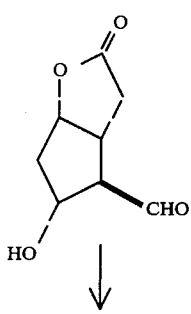
Chart K -continued
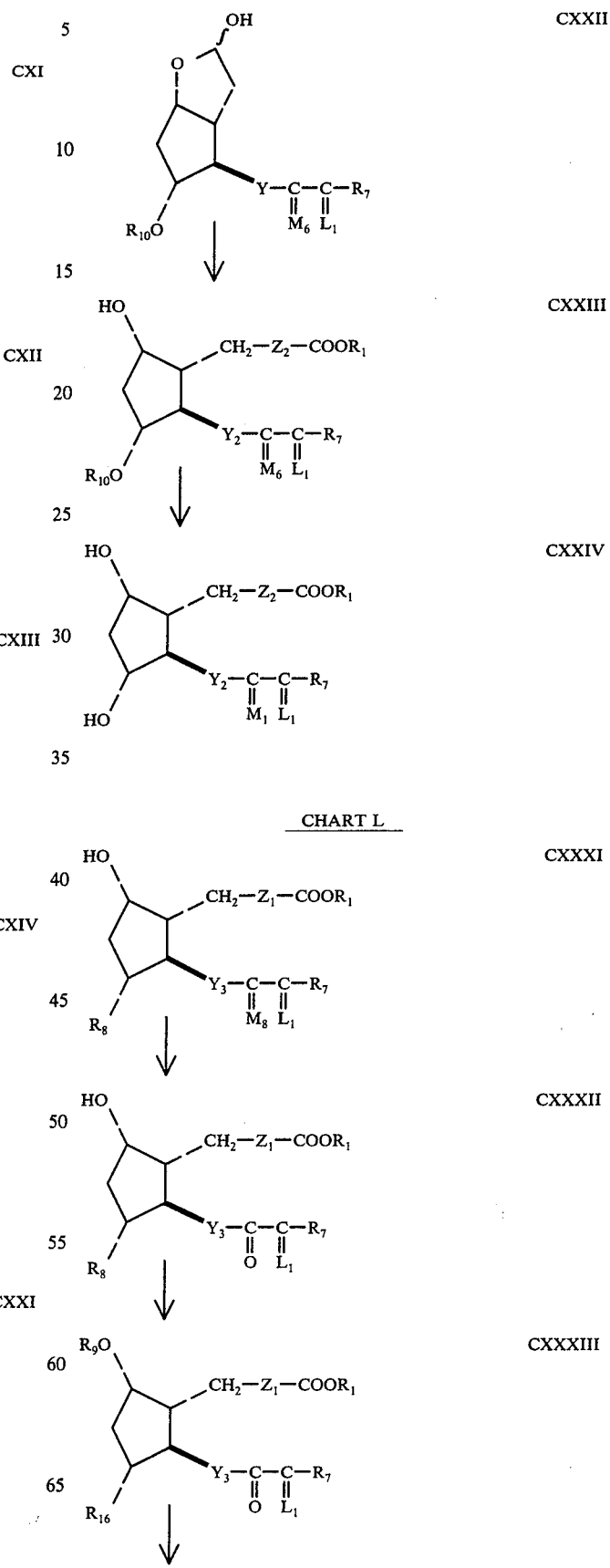

-continued
CHART L
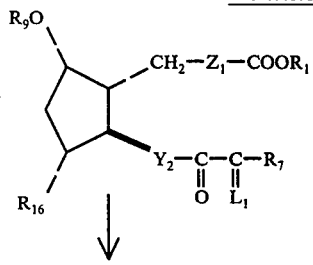
CXXXIV
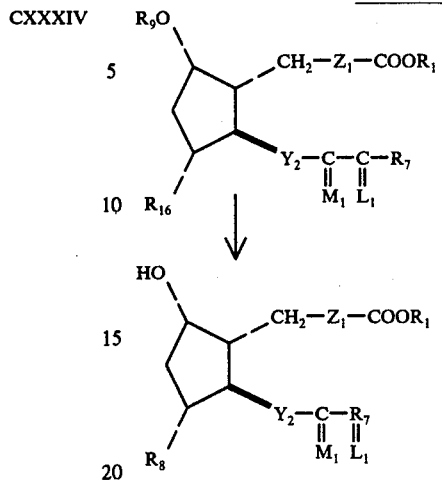
CXXXV
CXXXVI
CHART M
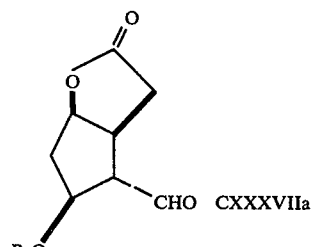
CXXXVIIa
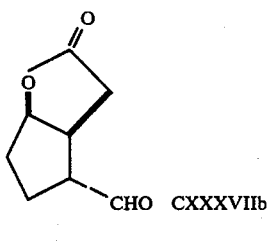
CXXXVIIb
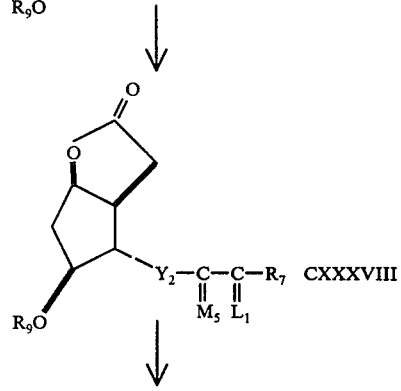
CXXXVIII
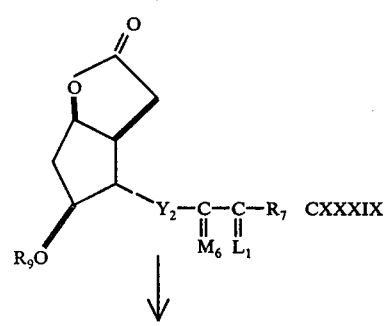
CXXXIX -continued
CHART M
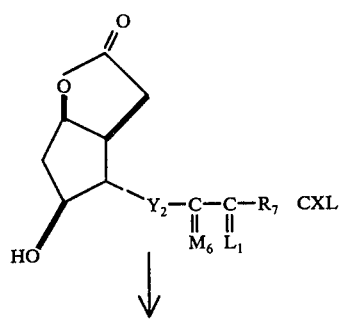 CXL
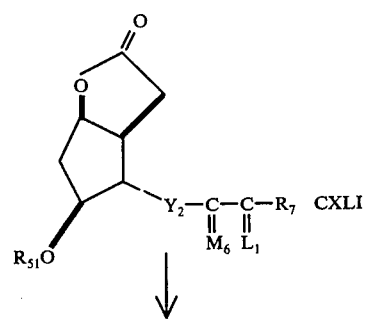 CXLI
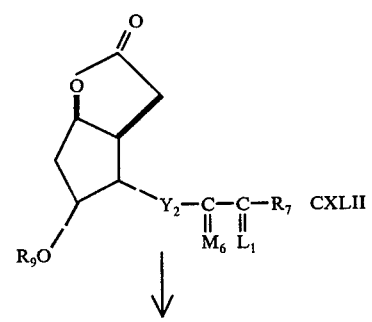 CXLII
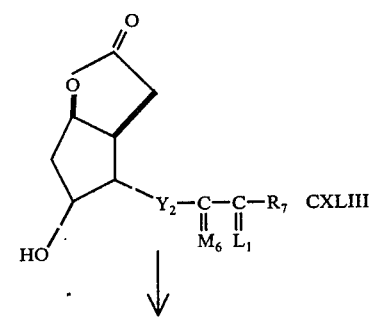 CXLIII
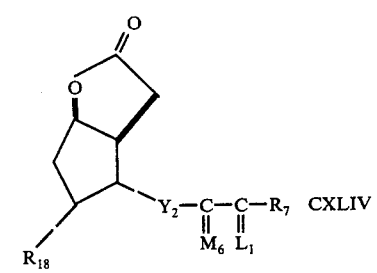 CXLIV CHART M
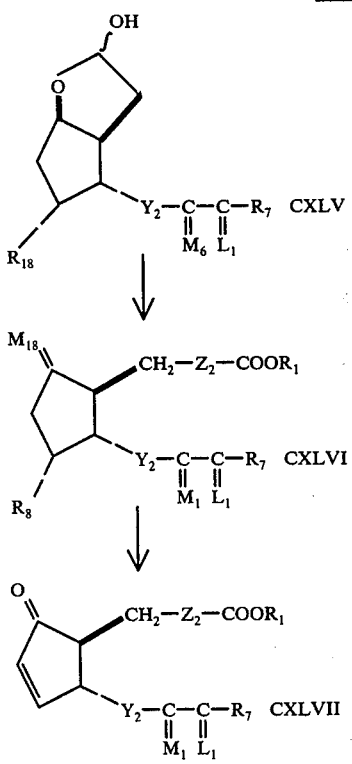
CHART N
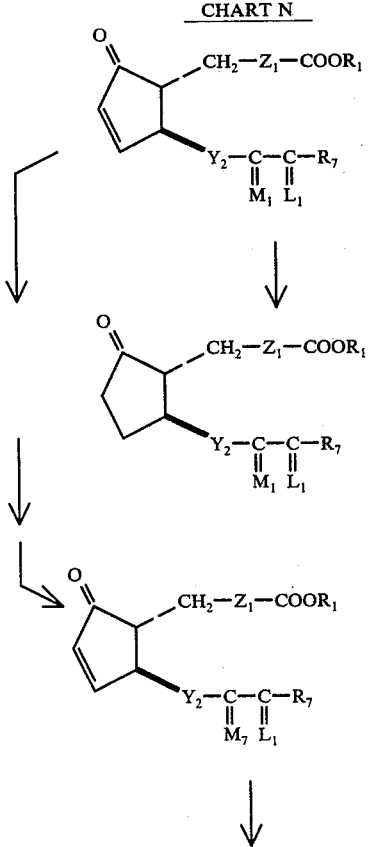
-continued
CHART N
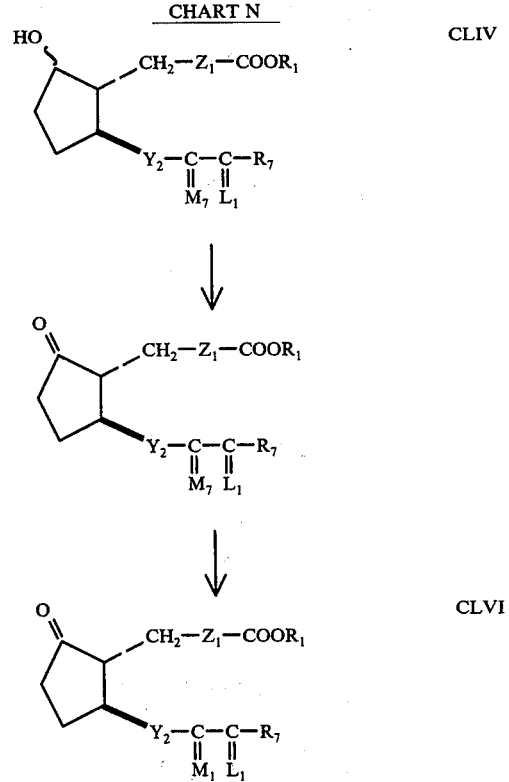

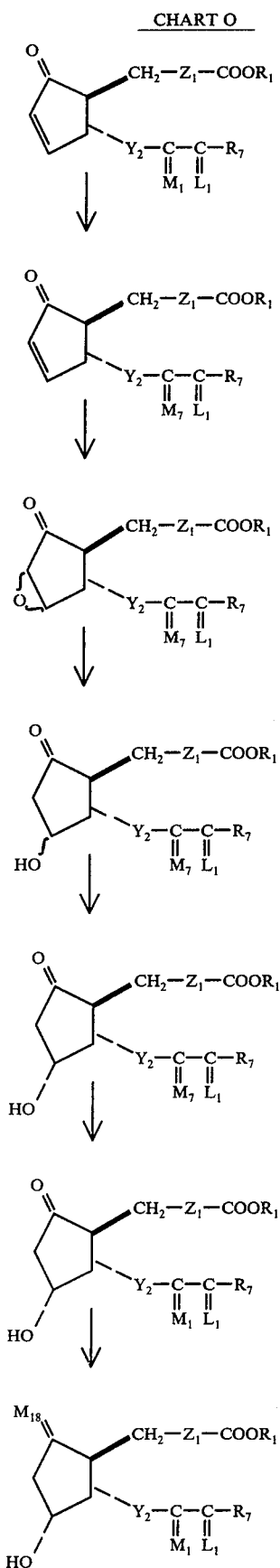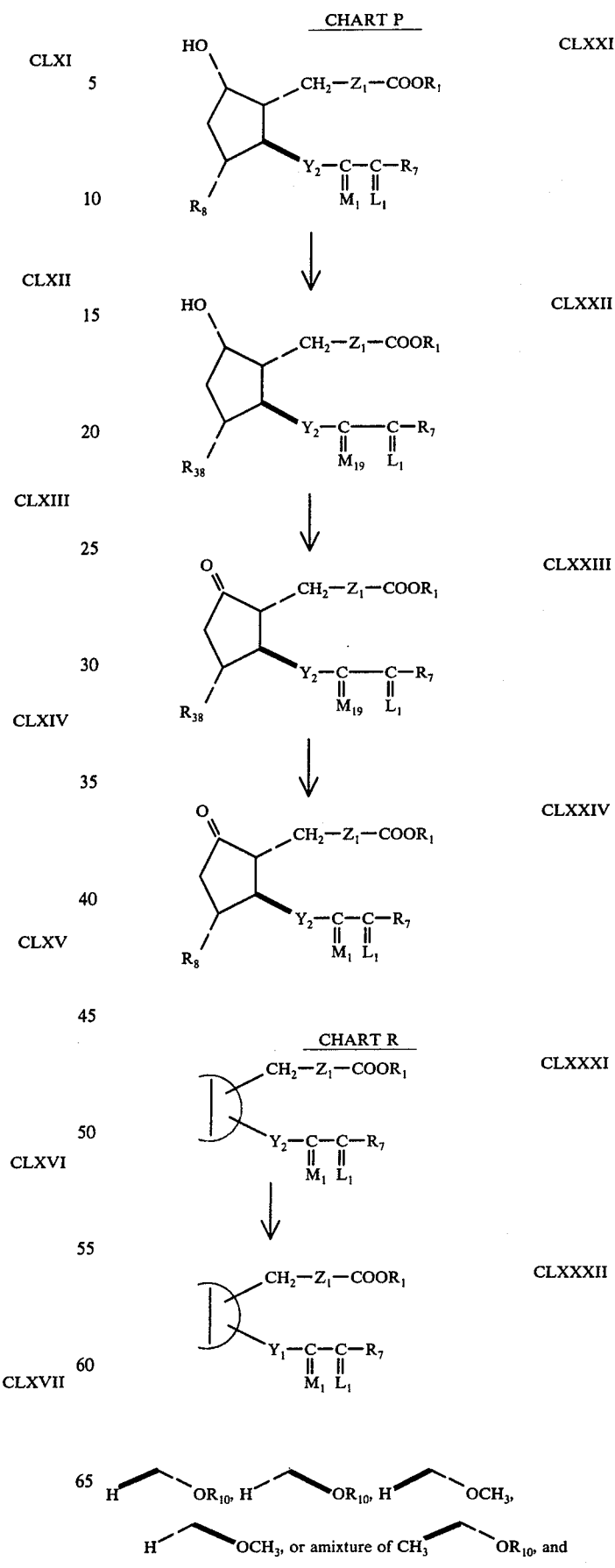

-continued

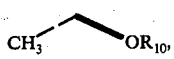

wherein $R_{10}$ is a blocking group.

$M_7$ is 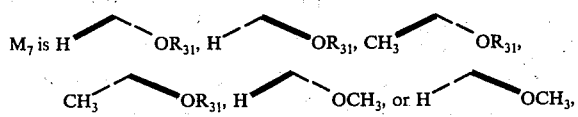

wherein $R_{31}$ is a blocking group as defined hereinbelow in the text accompanying Chart N.

$M_9$ is

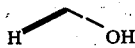

or

$M_{11}$ is a mixture of

and

$M_{12}$ is

or

$M_{18}$ is $\overset{O}{\underset{\|}{}}$,

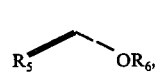

$M_{19}$ is

or

when $R_6$ is methyl, and

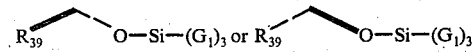

when $R_6$ is hydrogen, wherein $R_{39}$ is hydrogen or methyl, being the same as $R_5$.

$R_2$ is hydrogen or fluoro. $R_8$ is hydrogen or hydroxy. $R_{16}$ is hydrogen or $-OR_9$, wherein $R_9$ is an acyl protecting group as defined below. $R_{18}$ is hydrogen or $-OR_{10}$, wherein $R_{10}$ is as defined above. $R_{22}$ is methyl or ethyl. $R_{26}$ is hydrocarbyl, including alkyl, aralkyl, cycloalkyl, and the like. Examples of these hydrocarbyl groups include 2-methylbutyl, isopentyl, heptyl, octyl, nonyl, tridecyl, octadecyl, benzyl, phenethyl, p-methylphenethyl, 1-methyl-3-phenylpropyl, cyclohexyl, phenyl, and p-methylphenyl, $G_1$ is alkyl of one to 4 carbon atoms, cycloalkyl of 3 to 10 carbon atoms, inclusive, aralkyl of 7 to 12 carbon atoms, phenyl, or phenyl substituted with one or 2 fluoro, chloro, or alkyl of one to 4 carbon atoms, with the proviso that in the $-Si-(G_1)_3$ moiety the various $G_1$'s are the same or different. $R_{38}$ is hydrogen or $-O-Si-(G_1)_3$, wherein $G_1$ is as defined above.

$R_9$ is an acyl protecting group. Acyl protecting groups according to $R_9$, include:

(a) Benzoyl;

(b) Benzoyl substituted with one to 5, inclusive, alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;

(c) Benzoyl substituted with alkoxycarbonyl of 2 to 5 carbon atoms, inclusive;

(d) Naphthoyl;

(e) Naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or (f) Alkanoyl of 2 to 12 carbon atoms, inclusive.

In preparing these acyl derivatives of a hydroxy-containing compound herein, methods generally known in the art are employed. Thus, for example, an aromatic acid of the formula $R_9OH$, wherein $R_3$ is as defined above (e.g., benzoic acid), is reacted with the hydroxy-containing compound in the presence of a dehydrating agent, e.g. sulfuric acid, zinc chloride, or phosphoryl chloride; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxy-containing compound in the presence of a hydrogen chloride scavenger, e.g. a tertiary amine such a pyridine, triethylamine or the like. The reaction is carried out under a variety of conditions, using procedures generally known in the art. Generally mild conditions are employed: 20°-60° C., contacting the reactants in a liquid medium (e.g., excess pyridine or an inert solvent such as benzene, toluene, or chloroform). The acylating agent is used either in stoichiometric amount or in a substantial stoichiometric excess.

As examples of $R_9$, the following compounds are available as acids ($R_9OH$), anhydrides (($R_9)_2O$), or acyl chlorides ($R_9Cl$): benzoyl; substituted benzoyl, e.g., 2-, 3-, or 4-)-metylbenzoyl, (2-, 3-, or 4-)-ethyl benzoyl, (2-, 3-, or 4-)-isopropylbenzoyl, (2-, 3-, or 4-)-tert-butylbenzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl-2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benzyl-1-naphthol, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonates are employed effectively at ambient temperature for this purpose. For example, potassium carbonate in methanol at about 25° C. is advantageously employed.

Those blocking groups within the scope of $R_{10}$ are any group which replaces a hydroxy hydrogen and is neither attacked nor as reactive to the reagents used in the transformations used herein as an hydroxy is and which is subsequently replaceable with hydrogen in the preparation of the prostaglandin-type compounds. Several blocking groups are known in the art, e.g. tetrahydropyranyl and substituted tetrahydropyranyl. See for reference E. J. Corey, Proceedings of the Robert A. Welch Foundation Conferences on Chemical Research, 12, Organic Synthesis, pgs. 51–79 (1969). Those blocking groups which have been found useful include (a) tetrahydropyranyl;
(b) tetrahydrofuranyl; and
(c) a group of the formula

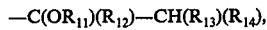

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —(CH$_2$)$_a$— or —(CH$_2$)$_b$— O—(CH$_2$)$_c$— wherein $a$ is 3, 4, or 5, or $b$ is one, 2, or 3, and $c$ is one, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichiometric excess, preferably 4 to 10 times the stoichiometric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

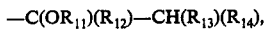

wherein $R_{11}$, $R_{12}$, $R_{13}$, and $R_{14}$ are as defined above, the appropriate reagent is a vinyl ether, e.g. isobutyl vinyl ether or any vinyl ether of the formula

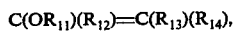

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

$R_{53}$ is hydrogen or alkyl of one to 4 carbon atoms, inclusive. $R_{55}$ and $R_{56}$ are alkyl of one to 4 carbon atoms, inclusive, being the same or different, or when taken together represent a group of the formula:

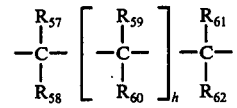

wherein $R_{57}$, $R_{58}$, $R_{59}$, $R_{60}$, $R_{61}$, and $R_{62}$ are hydrogen, alkyl of one to 4 carbon atoms, inclusive, or phenyl, being the same or different, with the proviso that not more than one of $R_{57}$, $R_{58}$, $R_{59}$, $R_{60}$, $R_{61}$, and $R_{62}$ is phenyl and that the total number of carbon atoms in $R_{57}$, $R_{58}$, $R_{59}$, $R_{60}$, $R_{61}$, and $R_{62}$ is from 2 to 10, inclusive, and $h$ is zero or one.

$R_{63}$ is a carboxyacyl of the formula

wherein $R_{64}$ is hydrogen, alkyl of one to 19 carbon atoms, inclusive, or aralkyl of 7 to 12 carbon atoms, inclusive, wherein the above alkyl or aralkyl are substituted with zero to 3 fluoro, chloro, bromo, or iodo. $R_{66}$ is hydrogen or a blocking group, according to $R_{65}$. Blocking groups according to $R_{65}$ useful for the purposes of this invention include all blocking groups according to $R_{10}$, as enumerated herein, and additionally -Si(G$_1$)$_3$, wherein G$_1$ is alkyl of one to 4 carbon atoms, inclusive, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, inclusive. In the use of these silyl blocking groups, according to $R_{65}$, methods known in the art for the preparation of the necessary reagents and appropriate reaction conditions for replacing hydroxy hydrogens with these silyl blocking groups and subsequently hydrolyzing these silyl blocking groups, are employed.

$R_{68}$ is hydrogen, carboxyacyl according to $R_{63}$, or an acyl protecting group according to $R_9$. $R_{69}$ is hydrogen, alkyl of one to 4 carbon atoms, inclusive, or silyl of the formula —Si(G$_1$)$_3$, wherein G$_1$ is as defined above. $R_{66}$ is hydrogen or optionally $R_{65}$, a blocking group.

$Y_2$ is trans—CH═C(Hal)—, wherein Hal is chloro, bromo, or iodo. $Y_3$ is trans—CH═CH. $Z_2$ is cis—CH═CH-CH$_2$—(CH$_2$)$_g$—C(R$_2$)$_2$—, cis—CH$_2$-CH═CH—(CH$_2$)$_g$—CH$_2$, —(CH$_2$)$_3$—(CH$_2$)$_g$—C(R$_2$)$_2$—, —CH$_2$—O—CH$_2$—(CH$_2$)$_g$—CH$_2$—, —(CH$_2$)$_2$—O—(CH$_2$)$_g$—CH$_2$—, or —(CH$_2$)$_3$—O—(CH$_2$)$_g$—, wherein $R_2$ and $g$ are as defined above. $A_3$ is oxa or methylene, e.g., —O— or —CH$_2$—, respectively.

With respect to Chart A the formula XXI compound is known in the art. This compound is available in either of two enantiomeric forms or as a mixture thereof. The formula XXI compound in racemic form may be transformed into corresponding optically active compound by methods known in the art.

The formula XXII compound is prepared from the formula XXI compound by a Wittig alkylation when $R_7$ is not 1-butenyl. Reagents known in the art or prepared by methods known in the art are employed. The transenone lactone is obtained stereospecifically. See for reference D. H. Wadsworth, et al., Journal of Organic Chemistry 30, 680 (1965).

In the preparation of the formula XXII compound, certain phosphonates are employed in the Wittig reaction. These phosphonates are of the general formula

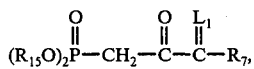

wherein $L_1$ and $R_7$ are as defined above (but $R_7$ is not 1-butenyl) and $R_{15}$ is alkyl of one to 8 carbon atoms, inclusive.

Phosphonates of the above general formula are prepared by methods known in the art. See Wadsworth, et al. as cited above.

Conveniently the appropriate aliphatic acid ester is condensed with the anion of dimethyl methylphosphonate as produced using n-butyllithium. For this purpose, acids of the general formula

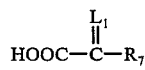

are employed in the form of their lower alkyl esters, preferably methyl or ethyl. The methyl esters for example are readily obtained by reaction of the corresponding acids with diazomethane.

For example, when $R_7$ is

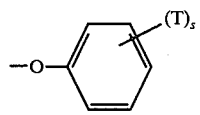

wherein T and s are as defined above, and $R_3$ and $R_4$ of the $L_1$ moiety are both hydrogen, the corresponding phenoxy or substituted phenoxy acetic acids are known in the art or readily available in the art. Those known in the art include those wherein the $R_7$ moiety is: phenoxy, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, (o-, m-, or p-)trifluoromethylphenoxy-, or (o-, m-, or p-)methoxyphenoxy-.

Further, many 2-phenoxy- or substituted phenoxy propionic acids are readily available, and are accordingly useful for the preparation of the acids of the above formula wherein one and only one of $R_3$ and $R_4$ of the $L_1$ moiety is methyl and $R_7$ is phenoxy or substituted phenoxy. These 2-phenoxy or 2-substituted phenoxy propionic acids include those wherein the $R_7$ moiety is p-fluoropheoxy-, (o-, m-, or p-)chlorophenoxy-, (2,3-, 2,4-, 2,5-, 2,6-, 3,4-, or 3,5-)dichlorophenoxy-, (4- or 6-chloro-o-tolyloxy-, phenoxy-, (o-, m-, or p-)tolyloxy, 3,5-xylyloxy-, or m-trifluoromethylphenoxy-.

Finally there are available many 2-methyl-2-phenoxy- or (2-substituted)phenoxypropionic acids, which are useful in the preparation of the above acids wherein $R_3$ and $R_4$ of the $L_1$ moiety are both methyl and $R_7$ is phenoxy or substituted phenoxy. These 2-methyl-2-phenoxy-, or (2-substituted)phenoxypropionic acids include those wherein $R_7$ is: phenoxy-, (o-, m-, or p-)chlorophenoxy-, (2,3-, 2,4-, 2,5-, 2,6-, 3,4-, or 3,5-)dichlorophenoxy-, Other phenoxy substituted acids are readily available by methods known in the art, for example, by Williamson synthesis of ethers using an α-halo aliphatic acid or ester with sodium phenoxide or a substituted sodium phenoxide. Thus, the $(T)_s$-substituted sodium phenoxide is reacted with, for example, the α-chloro aliphatic acid, or the alkyl ester derivative thereof, with heating to yield the acid of the above general formula, which is recovered from the reaction mixture by conventional purification techniques.

There are further available phenyl substituted acids of the above formula wherein $R_7$ is benzyl or substituted benzyl.

For example, when $R_3$ and $R_4$ of the $L_1$ moiety are both hydrogen there are available the following phenyl or substituted phenyl propionic acids: (o-, m-, or p-)-chlorophenyl-, p-fluorophenyl-, m-trifluoromethylphenyl-, (o-, m-, or p-methylphenyl-, (o-, m-, or p-)methoxyphenyl-, (2,4-, 2,5-, or 3,4-dichlorophenyl-, (2,3-, 2,4-, 2,5-, 2,6-, or 3,4-)dimethylphenyl-, or (2,3-, 2,4-, 2,5-, 2,6-, 3,4-, or 3,5-)dimethoxyphenyl-.

When one and only one of $R_3$ and $R_4$ of the $L_1$ moiety is methyl there are available, for example, the following 2-methyl-3-phenyl or substituted phenyl propionic acids: phenyl, o-chlorophenyl-, (o-, or p-)methylphenyl-, (o-, m-, or p-)methoxyphenyl-, (2,4- or 3,4-)difluorophenyl-, 2,3-dimethylphenyl-, and (2,3-, 3,4-, or 4,5-)dimethoxyphenyl-.

When both $R_3$ and $R_4$ are methyl there are available, for example, the following 2,2-dimethyl-3-phenyl or substituted phenyl propionic acids: phenyl- and p-methylphenyl.

When one and only one of $R_3$ and $R_4$ is fluoro, there is available, for example, 2-fluoro-3-phenyl propionic acid.

Phenyl substituted acids (as above wherein $R_7$ is benzyl) are available by methods known in the art, for example, by reacting a mixture of the appropriate methyl- or fluoro-substituted acetic acid, a secondary amine (e.g., diisopropylamine), n-butyllithium, and an organic diluent (e.g., tetrahydrofuran) with the appropriately substituted benzyl chloride. Thus the above acid is obtained by the following reaction:

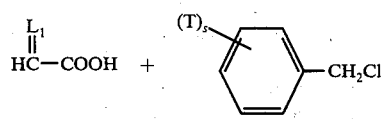

-continued

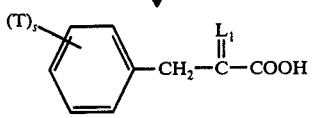

The above reaction proceeds smoothly, ordinarily at 0° C. The product acid is recovered using conventional methods.

For the acids of the above formula wherein $R_7$ is n-alkyl, many such acids are readily available.

For example, when $R_3$ and $R_4$ of the $L_1$ moiety are both hydrogen there are available butyric, pentanoic, hexanoic, heptanoic, and octanoic acids.

For example, when one and only one of $R_3$ and $R_4$ of the $L_1$ moiety is methyl, there are available the following 2-methyl alkanoic acids: butyric, pentanoic, hexanoic, heptanoic, and octanoic.

For example, when one of $R_3$ and $R_4$ of the $L_1$ moiety is fluoro there are available the following 2-fluoro alkanoic acids: butyric, pentanoic, hexanoic, heptanoic, and octanoic.

The acids of the above general formula wherein $R_7$ is alkyl and $R_3$ and $R_4$ of the $L_1$ moiety are fluoro are conveniently prepared from the corresponding 2-oxoalkanoic acids, i.e. butyric, pentanoic, hexanoic, heptanoic, and octanoic. The transformation of these 2-oxo-alkanoic acids to the corresponding 2,2-difluoro alkanoic acids proceeds by methods known in the art, using known ketonic fluorinating reagents. For example, $MoF_6 \cdot Bf_3$ is advantageously employed in the fluorination.

When $R_7$ is 1-butenyl, the formula XXII compound is prepared from the formula XXI compound by transformation of the formula XXI $2\beta$-carboxaldehyde to a corresponding $2\beta$-(2-formyl-trans-1-ethenyl) compound followed by a Grignard reaction employing the reagent prepared from

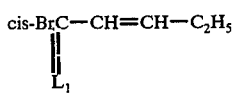

Thereupon the (3RS)-3-hydroxy compound corresponding to formula XXII is prepared, which is oxidized to the formula XXII compound with the Collins reagent. Accordingly, following the procedure of Japanese Application Number 0018-459, $3\alpha$-benzoyloxy-$5\alpha$-hydroxy-$2\beta$-carboxaldehyde-$1\alpha$-cyclopentaneacetic acid $\gamma$-lactone is transformed to benzoyloxy-$5\alpha$-hydroxy-$2\beta$-(2-formyl-trans-1-ethenyl)-$1\alpha$-cyclopentane acid $\gamma$-lactone. This product is then reacted with the Grignard reagent described above and oxidized as above.

The formula XXIII compound is prepared from the formula XXII compound by dihalogenation, followed by dehydrohalogenation. The halogenation proceeds by methods known in the art, conveniently by reaction of the formula XXII compound with a reagent such as N-halosuccinimide. The reaction proceeds slowly to completion, ordinarily within 3 to 10 days. Alternatively the molecular form of the halide $(Hal)_2$ in a diluent (e.g., carbon tetrachloride or a mixture of acetic acid and sodium acetate) is employed in this dihalogenation. Therefore dehydrohalogenation proceeds by addition of an organic base, preferably amine base, to the halide. For example pyridine, or a diazobicycloalkene, is an especially useful amine base, although non-amine bases such as methanolic sodium acetate are likewise employed.

Optionally the formula XXIII compound is prepared directly from the formula XXI compound using a Wittig reagent derived from a 1-halophosphonate corresponding to the phosphonate described above for the preparation of the formula XXII compound. These phosphonates are known in the art or are readily prepared by methods known in the art. For example, a phosphonate as described above is transformed to the corresponding 1-halophosphonate by dripping the molecular halogen into a solution of the phosphonate and a strong organic base, e.g., sodium methoxide. In any event, the 14-chloro intermediates are preferred formula XXIII products, in that they lead to PG intermediates which are more easily dehydrohalogenated at C-13 and C-14 according to the procedure of Chart R.

The 1-halophosphonate as prepared above is then reacted with the formula XXI compound in a manner described for the preparation of the formula XXII compound from the formula XXI compound to prepare the formula XXIII compound.

In each of the above described methods for the preparation of the formula XXIII compound the desired formula XXIII product is often contaminated with its corresponding cis isomer. In performing the below steps it is particularly desirable to obtain pure formula XXIII product in order to avoid creation of complicated mixtures of steroisomers. Accordingly, the formula XXIII compound is subjected to conventional separation techniques (e.g. silica gel chromatography) to obtain a pure product.

The formula XXIV compound is prepared from the formula XXIII 3-oxo bicyclic lactone by transformation of the 3-oxo-moiety to the $M_5$ moiety.

The above 3-oxo bicyclic lactone is transformed to the corresponding $3\alpha$ or $3\beta$-hydroxy bicyclic lactone, wherein $M_5$ is

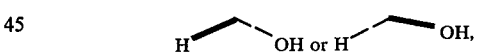

by reduction of the 3-oxo moiety, followed by separation of the $3\alpha$- and $3\beta$-hydroxy epimers. For this reduction the known ketonic carbonyl reducing agents which do not reduce ester or acid groups or carbon-carbon double bonds (when such reduction is undesirable) are employed. Examples of these agents are the metal borohydrides, especially sodium, potassium, and zinc borohydrides, lithium(tri-tert-butoxy)-aluminum hydride, metal trialkyl borohydrides, e.g. sodium trimethoxy borohydride, lithium borohydride, and the like. In those cases in which carbon-carbon double bond reduction need not be avoided, the boranes, e.g. disiamylborane (bis-3-methyl-2-butyl borane) are alternatively employed.

For the production of C-15 epimerically pure prostaglandins, the 15-epi compound is separated from the mixture by methods known in the art. For example, silica gel chromatography is advantageously employed.

For the transformation of the 3-oxo bicyclic lactone to the corresponding 3-methoxy bicyclic lactone, the 3-hydroxy moiety of the 3-hydroxy bicyclic lactone prepared above is alkylated, employing methods known in the art.

The alkylation described in the above paragraph proceeds, for example, by reaction of the 3-hydroxy bicyclic lactone with diazomethane, preferably in the presence of a Lewis acid (e.g., boron trifluoride etherate, aluminum chloride, or fluoboric acid). See for reference Fieser, et al., "Reagents for Organic Synthesis," John Wiley and Sons, New York, N. Y., (1967), especially page 191. The reaction is carried out by mixing a solution of the diazomethane in a suitable inert diluent, preferably diethyl ether, with the 3-hydroxy bicyclic lactone prepared above. This reaction proceeds at about 25° C.

An alternate method for the alkylation of the 3-hydroxy compound is by reaction with methanol in the presence of boron trifluoride etherate. Thus, the methanol and boron trifluoride etherate are reacted with the 3-hydroxy compound at 25° C., the reaction being monitored conveniently by thin layer chromatography (TLC).

The 3-oxo bicyclic lactone is transformed into the corresponding (3RS)-3-methyl bicyclic lactone wherein $M_5$ is a mixture of

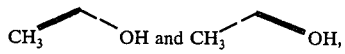

by reaction of the 3-oxo bicyclic lactone with a Grignard reagent, $CH_3MgHal$, wherein Hal is chloro, bromo, or iodo. The Grignard complex is thereafter hydrolyzed, for example, using saturated aqueous ammonium chloride as is known in the art. An alternate method for transforming the 3-oxo compound to a 3(RS)-3-methyl compound is by reaction of the 3-oxo bicyclic lactone with trimethylaluminum.

The preferred method for separation of these (3RS)-3-methyl epimers is by separation of the corresponding C-15 epimers of the PG-type, methyl esters using silica gel chromatography or high pressure liquid chromatography (HPLC). The formula XXV compound is prepared from the formula XXIV compound by deacylation, as described above. The formula XXVI compound is then prepared from the formula XXV compound by replacing any free hydroxy moieties with blocking groups according to $R_{10}$ by the procedure described above. The formula XXVII compound is then prepared from the formula XXVI compound by reduction of the formula XXVI lactone to a lactol. Methods known in the art are employed. For example, diisobutylaluminium hydride is employed at $-60°$ to $-70°$ C.

Chart B provides a method whereby the formula XXXI lactol, prepared according to Chart A, is transformed into a corresponding formula XXXV 3-oxa-14-halo-$PGF_{1\alpha}$-type compound.

The formula XXXII compound is obtained from the formula XXXI lactol by the Wittig reaction, with an (alkoxymethylene)triphenyl phosphorane, $R_{22}OOC—CH=P(C_6H_5)_3$, wherein $R_{22}$ is as defined above. The reaction is conveniently carried out at 25° C. using methods and reactants known in the art.

The formula XXXIII compound is then obtained by reduction of the ethylenic group in the carboxyl-containing side chain. For this purpose a reducing agent is used which does not reduce the Y group, for example hydrogen in the presence of a catalyst such as tris(triphenylphosphine)rhodium (I) chloride. Mild conditions are sufficient such as a pressure of 1–3 atmospheres and temperatures of 0° to 40° C.

The formula XXXIV alcohol is obtained from the formula XXXIII compound by reduction, for example with lithium aluminum hydride or lithium trimethoxy aluminum hydride. A solvent such as diethyl ether or tetrahydrofuran is conveniently used.

The formula XXXV compound is obtained by a Williamson synthesis, condensing the formula XXXIV alcohol with a haloalkanoate, $Hal—(CH_2)_g—COOR_1$, wherein Hal is chloro, bromo, or iodo and g and $R_1$ as above defined, in the presence of a base. For the base, there is used, for example, n-butyllithium, phenyllithium, triphenylmethyllithium, sodium hydride, of potassium t-butoxide. It is preferred that only one molecular equivalent of the base be used. The alkanoate is employed in about 100% stoichoimetric excess. Instead of a haloalkanoic acid ester, a salt, for example lithium chloroacetate is useful. After the condensation, the salt of transformed to the XXXV compound by methods known in the art. The condensation is conveniently run is a solvent such as dimethyl formamide, tetrahydrofuran, dimethyl sulfoxide, or hexamethylphosphoramide.

With respect to Chart C a method is provided whereby the formula XLl lactol is transformed into the corresponding formula XLlll 5-oxa-14-halo-$PGF_{1\alpha}$-type compound. The formula XLll alcohol is obtained upon reduction of the formula XLl lactol, for example, with aqueous methanolic or ethanolic sodium borohydride. Alternatively, and preferably, the formula XLll compound is obtained by a one step reduction of the formula XXVl lactone, for example, with lithium aluminum hydride or diisobutyl aluminum hydride at a temperature ranging from 0° to 35° C. For preparing the formula XLlll compound a Williamson synthesis is employed. For example, the formula XLll compound is condensed with a haloalkanoate within the scope of

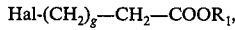

wherein Hal is chloro, bromo, or iodo and g is as defined above. Normally the reaction is done in the presence of a base such as n-butyllithium, phenyllithium, trimethylithium, sodium hydride, or potassium t-butoxide.

Alternatively and preferably, an ortho-4-bromoalkanoate is employed. Such reagents are available or are prepared by methods known in the art, for example, from the appropriate halonitrile by way of the corresponding imino ester hydrohalide as illustrated hereinafter.

The condensation is conveniently run in a solvent, such as tetrahydrofuran or dimethyl sulfoxide or especially if an organolithium compound is employed, preferably in dimethylformamide or hexamethylphosphoramide. The reaction proceeds smoothly at $-20°$ to 50° C., but is preferably performed at ambient temperature. Following the condensation the formula XLlll compound is obtained by methods known in the art, for example, by hydrolysis in cold dilute mineral acid.

Chart D provides a method whereby the formula Ll compound is transformed into the corresponding formula LVlll 4-oxa-14-halo-$PGF_{1\alpha}$-type compound or formula LIX cis-4,5-didehydro-14-halo-$PGF_{1\alpha}$-type compound.

The formula Ll compound undergoes condensation to form the formula Lll enol. For this purpose a hydrocarbyloxy, and preferably an alkoxymethylenetriphenylphosphorane is useful. See for reference, Levine, Journal of the American Chemical Society 80, 6150 (1958). The reagent is conveniently prepared from a corresponding quaternary phosphonium halide in a base, e.g. butyllithium or phenyllithium, at low temperature, e.g. preferably below $-10°$ C. The formula Ll lactol is mixed with the above reagent and the condensation proceeds smoothly within the temperature range of $-50°$ C.$-+30°$ C. At higher temperatures the reagent is unstable, whereas at low temperatures the rate of condensation is undesirably slow. Examples of alkoxymethylenetriphenylphosphoranes preferred for the above purposes are methoxy-, ethoxy-, propoxy-, isopropoxy-, butoxy-, isobutoxy-, s-butoxy-, and t-butoxymethylenetriphenylphosphorane. Various hydrocarbyloxy-methylenetriphenylphosphoranes which are optionally substituted for the alkoxymethylenetriphenylphosphoranes and are accordingly useful for preparing the formula Lll intermediates wherein $R_{26}$ is hydrocarbyl, include alkoxy-, aralkoxy-, cycloalkoxy-, and aryloxymethylenetriphenyl-phosphoranes. Examples of these hydrocarbyloxytriphenyl-phosphoranes are 2-methyl butyloxy-, isopentyloxy-, heptyl-oxy-, octyloxy-, nonyloxy-, tridecyloxy-, octadecyloxy-, benzyloxy-, phenethyloxy-, p-methylphenethyloxy-, 1-methyl-3-phenylpropyloxy-, cyclohexyloxy-, phenoxy-, and p-methylphenoxy-, phenoxymethylenetriphenylphosphorane. See for reference, Organic Reactions, Vol. 14, pg. 346-348, John Wiley and Sons, New York, N.Y. (1965). The formula Lll enol intermediates are then hydrolyzed to the formula Llll lactols. This hydrolysis is done under acidic conditions for example with perchloric acid or acetic acid. Tetrahydrofuran is a suitable diluent for this reaction mixture. Reaction temperatures of from 10° to 100° C. are employed. The length of time required for hydrolysis is determined in part by the hydrolysis temperature and using acetic acid-water-tetrahydrofuran at about 60° C. several hr. are sufficient to accomplish the hydrolysis.

The formula LIV compound is then prepared from the formula Llll compound by oxidation of the formula Llll lactol to a lactone. This transformation is carried out, using for example, silver oxide as an oxidizing reagent, followed by treatment with pyridine hydrochloride.

The formula LIV lactone may then be converted to the formula LV ether by transformation of any free hydroxy moieties to blocking groups, according to $R_{10}$, following the procedure herein described for these transformations.

Thereafter the formula LVI compound is prepared from the formula LV compound by reduction of the formula LV lactone to a lactol. For example, diisobutylaluminum hydride is employed as is described above for the reduction of lactones to lactols. The formula LVl lactols so prepared are then used alternatively for the preparation of the formula LVlll or LIX compound.

In the preparation of the formula LVIII compound, the formula LVl lactol is first transformed into the formula LVll compound by reduction of the formula LVl lactol. The formula LVll compound is then transformed into the corresponding formula LVIII compound by a Williamson synthesis. Methods and corresponding reagents employed in the transformation of the formula LVl compound to the formula LVll and thereafter the transformation of the formula LVll compound to the formula LVIII compound are analogous to methods described hereinabove for the transformation of the formula XCl compound to the formula XCll compound and thereafter the transformation of the formula XCll compound to the formula XClll compound.

Accordingly, the formula LVlll 4-oxa-PGF$_{1\alpha}$-type compound is prepared.

The formula LIX compound is prepared from the formula LVl compound by a Wittig alkylation, using the appropriate ($\omega$-carboxyalkyl)triphenylphosphonium bromide, HOOC-CH$_2$-(CH$_2$)$_h$-CH$_2$-P-(C$_6$H$_5$)$_3$, wherein $h$ is as defined above. The reaction proceeds as is generally known in the art, by first mixing the appropriate ($\omega$-carboxyalkyl)triphenylphosphonium bromide with sodio dimethyl sulfinylcarbanide, at ambient temperature, and adding the formula LVl lactol to this mixture. Thereafter the carboxy hydrogen of the compound so formed is transformed to an $R_1$ moiety by the methods and procedures hereinbelow described. Accordingly, there is prepared the formula LIX cis-4,5-didehydro-PGF$_{1\alpha}$-type compound.

Chart E provides a method whereby the formula LXI compound is transformed to the corresponding formula LXll 14halo-PGF$_{2\alpha}$-or 11-deoxy-14-halo-PGF$_{2\alpha}$-type compound or formula LXlll 14-halo-PGF$_{1\alpha}$- or 11-deoxy-14-halo-PGF$_{1\alpha}$-type compound.

The formula LXII compound is prepared from the formula LXl compound using the appropriate ($\omega$-carboxyalkyl)triphenylphosphonium bromide, HOOC—(CH$_2$)$_g$—CH$_2$—P—(C$_6$H$_5$)$_3$Br, as is described above followed by transformation of the carboxy hydrogen to an $R_1$ moiety as described below. The formula LXlll compound is then prepared from the formula LXll compound by catalytic hydrogenation of the cis-5,6-double bond. Hydrogenation methods known in the art are employed, e.g., the use of metal catalysts under a hydrogen atmosphere. The reaction here is terminated when one equivalent of hydrogen is absorbed per equivalent of prostaglandin-type compound. Mixtures of compounds thereby produced are conveniently separated by silica gel chromatography.

Chart F provides a method whereby the prostaglandin-type intermediates of Charles B, C, C, and E are transformed to the corresponding 14-halo-PGF, 11-dieoxy-14-halo-PGF, 14-halo-PGE, 11-deoxy-14-halo-PGE, 14-halo-PGA, or 14-halo-PGB compounds.

The formula LXXI compound is as prepared above. The formula LXXII PGE-type compound is prepared from the formula LXXI compound by oxidation methods known in the art. For example, the Jones reagent is advantageously employed herein. The formula LXXIII compound is then prepared from the formula LXXI compound or the formula LXXII compound by hydrolysis of any blocking groups. Such hydrolysis proceeds by moixing the reactant with, for example, water, tetrahydrofuran, and acetic acid as described above.

The formula LXXIV compound is then prepared from the formula LXXIII compound by transformation of the $R_1$ moiety of the formula LXXXIII compound to its methyl ester. Methods hereinbelow described are emplpoyed. The C-15 epimers are then separated, thereby preparing the formula LXXV compound.

The formula LXXVI compound, which is represented by formula LXXIII when the M$_5$ moiety consists of separated C-15 epimers, is prepared optionally from the formula LXXV compound by transformation of the carboxy methyl ester of formula LXXV compound to an $R_1$ moiety as described above.

The formula LXXVII compound is prepared from the formula LXXVI compound wherein $M_{18}$ is =O by a ring carbonyl reduction. Methods hereinbelow described are employed. The formula LXXVIII and formula LXXIX compounds are prepared from the formula LXXVI wherein $M_{18}$ is

employing an acidic or basic dehydration respectively. Methods described below for these acidic or basic dehydrations are employed.

The formula LXXVIII compound is optionally prepared from the formula LXXVI compound wherein $R_8$ is hydroxy by acetylation with acetic anhydride, thereby preparing a highly unstable corresponding PGE-type 11,15-diacetate, followed by silica gel chromatography. The PGE-type 11,15-diacetate thereby spontaneously decomposes to the corresponding PGA-type 15-acetate, which is hydrolysed to yield the formula LXXVIII PGA-type product. Optionally, however, the 11,15-diacetate may be allowed to stand at room temperature whereby spontaneous decomposition will ordinarily be effected within one to five days.

The above acidic dehydrations are carried out by methods known in the art for acidic dehydrations of known prostanoic acid derivatives. See for reference Pike, et al., Proceedings of the Nobel Symposium II, Stockholm (1966), Interscience Publishers, New York, pg. 162-163 (1967); and British Specification No. 1,097,533. Alkanoic acids of 2 to 6 carbon atoms, inclusive, preferentially acetic acid, are employed in this acidic dehydration. Dilute aqueous solutions of mineral acids e.g. hydrochloric acid, especially in the presence of a solubilizing diluent, e.g. tetrahydrofuran, are also useful as reagents for this acidic dehydration. Use, however, of mineral acids as described above may cause partial hydrolysis of the carboxy ester of the formula LXXVI PGE reactant.

The above basic hydrations or double bond migrations (i.e., conversion of the PGA-type compound to the PGB-type compound are carried out by methods known in the art for dehydration or double bond migration of known prostanoic acid derivatives. See for reference Bergstrom, et al., Journal of Biological Chemistry 238, 3555 (1963). Bases employed are any of those whose aqueous solution has pH greater than 10. Preferred bases are the alkali metal hydroxides. A mixture of water and sufficient quantity of a water miscible alkanol to yield a homogeneous reaction mixture is suitable as a reaction medium. The reactant is then maintained in such reaction medium until the starting material is completely reacted, as shown by the characteristic ultraviolet absorption of the PGB-type compound at 278 mμ.

In the employment of the processes above when C-15 tertiary alcohols are to be prepared ($R_5$ methyl) the use of blocking groups is not required. Accordingly, in the steps of the above charts the introduction and hydrolysis of blocking groups are thereby omitted by the preferred process.

Certain (3RS)-3-methyl lactones of chart A may be separated into their respective (3S) or (3R)- epimers by silica gel chromatographic separation techniques. Where such separation is possible, this route is preferred. Accordingly, in these cases the separation is effected and $M_5$ is

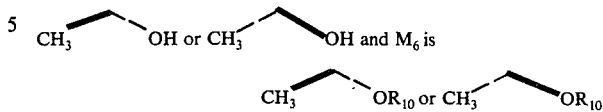

wherein $R_{10}$ is a blocking group. Accordingly, the separation procedure described in Chart F (formula LXIII - LXXV) is omitted when the optional lactone separation is employed.

When a cis-4,5-didehydro-14-halo-$PGF_{1\alpha}$ or cis-4,5-didehydro-11-deoxy-14-halo-$PGF_{1\alpha}$-type compound is to be prepared by the procedure of Chart D, the Wittig alkylation step LVI to LIX may be performed on the formula LIII lactol, instead of the formula LVI lactol, thereby eliminating the oxidation, etherification, and reduction steps of Chart D (LIII through LVI).

Charts G, H, I, and J provide methods whereby 3-oxa-3,7-inter-m-phenylene-4,5,6-trinor- or 3,7-inter-m-phenylene-4,5,6-trinor-PG-type intermediates are prepared. With respect to Charts G and H, $R_7$ is preferred to be —$(CH_2)_m$—$CH_3$, or

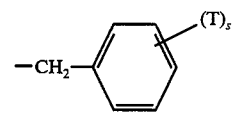

wherein m, T, and s are as defined above. In Charts I or J a method is provided for preparing those novel compounds of this specification wherein $R_7$ is preferably cis—CH=CH—$CH_2$—$CH_3$, or

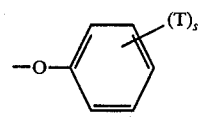

wherein T and s are as defined above, respectively. Accordingly the Charts G-J provide methods whereby intermediates useful in producing all inter-m-phenylene-PG-type compounds are prepared.

In Chart G both endo and exo forms of bicyclo hexene LXXXI are available or are made by methods known in the art, in either their racemic or enantiomerically pure forms. See U.S. Pat. No. 3,711,515. Either the endo or exo starting material will yield the ultimate intermediates of formula XCIII compound by the process of Chart G.

Oxetane LXXII is obtained by reaction of the formula LXXXI bicyclo hexene with an aldehyde of the formula

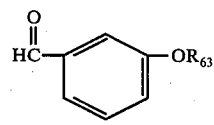

wherein $R_{63}$ is carboxyacyl of the formula

wherein $R_{64}$ is hydrogen, alkyl of one to 19 carbon atoms, inclusive, or aralkyl of 7 to 12 carbon atoms, inclusive, wherein alkyl or aralkyl are substituted with zero to 3 halo atoms.

The above benzyl aldehydes are available or readily prepared by methods known in the art. Examples of such compounds within this scope are:

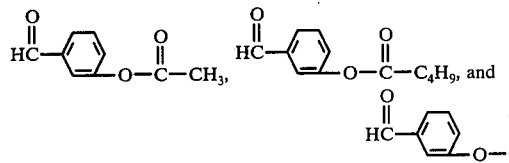

The formation of oxetane LXXXII is accomplished by photolysis of a mixture of the bicyclo hexene and the aldehyde in a solvent. The bicyclo hexene is preferably used in excess over the molar equivalent, for example 2 to 4 times the stoichiometric equivalent amount. The solvent is a photochemically inert organic liquid, for example liquid hydrocarbons, including benzene or hexane, 1,4-dioxane, and diethyl ether. The reaction is conveniently run at ambient conditions, for example 25° C., but may be done over a wide range of temperature, from about −78° C. to the boiling point of the solvent. The irradiation is done with mercury vapor lamps of the low or medum pressure type, for example those peaking at 3500 Å. Such sources are available from The Southern New England Ultraviolet Co., Middletown, Conn. Alternatively, those lamps which emit a broad spectrum of wavelengths and which may be filtered to transmit only light of ∼3000–3700 Å may also be used. For a review of photoysis see D. R. Arnold in "Advances in Photochemistry", Vol. 6, W. A. Noyes et al., Wiley-interscience, New York, 1968, pp. 301–423.

The cleavage of the oxetane ring to yield the formula LXXXIII compound from the formula LXXXII compound is accomplished with an alkali metal in the presence of a primary amine or a alcohol. Preferred is lithium in ethylamine, or sodium in ethyl alcohol. See L. J. Altman et al., Synthesis 129 (1974). The cleavage transformation may also be accomplished by catalytic hydrogenation over an inert metal catalyst, e.g. Pd on carbon, in ethyl acetate or ethanol.

The formula LXXIV compound is prepared from the formula LXXXIII diol by preferably blocking the two hydroxyl groups with carboxyacyl groups according to $R_{63}$, i.e.

as defined above. For example, the diol is treated with an acid anhydride such as acetic anhydride, or with an acyl halide in a tertiary amine. Especially preferred is pivaloyl chloride in pyridine.

Other carboxyacylating agents useful for this transformation are known in the art or readily obtainable by methods known in the art, and include carboxyacyl halides, preferably chlorides, bromides, or fluorides, i.e. $R_{64}C(O)Cl$, $R_{64}C(O)Br$, or $R_{64}C(O)F$, and carboxy acid anhydrides, $(R_{64}CO)_2O$, wherein $R_{64}$ is as defined above. The preferred reagent is an acid anhydride. Examples of acid anhydrides useful for this purpose are acetic anhydride, propionic anhydride, butyric anhydride, pentanoic anhydride, nonanoic anhydride, tridecanoic anhydride, steric anhydride, (mono, di, or tri)chloroacetic anhydride, 3-chlorovaleric anhydride, 3-(2-bromoethyl)-4,8-dimethylnonanoic anhydride, cyclopropaneacetic anhydride, 3-cycloheptanepropionic anhydride, 13-cyclopentanetridecanoic anhydride, phenylacetic anhydride, (2 or 3)-phenylpropionic anhydride, 13-phenyltridecanoic anhydride, phenoxyacetic anhydride, benzoic anhydride, (o, m, or p)-bromobenzoic anhydride, 2,4 (or 3,4)-dichlorobenzoic anhydride, p-trifluoromethylbenbenzoic anhydride, 2-chloro-3-nitrobenzoic anhydride, (o, m, or p)-nitrobenzoic anhydride, (o, m, or p)-toluic anhydride, 4-methyl-3-nitrobenzoic anhydride, 4-octylbenzoic anhydride, (2,3, or 5)-biphenylcarboxylic anhydride, 3-chloro-4-biphenylcarboxylic anhydride, 5-isopropyl-6-nitro-3-biphenylcarboxylic anhydride, and (1 or 2)-naphthoic anhydride. The choice of anhydride depends upon the identity of $R_{64}$ in the final acylated product, for example when $R_{64}$ is to be methyl, acetic anhydride is used; when $R_{64}$ is to be 2-chlorobutyl, 3-chlorovaleric anhydride is used.

When $R_{64}$ is hydrogen,

is formyl. Formylation is carried out by procedures known in the art, for example, by reaction of the hydroxy compound with the mixed anhydride of acetic and formic acids or with formylimidazole. See, for example, Fieser et al., Reagents for Organic Synthesis, John Wiley and Sons, Inc., pp. 4 and 407 (1967) and references cited therein. Alternatively, the formula LXXXIII diol is reacted with two equivalents of sodium hydride and then with excess ethyl formate.

In formula LXXXIV, $R_{68}$ may also represent a blocking group including benzoyl, substituted benzoyl, mono-esterified phthaloyl and substituted or unsubstituted naphthoyl. For introducing those blocking groups, methods known in the art are used. Thus, an aromatic acid of the formula $R_{63}OH$, wherein $R_{63}$ is as defined above, for example benzoic acid, is reacted with the formula LXXXIII compound in the presence of a dehydrating agent, e.g. sulfuric acid, zinc chloride, or phosphoryl chloride; or an anhydride of the aromatic acid of the formula $(R_{64}CO)_2O$, for example benzoic anhydride, is used.

Preferably, however, an acyl halide, e.g. $R_{63}Cl$, for example benzoyl chloride, is reacted with the formula LXXXIII compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene, or chloroform. The acylating agent is used either in stoichiometric amount or in excess.

As examples of reagents providing $R_{63}$ for the purposes of this invention, see the discussion above pertaining to the use of acyl protecting groups.

The formula LXXXIV acetal is converted to aldehyde LXXXV by acid hydrolysis, known in the art, using dilute mineral acids, acetic or formic acids, and the like. Solvents such as acetone, dioxane, and tetrahydrofuran are used.

For the conversion of LXXXV to LXXXIX, it is optional whether $R_{66}$ be hydrogen or a "blocking group" as defined below. For efficient utilization of the Wittig reagent it is preferred that $R_{66}$ be a blocking group. If the formula LXXXIV compound is used wherein $R_{68}$ is hydrogen, the formula LXXXV intermediate will have hydrogen at $R_{66}$. If $R_{66}$ is to be a blocking group, that may be readily provided prior to conversion of LXXXV to LXXXVI by reaction with suitable reagents as discussed below.

The blocking group, $R_{65}$, is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., J. Am. Chem. Soc. 93, 1491 (1971)).

Those which have been found useful include (a) carboxyacyl within the scope of $R_{63}$ above, i.e. acetyl, and also benzoyl, naphthoyl, and the like; (b) blocking groups according to $R_{10}$; and (c) -Si($G_1$)$_3$ wherein $G_1$ is as defined above.

In replacing the hydrogen atoms of the hydroxyl groups with a carboxyacyl blocking group, methods known in the art are used. The reagents and conditions are discussed above for $R_{68}$ on the compound of formula LXXXIV.

When the blocking group is according to $R_{10}$ appropriate reagents and conditions are as defined above.

When the blocking group is silyl of the formula -Si($G_1$)$_3$, the formula LXXXIV compound is transformed to a silyl derivative of formula LXXXV by procedures known in the art. See, for example, Pierce, "Silylation of Organic Compounds," Pierce Chemical Co., Rockford, Illinois (1968). The necessary silylating agents for these transformations are known in the art or are prepared by methods known in the art. See, for example, Post "Silicones and Other Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternatively, a chlorosilane is used with a corresponding disilazane. Examples of other silylating agents suitable for forming the formula LXXXV intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

In transforming the formula LXXXV compound to the formula LXXXVI compound the aldehyde group is transformed by the Wittig reaction to a moiety of the formula

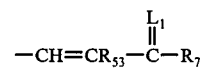

For this purpose a phosphonium salt prepared from an organic chloride or bromide of the formula

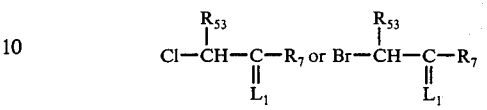

is employed, wherein $L_1$, $R_7$, and $R_{53}$ are as defined above. These organic chlorides or bromides are known in the art or are readily prepared by methods known in the art. See for example the above-identified German Offenlegungsschrift No. 2,209,990. As to the Wittig reaction, see, for example, U.S. Pat. No. 3,776,941 and references cited therein.

The formula LXXXVII compound is obtained by deblocking if necessary. When $R_{66}$ is a hindered carboxyacyl, $R_{66}$ on the phenolic hydroxy is selectively replaced with hydrogen by hydrolysis with sodium or potassium hydroxide in ethanol-water. Instead of ethanol, other water-miscible solvents may be substituted, for example 1,4-dioxane, tetrahydrofuran, or 1,2-dimethoxyethane. The selective hydrolysis is preferably carried out at −15° to 25° C. Higher temperatures may be used but with some decrease in selectivity.

Total hydrolysis of $R_{66}$ blocking groups on the formula LXXXVI compound is accomplished, when $R_{66}$ is carboxyacyl, with an alkali alkoxide in an alcoholic solvent preferably sodium methoxide in methanol at a temperature from 25° C. to 50° C. When $R_{66}$ is trialkylsilyl, either aqueous acid or base are used at 25° to 50° C.

Continuing with Chart G, a Williamson synthesis is employed to obtain the formula LXXXVIII compound. The formula LXXXVII phenol is condensed with a haloalkanoate within the scope of Hal—(CH$_2$)$_g$—COOR$_1$ wherein Hal is chloro, bromo, or iodo and g and $R_1$ are as defined above. Normally the reaction is done in the presence of a base such as n-butyllithium, phenyllithium, triphenylmethyllithium, sodium hydride, potassium t-butoxide, sodium hydroxide, or potassium hydroxide.

The transformation of the formula LXXXVIII compound to the formula LXXXIX is accomplished by any one of several routes known in the art. See U.S. Pat. No. 3,711,515. Thus, the alkene LXXXVIII is hydroxylated to glycol LXXXIX. For this purpose osmium tetroxide is a suitable reagent, for example in conjunction with N-methylmorpholine oxide-hydrogen peroxide complex (see Fieser et al., "Reagents for Organic Synthesis", p. 690, John Wiley and Sons, Inc., New York (1967)). Thereafter, several methods are available for obtaining the formula XC product. In one method the glycol is converted to a bis(alkanesulfonic acid) ester and subsequently hydrolyzed to the formula XC compound by methods known in the art (See, for example German Offenlegungsschrift No. 1,936,676, Derwent Farmdoc No. 6862R). Another method is by way of a diformate by formolysis of the glycol (see U.S. Pat. No. 3,711,515).

Still another method is by way of a cyclic ortho ester. For this purpose, glycol LXXXIX is reacted with an ortho ester of the formula

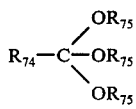

wherein $R_{74}$ is hydrogen, alkyl of one to 19 carbon atoms, inclusive, or aralkyl of 7 to 12 carbon atoms, inclusive, substituted with zero to 3 halo atoms; and $R_{75}$ is methyl or ethyl. There is then formed a cyclic orthoester of the formula

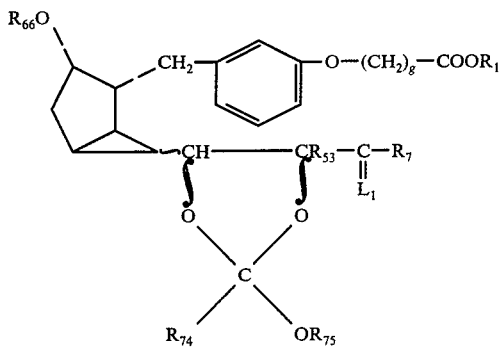

wherein g, $R_1$, $R_{53}$, $R_{66}$, $R_{74}$, $R_{75}$, $L_1$ and $R_7$ are as defined above. The reaction goes smoothly in a temperature range of $-50°$ C. to $+100°$ C., although for convenience 0° C. to $+50°$ C. is generally preferred. From 1.5 to 10 molar equivalents of the ortho ester are employed, together with an acid catalyst. The amount of the catalyst is usually a small fraction of the weight of the glycol, e.g., about 1%, and typical catalysts include pyridine hydrochloride, formic acid, hydrogen chloride, p-toluenesulfonic acid, trichloroacetic acid, or trifluoroacetic acid. The reaction is preferably run in a solvent, for example benzene, dichloromethane, ethylacetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:

trimethyl orthoformate,
triethyl orthoacetate,
triethyl orthopropionate,
trimethyl orthobutyrate,
trimethyl orthovalerate,
trimethyl orthooctanoate,
trimethyl orthophenylacetate, and
trimethyl ortho (2,4-dichlorophenyl)acetate.

Preferred are those ortho esters wherein $R_{74}$ is alkyl of one to 7 carbon atoms; especially preferred are those wherein $R_{74}$ is alkyl of one to 4 carbon atoms.

Next, the cyclic orthoester depicted above is reacted with anhydrous formic acid to yield a diol diester of the formula

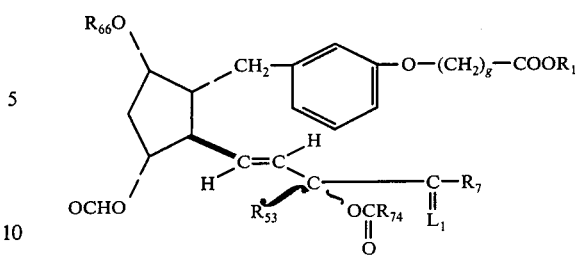

wherein g, $R_1$, $R_7$, $R_{53}$, $R_{66}$, and $L_1$ are as defined above.

Anhydrous formic acid refers to formic acid containing not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl orthoesters, for example trimethyl orthoformate, which are useful as drying agents for the formic acid. Although the reaction proceeds over a wide range of temperatures, it is conveniently run at about 20°–30° C. and is usually completed within about 10 minutes.

Finally, the diol diester above is converted to product XC by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from $-50°$ C. to 100° C. The time for completion of the reaction varies with the nature of $R_{74}$ and the base, proceeding in the case of alkali carbonates in a few minutes when $R_{74}$ is hydrogen but taking up to several hours when $R_{74}$ is ethyl, for example.

When the solvolysis proceeds too long or when conditions are too severe, an ester group ($R_1$) is often removed. They are, however, readily replaced by methods known in the art. See the discussion below.

The formula XCI compound is prepared from the formula XC compound by oxidation of the C-15 hydroxy to a 15-oxo. Accordingly, as is known in the art, 2,3-dichloro-5,6-dicyano-1,4-benzoquinone, activated manganese dioxide, or nickel peroxide (See Fieser, et al., "Reagents for Organic Synthesis", John Wiley and Sons, New York, N.Y., pgs. 215, 637, and 731) is advantageously employed. Thereafter, the formula XCI compound is prepared from the 15-oxo compound by transforming the C-9 and C-11 hydroxy hydrogens to $R_{65}$ blocking groups. Procedures known in the art are employed. See for reference Pierce, "Silylation of Organic Compounds," Pierce Chemical Company, Rockford, Ill. (1968) and the discussion above pertaining to the intorduction of blocking groups according to $R_{10}$. The necessary silylating reagents for these transformations are known in the art or are prepared by methods known in the art. See for reference, Post, "Silicones and Other Silicone compounds," Reinhold Publishing Corp., New York, N.Y. (1949).

The formula XCII compound is then prepared from the formula XCI compound by the procedure described in Chart A for transforming the formula XXII compound to the formula XXIV compound, followed by hydrolysis of the silyl groups, using, for example, dilute aqueous acetic acid in a water miscible solvent, such as ethanol (sufficient to yield a homogeneous reaction mixture). At 25° C., the hydrolysis is ordinarily complete in 2 to 12 hrs. Further, the hydrolysis preferably carried out in an inert atmosphere, e.g., nitrogen or argon.

The formula XCIII compound is prepared from the formula XCII compound by separation of the 15-methyl epimers when present. Such separation proceeds by methods discussed above for accomplishment of this purpose (e.g., thin layer chromatography or high pressure liquid chromatography).

Referring to Chart H, there are shown process steps by which the formual XCVI bicyclo hexene is transformed first to an oxetane (formula XCVII) with a fully developed side chain, e.g.,

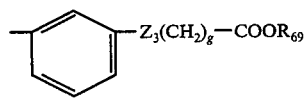

wherein $Z_3$ is oxa or methylene, and ultimately to the formula CIV compound.

In transforming XCVI and XCVII in Chart H, there is employed an aldehyde of the formula

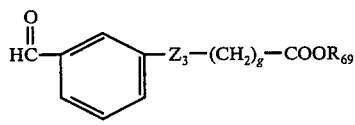

wherein $Z_3$ and $R_{69}$ are as defined above. Such aldehydes are available or are readily prepared by methods known in the art, e.g.,

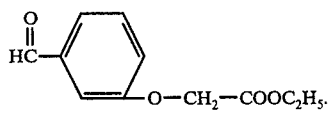

The conditions for this transformation are essentially the same as for the corresponding step of Chart G (i.e., LXXXI to LXXXII). Thereafter, the preparation of the formula CI compound proceeds by methods analogous and by employing the same conditions as the corresponding steps of Chart G (i.e., LXXXII to LXXXVI).

The steps transforming CI to CIV then proceed in similar fashion, employing the same or similar reagents and conditions as the corresponding steps of Chart G discussed above.

Referring next to Chart I the process steps are shown whereby aldehyde CVI prepared in Chart H is transformed to a 17,18-tetradehydro-PG intermediate (formula CIX) and 17,18-didehydro-PG intermediate (formula CX).

In Chart I, a Wittig reagent is employed which is prepared from a phosphonium salt of a haloalkyne of the formula

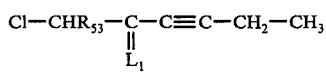

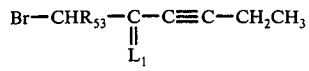

wherein $R_{53}$ and $L_1$ are as defined above, (See, for example, U. Axen et al., Chem. Comm. 1969, 303, and ibid. 1970, 602) in transforming CVI to CVII.

Thereafter, in subsequent transformations yielding the 17,18-tetradehydro compound CIX, the reagents and conditions are similar to those employed for the corresponding reactions shown in Chart H.

Transformation of the formula CIX compound to the formula CX compound is accomplished by hydrogenation of CIX using a catalyst which catalyzes hydrogenation of —C≡C— only to cis—CH═CH—, as known in the art. See, for example, Fieser et al., "Reagents for Organic Syntheses", pp. 566—567, John Wiley and Sons, Inc., New York (1967). Preferred is Lindlar catalyst in the presence of quinoline. See Axen, references cited above.

As discussed above, Chart J provides a method whereby the formula CXI PG-type intermediate, prepared according to Chart G or Chart H is transformed to the corresponding formula CXIV 16-phenoxy-PG-type intermediates.

The formula CXII compound is prepared from the formula CXI compound by cleavage of the 13,14-trans double bond, conveniently by ozonolysis. Ozonolysis proceeds by bubbling dry oxygen, containing about 3 percent ozone, through a mixture of a formula CXI compound in a suitble nonreactive diluent. For example, n-hexane is advanatageously employed. The ozone may be generated using methods known in the art. See, for example, Fieser, et al., "Reagents for Organic Synthesis," John Wiley and Sons, Inc. (1967), pages 773-777. Reaction conditions are maintained until the reaction is shown to be complete, for example, by silica gel thin layer chromatography or when the reaction mixture no longer rapidly decolorizes a dilute solution of bromine in acetic acid.

The formula CXIII compound is then prepared from the formula CXII compound employing a phosphonate of the formula:

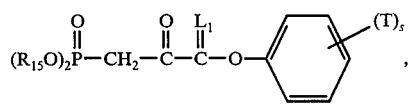

wherein $R_{15}$, $L_1$, T, and s are as defined above. Phosphonates of this general formula are prepared by methods known in the art. See the text hereinabove accompanying Chart A for discussion of the preparation and the appropriate reaction conditions by which the Wittig reaction proceeds. The formula CSIV compound is prepared from the formula CXIII compound by transformation of the 15-oxo moiety to an $M_1$ moiety. Methods hereinabove, particularly those discussed in Charts G and H above, are employed.

Optionally the method of Chart J is used to introduce the various other $R_7$ moieties to the formula CXII compound using the appropriate phosphonate.

Chart K provides a method whereby the formula CXXI bicyclic lactone aldehyde is transformed to the corresponding formula CXXIV PGF$_{2\alpha}$-type intermediate which is useful according to the procedures of Chart L in preparing the novel 13,14-didehydro-PGF$_{2\alpha}$-type compounds disclosed in this specification.

The formula CXXI compound is known in the art. This compound is available in either of its two pure enantiomeric forms or as a mixture comprising both of these enantiomers. The formula CXXII compound is prepared from the formula CXXI compound using reagents and conditions analogous to the preparation of the formula XXIII compound of Chart A from the formula XXI compound. Thus, methods generally known to the art are employed. The formula CXXIII compound is then prepared from the formula CXXII compound using reaction conditions and reagents analogous to the preparation of the formula XXXV compound from the formula XXXI compound (Chart B), the preparation of the formula XLIII compound from the formula XLI compound (Chart C),- the preparation of the formula LVIII or LIX compound from the formula LI compound (Chart D), or the preparation of the formula LXIII compound from the formula LXI compound (Chart E). Thereafter the formula CXXIV compound is prepared from the formula CXXIII compound by first hydrolyzing any blocking groups according to R$_{10}$, (using procedures and methods hereinabove described), and second separating the C-15 epimers when R$_5$ is methyl. Methods herein described (e.g., silica gel chromatography or high pressure liquid chromatography) are employed.

Further by the procedure of Chart F, the various PGF$_\alpha$- or 11-deoxy-PGF$_\alpha$-type compounds prepared according to Charts G, H, I, J, or K are transformed to corresonding PGE or 11-deoxy-PGE-, PGF$_\beta$- or 11-deoxy-PGF$_\beta$-, PGA-, or PGB-type compounds.

Chart L provides a method whereby the formula CXXXI compound (as known in the art, or as prepared herein) is transformed to the corresonding formula CXXXVI 14-halo-PGF- or 11-deoxy-PGF-type product.

The formula CXXXII compound is prepared from the formula CXXXI compound by selective oxidation of the C-15 alcohol. The oxidation is accomplished employing conventional methods known in the art, for example, the use of 2,3-dichloro-5,6-dicyanobenzoquinone, activated manganese dioxide, or nickel peroxide. See Fieser, et al. "Reagents for Organic Synthesis" John Wiley and Sons, New York, N.Y. pages 215, 637, and 731.

The formula CXXXIII compound is prepared from the formula CXXXII compound by protection of free hydroxy moieties with acyl protecting groups according to R$_9$. Methods described hereinabove for preparing these acyl derivatives are employed. Optionally, however, silyl groups within the scope of -Si(G$_1$)$_3$, wherein G$_1$ is defined above, are employed in plce of the acyl protecting groups. Finally, the acyl protection or silylation described herein is optionally omitted, particularly, where R$_5$ and R$_6$ of the M$_1$ moiety of the formula CXXXVI compound are both hydrogen.

The formula CXXXIV compound is prepared from the formula CXXXIII compound by 14-halogenation. This 14-halogenation is achieved by one of several methods known in the art. For example, following the procedure of Chart A wherein the formula XXIII compound is prepared from the formula XXII compound, formula CXXXIV compound herein is prepared. As especially useful reagent for the instant transformation is sulfuryl chloride, as described above. Mixtures of products produced are separated, using conventional techniques. The formula CXXXV compound is then prepared from the formula CXXXIV compound by transformation of the 15-oxo to an M$_1$ moiety. Techniques as described hereinabove are employed. Thereafter, the formula CXXXVI compound is prepared from the formula CXXXV compound by removal of the optionally present acyl or silyl protecting groups, following the procedures described hereinabove.

Chart M provides a method whereby the 14-halo-8$\beta$,12$\alpha$-PG-type compounds of formulas CXLVI and CXLVII are prepared from the formula CXXXVIIa or formula CXXXVIIb enantiomeric starting material, which compounds are known in the art or readily prepared by methods known in the art. With respect to Chart M, R$_{51}$ is R$_{30}$—SO$_2$—, wherein R$_{30}$ is alkyl, cycloalkyl, aralkyl, phenyl, or phenyl substituted with alkyl or halogen, but preferably methyl or p-tolyl.

By the procedure of Chart M the formula CXXXVIIa compound is transformed to the formula CXXXVIII compound by the procedure described in Chart A for the preparation of the formula XXIV compound from the formula XXI compound. Thereafter, the formula CXXXIX compound is prepared from the formula CXXXVIII compound by the method described in Chart A for the preparation of the formula XXVI compound from the formula XXV compound. Thereafter the formula CXXXIX compound is deacylated following the procedure described in Chart A for the preparation of the formula XXV compound from the formula XXIV compound. Following deacylation the formula CXLI compound prepared from the formula CXL compound by sulfonation. Thereby, the alkyl, aralkyl, cycloalkyl, phenyl or substituted phenyl sulfonyl derivative of the formula CXL compound is prepared. This sulfonation proceeds by a method analogous to the acylation, employing protecting groups according to R$_9$, described hereinabove. Thus, for example, the sulfonyl chloride, e.g., mesyl chloride (methane sulfonyl chloride) or tosyl chloride (P-toluenesulfonyl chloride) is reacted with the hydroxy containing compound in the presence of a catalytic amount of an amine base (e.g. pyridine).

Thereafter the 11$\beta$-sulfonyl moiety is transformed to an 11$\alpha$-acyl moiety employing the sodium, potassium or lithium salt of the corresponding carobxylicacid. Thus, for example when R$_9$ is benzoyl the formula CXLI sulfonyl derivative is reacted with sodium, potassium or lithium benzoate in an inert diluent (preferably, in a polar aprotic solvent) to yield the formula CXLII compound. As described above the carboxylic acids of the formula R$_9$OH are known in the art or are readily prepared by methods known in the art. Further, these acids are transformed into the sodium, potassium or lithium salts employing conventional methods.

Thereafter, the formula CXLII compound is transformed to the formula CXLIII compound by selective deacylation of the R$_9$ protecting group. Methods described hereinabove for deacylation are employed (see the transformation of the formula CXXXIX compound to the formula CXL compound).

Thereafter the formula CXLIV compound is prepared from the formula CXLIII compound by transforming the 11-hydroxy hydrogen to a blocking group by methods hereinabove described or by transformation of the formula CXXXVIIb compound employing the methods and procedures described hereinabove for the preparation of the formula XXVI compound from the formula XXI compound.

Finally following the procedure of Chart A the formula CXLIV compound is transformed to the formula CXLV compound and thereafter the formula CXLV compound (following the procedure of Charts A-F) is transformed to the formula CXLVI and formula CXLVII compounds.

Chart N provides a method whereby PGA-type compounds are transformed into corresponding 11-deoxy PGE-type compounds, according to formula CLII or CLVI.

The formula CLII compound is prepared from the formula CLI compound by selective catalytic hydrogenation of the cyclopentene ring olefinic unsaturation. This transformation is selectively effected without affecting sidechain unsaturation. For this purpose a 5 to 10 percent palladium or rhodium catalyst on carbon, alumina or other suitable support is employed. The reaction is carried out in any suitable organic solvent, e.g. ethyl acetate, methanol, ethanol, or diethyl ether at temperatures of $-30°$ to $-50°$ C. and pressures greater than or equal to the atmospheric pressure, but less than several atmospheres.

The formula CLIII compound is prepared from the formula CLI compound by replacing any free hydroxy hydrogen with a blocking group, according to $R_{31}$.

This blocking group function prevents attack on the hydroxy by subsequent reagents, especially the reagent employed herein for the transformation of the C-9 hydroxy to a C-9 oxo group. This blocking group further functions so as to be replaceable by hydrogen or a later stage in the preparation of the prostaglandin-type products. Blocking groups, according to $R_{31}$, which are useful for these purposes include alkanoyl of 2 to 12 carbon atoms, inclusive, tetrahydropyranyl, tetrahydrofuranyl, a group of the formula

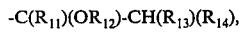
-C($R_{11}$)(O$R_{12}$)-CH($R_{13}$)($R_{14}$), wherein $R_{11}$, $R_{12}$, $R_{13}$, and $R_{14}$ are as defined above, and a silyl group of the formula -Si($G_1$)$_3$, wherein G is alkyl of one to 4 carbon atoms, inclusive, phenyl, phenyl substituted with one or 2 fluoro, chloro, or alkyl of one to 4 carbon atoms, inclusive, or aralkyl of 7 to 12 carbon atoms, inclusive.

The transformation of Chart N which involve replacing any hydroxy hydrogen with a blocking group according to $R_{31}$ employ methods known in the art. Further subsequent hydrolysis of these blocking groups according to $R_{31}$ proceeds by methods known in the art.

When the blocking group is of the formula

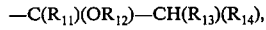
—C($R_{11}$)(O$R_{12}$)—CH($R_{13}$)($R_{14}$), wherein $R_{11}$, $R_{12}$, $R_{13}$, and $R_{14}$ are as defined above, the appropriate reagent is a vinyl ether, e.g. isobutyl vinyl ether or any vinyl ether of the formula

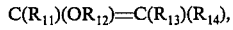
C($R_{11}$)(O$R_{12}$)=C($R_{13}$)($R_{14}$), wherein $R_{11}$, $R_{12}$, $R_{14}$ are as defined above; or an unsaturated cyclic or heterocyclic compound, e.g. 1-cyclohexen-1-yl methyl ether or 5,6-dihydro-4-methoxy-2H-pyran. See C. B. Reese, et al., Journal of the American Chemical Society 89, 3366 (1967). The reaction conditions for such vinyl ethers and unsaturates are similar to those for dihydropyran above.

The subsequent hydrolysis of these blocking groups according to $R_{31}$ proceeds by methods known in the art. Silyl groups are readily removed by prior art procedures known to be useful for transforming silyl ethers and silyl esters to alcohol and carboxylic acids, respectively. for reference see Pierce, cited above, especially page 447 thereof. A mixture of water and a sufficient quantity of a water miscible organic diluent to yield the homogeneous reaction mixture represents a suitable reaction medium. Addition of a catalytic amount of an organic or inorganic acid hastens the hydrolysis. The length of time required for hydrolysis is determined in part by temperature. With a mixture of water and methanol at 25° C. several hours is usually sufficient for hydrolysis. At 0° C., several days are required.

For the hydrolysis of the various other blocking groups according to $R_{31}$ mild acidic conditions are employed.

The formula CLIV compound is prepared from the formula CLIII compound by reduction of the formula CLIII compound with reducing agent which selectively effects reduction of the ring unsaturation and reduction of the C-9 oxo group to a C-9 hydroxy group, without reducing side chain unsaturation. For this purpose an alkali metal borohydride, e.g. sodium, potassium, or lithium borohydride is effectively employed in aqueous solution. The reaction is carried at about $-20°$ C. and is complete within a few minutes.

The formula CLV compound is prepared by oxidation of the formula CLIV compound using an oxidizing reagent, such as the Jones reagent (acidified chromic acid). See for reference Journal of the Chemical Society 39 (1946). A slight stoichiometric excess beyond the amount necessary to oxidize a single hydroxy group is employed. Acetone is a useful diluent for this purpose. Reaction temperatures at least as low as about 0° C. should be used. Preferred reaction temperatures are in the range of $-10°$ to $-50°$ C. An especially useful reagent for this purpose is the Collins reagent (chromium trioxide in pyridine). See for reference J. C. Collins, et al., Tetrahedron Letters 3363, (1968). Dichloromethane is a suitable diluent for this purpose. Reaction temperatures below 30° C. are preferred. Reaction temperatures in the range of $-10°$ to $+10°$ C. are especially preferred. This oxidation proceeds rapidly and is complete within several minutes. The formula CLV compound may then be isolated by conventional methods, e.g. silica gel chromatography.

Examples of other oxidation reagents useful for this transformation are silver carbonate on celite (Chemical Communications 1102 (1969)), mixtures of chromium trioxide in pyridine (Journal of the American Chemical Society 75, 422 (1953)), and Tetrahedron Letters, 18, 1351 (1962)), tert-butyl chromate in pyridine (Biological Chemical Journal, 84, 195 (1962)), mixtures of sulfur trioxide in pyridine and dimethyl sulfoxide (Journal of the American Chemical Society 89, 5505 (1967)), and mixtures of dicyclohexylcarbodiimide and dimethyl sulfoxide (Journal of the American Chemical Society 87, 5661 (1965)).

The formula CLVI compound is then prepared from the formula CLV compound by hydrolysis of the blocking groups, according to $R_{31}$, as described above.

From the formula CLVI 11-deoxy-PGE-type compound, there is prepared the corresponding 11-deoxy-PGF$_\alpha$- or PGF$_\beta$-type compound. Further, employing the 8$\beta$,12$\alpha$-PGA-type compound corresponding to the formula CXLVI PGA-type compound, there are prepared the corresponding 8$\beta$,12$\alpha$-11-deoxy-PGE-, PGF$_\alpha$-, or PGF$_\beta$-type products.

Chart O provides a method whereby the formula CLXI, 8β,12α-PGE-type compound is transformed to the formula CLXVII 8β,12α-PGF$_\alpha$-, PGF$_\beta$-, or PGE-type compounds.

The formula CLXI compound is prepared hereinabove. The formula CLXII compound is then prepared from the formula CLXI compound by the procedure described hereinabove for the preparation of the formula CLIII compound from the formula CLI compound. Thereafter the formula CLXIII compound, the formula CLXIV compound, formula CLXV compound, and formula CLXVI compound are successively prepared from the formula CLXII compound employing methods known in the art. See for reference Belgian Pat. No. 804,873, Derwent Farmdoc CPI No. 22865V/13, and G. L. Bundy et al., J. Am. Chem. Soc. 94, 2123 (1972). There are first formed the formula CXLIII 10,11-epoxides, using any agent known to epoxidize an α,β-unsaturated ketone without reacting with isolated carbon-carbon double bonds, for example see Steroid Reactions, Carl Djerassi, ed., Holden-Day Inc., 1963, p. 593. Especially preferred are aqueous hydrogen peroxide or an organic tertiary hydroperoxide. See, for example, Organic Peroxides, A. V. Tobolsky et al., Interscience Publishers, N.Y. 1954. For this purpose, the peroxide or hydroperoxide is employed in an amount of at least one equivalent per mole of formula CLXII reactant in the presence of a strong base, e.g., an alkali metal hydroxide, a metal alkoxide, or a quaternary ammonium hydroxide. For example, there is employed lithium hydroxide, sodium hydroxide, potassium hydroxide, lithium ethoxide, lithium octyloxide, magnesium methoxide, magnesium isopropoxide, benzyltrimethylammonium hydroxide, and the like.

It is advantageous to use an inert liquid diluent in the epoxidation step to produce a mobile homogeneous reaction mixture, for example, a lower alkanol, dioxane, tetrahydrofuran, dimethoxyethane, dimethylsulfoxide, or dimethylsulfone. A reaction temperature in the range $-60°$ to $0°$ C. is generally preferred, especially below $-10°$ C. At a temperature of $-20°$ C., the epoxidation is usually complete in 3 to 6 hours. It is also preferred that the reaction be carried out in an atmosphere of an inert gas, e.g., nitrogen, helium, or argon. When the reaction is complete as shown by the absence of starting material on TLC plates (5% acetone in dichloromethane), the reaction mixture is neutralized, and the epoxy product is isolated by procedures known in the art, for example, evaporation of the diluent and extraction of the residue with an appropriate water-immiscible solvent, e.g., ethyl acetate.

This transformation of CLXII to CLXIII usually produces a mixture of formula CLXIII alpha and beta epoxides. Although these mixtures are separable into the individual alpha and beta isomers, for example, by chromatography by procedures known to be useful for separating alpha and beta epoxide mixtures, it is usually advantageous to transform the formula CLXIII mixture of alpha and beta epoxides to the corresponding mixture of formula CLXIV 11α- and 11β-hydroxy compounds. The latter mixture is then readily separated into the 11α and 11β compounds, for example, by chromatography on silica gel.

Referring again to Chart O, the transformation of epoxide CLXIII to hydroxy compound CLXIV is accomplished by reduction with chromium (II) salts, e.g., chromium (II) chloride or chromium (II) acetate. Those salts are prepared by methods known in the art. This reduction is carried out by procedures known in the art for using chromium (II) salts to reduce epoxides of αβ-unsaturated ketones to β-hydroxy ketones. See, for example, Cole et al., J. Org. Chem. 19, 131 (1954), and Neher et al., Helv. Chem. Acta 42, 132 (1959). In these reactions, the absence of air and strong acids is desirable.

Amalgamated aluminum metal has also been found to be useful as a reducing agent in place of chromium (II) salts for the above purpose. Amaglamated aluminum is prepared by procedures known in the art, for example, by contacting aluminum metal in the form of foil, thin sheet, turnings, or granules with a mercury (II) salt, for example, mercuric chloride, advantageously in the presence of sufficient water to dissolve the mercury (II) salt. Preferably, the surface of the aluminum metal is free of oxide. That is readily accomplished by physical removal of the usual oxide layer, e.g., by abrasion or scraping, or chemically, e.g., by etching with aqueous sodium hydroxide solution. It is only necessary that the aluminum surface be amalgamated. The amalgamated aluminum should be freshly prepared, and maintained in the absence of air and moisture until used.

The reductive opening of the formula CLXIII epoxide ring is accomplished by contacting said epoxide with the amalgamated aluminum in the presence of a hydroxylic solvent and sufficient inert organic liquid diluent to give a mobile and homogeneous reaction mixture with respect to the hydroxylic solvent and said epoxide. Among hydroxylic solvents, water is especially preferred although lower alkanols, e.g., methanol and ethanols are also operable.

Examples of inert organic liquid diluents are normally liquid ethers such as diethyl ether, tetrahydrofuran, dimethoxyethane, diglyme (dimethyl ether of diethylene glycol), and the like. Especially preferred is tetrahydrofuran. When a water-immiscible liquid diluent is used, a mixture of water and methanol or ethanol is especially useful in this reaction since the latter two solvents also aid in forming the desired homogeneous reaction mixture. For example, a mixture of diethyl ether and water is used with sufficient methanol to give a homogeneous reaction mixture. Thereafter the formula CLXV compound is prepared from the formula CLXIV compound by separating the 11α-hydroxy epimer from the 11- epimeric mixture. Thereafter, the formula CLXVI compound is prepared from the formula CLXV compound by removal of the blocking groups, using methods described in Chart N wherein the formula CLX compound is transformed to the formula CLV compound. Thereafter, the formula CLXVII compound is prepared from the formula CLXVI compound using the procedures described herein in Chart F, i.e. the preparation of the formula LXXIII compound from the formula LXXII compound.

Optionally, the procedure of Chart O is followed, except that 13,14-didehydro-8β,12α-PGA-type starting material is used in place of 14-halo-8β,12α-PGA-type starting material, and accordingly 13,14-didehydro-PG-type products are prepared. Thus the procedure of Chart O is followed except that in place of the Y$_2$ moiety in the formulas of Chart O, the Y$_1$ moiety is present.

Chart P provides a method whereby the formula CLXXI PGF$_\alpha$ or 11-deoxy-PGF$_\alpha$-type starting material, as prepared herein, is transformed into the corresponding PGE-type compound by selective silylation of all hydroxy hydrogens of the formula CLXXI compound, other than the C-9 hydroxy.

The formula CLXXII compound is prepared from the formula CLXXI compound by selective silylation of the various hydroxy groups of the formula CLXXI compound over the C-19 hydroxy. Silyl groups with the scope -Si($G_1$)$_3$, wherein G is alkyl of 1 to 4 carbon atoms, inclusive, aralkyl of 7 to 12 carbon atoms, inclusive, phenyl, phenyl substituted with one or 2 chloro, fluoro, or alkyl of one to 4 carbon atoms, inclusive, with the proviso that the various G's of the -Si(G)$_3$ moiety are the same or different, are employed. These reagents are known in the art and their use is known in the art.

For the selective silylation procedure of Chart P procedures known in the art for selective silylation of known prostanoic acid derivatives are employed. See for reference U.S. Pat. No. 3,822,303 (issued July 2, 1974), German Offenlegungschrift No. 2,259,195 (Derwent Farmdoc CPI36457U-B), and Netherlands Patent No. 7,214,142 (Derwent Farmdoc CPI 26221U-B).

Examples of the -Si($G_1$)$_3$ moiety are trimethylsilyl, dimethyl(tert-butyl)silyl, dimethyl phenyl silyl, and methylphenylsilyl. Examples of alkyl of one to 4 carbon atoms, inclusive, aralkyl of 7 to 12 carbon atoms, inclusive, and phenyl or substituted phenyl moieties are provided hereinabove.

The formula CLXXIII compound is prepared from the formula CLXXII compound by oxidation of the C-9 hydroxy to a C-9 oxo. Oxidation reagents and methods known in the art are employed. For example, the Jones reagent is advantageously employed as discussed above.

The formula CLXXIV compound is prepared from the formula CLXXIII compound by hydrolysis of the silyl groups. Hydrolysis proceeds by methods known in the art, e.g. the use of water or dilute aqueous acetic acid in a diluent of water and a quantity of a water miscible solvent sufficient to yield a homogeneous reaction mixture. This hydrolysis is ordinarily complete within 2 to 12 hours at 25° C., and is preferably carried in an atmosphere of an inert gas such as nitrogen or argon.

Optionally the procedure of Chart P is used to transform 13,14-dedehydro-PGF$_\alpha$-type products to corresponding 13,14-didehydro-PGE-type products. Accordingly, in this alternate process $Y_2$ in this Chart is defined to be —C≡C— instead of trans—CH=C-(Hal)—.

Chart R provides a method whereby the 14-halo compounds described herein are transformed corresponding 13,14-dihydro-PG-type products.

The transformation of Chart R (the formula CLXXXI compound to the formula CLXXXII compound) proceeds by dehydrohalogenation. By the preferred method the reaction proceeds using as a reaction diluent a mixture of dimethylsulfoxide, or similar aprotic solvent, and methanol in ratio by volumn between 5:1 and 10:1. Thereafter a strong organic base, for example potassium t-butoxide or sodium methoxide is added and the reaction is allowed to proceed to completion, ordinarily within about 24 hours. Reaction temperatures between 0°-25° C. are employed for convenience.

When this dehydrohalogenation procedure is employed using PGE- or PGA-type compounds or 8β,12α-PGE- or PGA-type compounds undesired dehydration and/or double bond migration occurs. Accordingly, it is preferred that these dehydrations be performed on PGF-type reactants and thereafter the corresponding 13,14-didehydro-PGF-type compounds be transformed respectively to 13,14-didehydro-PGE- or PGA-type products, by procedures described hereinabove. Accordingly, by this preferred method the 14-halo-PGF compound is successively transformed to a 13,14-didehydro-PGF-type compound and thereafter to 13,14-didehydro-PGE- or PGA-type compounds.

Optically active PG-type products are obtained from optically active intermediates, according to the process steps of the above charts. Likewise optically active PG-type compounds are obtained from corresponding optically active PG-type compounds following the procedures in the above charts. When racemic intermediates are used in the reactions above, racemic products are obtained. These products may be used in their racemic form or if preferred they may be resolved as optically active enantiomers following procedures known in the art. For example, when a PG-type free acid is obtained, the racemic form thereof is resolved into d and l forms by reacting said free acid by known procedures with an optically active base (e.g., brucine or strychnine) thereby yielding a mixture of 2 diastereomers which are separable by procedures known in the art (fractional crystallization to yield the separate diastereomeric salts). The optically active acid may then be prepared from salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed.

For alkyl esters of PGE-type compounds enzymatic processes for transformation of esters to their acid forms may be used by methods known in the art when saponification procedures would cause dehydration of the prostaglandin analog. See for reference E. G. Daniles, Process For Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid PG-type compounds, differing as to yield and purity of product.

Thus by one method, the PG-type compound is converted to a tertiary amine salt, reacted with pivaloyl halide to give the mixed acid anhydride and then reacted with the aromatic alcohol. Alternatively, instead of pivaloyl halide, an alkyl or arylsulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231–236, John Wiley and Sons, Inc., New York, (1967). The PG-type compound is contacted with one to ten molar equivalents of the aromatic alcohol in the presence of 2–10 molar equivalents of dicyclohexylcarbodiimide in pyridine as a solvent.

One preferred novel process for the preparation of these esters, however, comprises the steps:

(a) forming a mixed anhydride with the PG-type compound and isobutylchloroformate in the presence of a tertiary amine and (b) reacting the anhydride with an appropriate aromatic alcohol.

The mixed anhydride described above is formed readily at temperatures in the range −40° to +60° C., preferably at −10° to +10° C. so that the rate is reasonably fast and yet side reactions are minimized. The isobutylchloroformate reagent is preferably used in excess, for example 1.2 molar equivalents up to 4.0 mole of the PG-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethyamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible nonsolvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are tranformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt derived. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

The acids or esters of this invention prepared by the processes of this invention are transformed to lower alkanoates by interaction of a free hydroxy compound with a carboxyacylating agent, preferably the anhydride of a lower alkanoic acid, i.e., an alkanoic acid of two to 8 carbon atoms, inclusive. For example, use of acetic anhyride gives the corresponding acetate. Similar use of propionic anhydride, isobutyric anhydride, or hexanoic anhydride gives the corresponding carboxyacylate..

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent.

An inert organic dilluent, (e.g., dioxane) can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C reaction temperature, a 12 to 24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

DESCRIPTION OF THE PREFERRED EMBODIMENTS

The invention can be more fully understood by the following examples and preparations.

All temperatures are in degrees centrigrade.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, and T-60 and T-60 spectrophotometer on deuterochloroform solutions with tetramethylsilane as an internal standard (downfield).

Mass spectra are recorded on an CEC model 21-110B Double Focusing High Resolution Mass Spectrometer on an LKB Model 9000 Gas-Chromatograph-Mass Spectrometer. Trimethylsilyl derivatives are used, except where otherwise indicated.

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

DDQ refers to 2,3-dichloro-5,6-dicyano-1,4-benzoquinone. THF refers to tetrahydrofuran. Specific Rotations, [α], are determined for solutions of a compound in the specified solvent at ambient temperature with a Perkin-Elmer Model 141 Automatic Polarimeter.

EXAMPLE 1

Dimethyl 3,3-dimethyl-2-oxo-4-phenylbutylphosphonate,

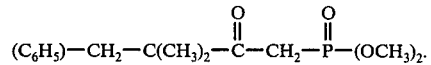

A. To a solution of 101.2 g. of diisopropylamine in 125 ml. of tetrahydrofuran under nitrogen at 0° C. is added dropwise with cooling (using an ice-methanol bath) 625 ml. of 1.6M n-butyllithium in hexane. To the resulting solution is added dropwise with cooling 45.6 ml. of isobutyric acid. This mixture is then stirred at 0° C. for 90 min. and thereafter cooled to −15° C. Benzyl chloride (60 ml.) is added with stirring at such a rate as to maintain the reaction temperature below −5° C. The resulting mixture is thereafter stirred at ambient temperature for 4 hours. This stirred mixture is then diluted with diethyl ether and excess cold dilute hydrochloric acid. The organic layer is washed with saline and thereafter dried, concentrated, and the residue distilled under vacuum. Accordingly, there is prepared 2,2-dimethyl-3-phenyl propionic acid.

B. A mixture of 48 g. of the product of part A of this example and 82 g. of thionyl chloride are heated with stirring on a steam bath for 2 hours. The mixture is then concentrated under vacuum. Thereafter dry benzene is added and the resulting mixture is concentrated again, removing all traces of thionyl chloride. Distillation of this residue yields 48.2 g. of 2,2-dimethyl-3-phenyl-propionyl chloride.

C. To a solution of 63 g. of dimethylmethylphosphonate. in 600 ml. of tetrahydrofuran under nitrogen at −75° C. is added with stirring 312 ml. of 1.6 molar n-butyllithium in hexane. The addition rate is adjusted so that the reaction temperature remains below 55° C. Ten minutes after the addition is complete, 48.2 g. of the reaction product of part B of this example and 50 ml. of tetrahydrofuran are added dropwise at such rate as to maintain the reaction temperature below −60° C. The resulting mixture is then stirred at −75° C. for 2 hours and then ambient temperature overnight. Acetic acid (20 ml.) is thereafter added and the resulting mixture distilled under vacuum, thereby removing most of the tetrahydrofuran. The residue is then shaken with diethyl ether in methylene chloride (3:1 by volume) and a cold dilute sodium bicarbonate solution. The organic layer is then washed with brine, dried, and concentrated. The residue was crystallized from diethyl ether, yielding 54 g. of dimethyl 3,3-dimethyl-2-oxo-4-phenylbutylphosphonate the title compound. The melting point is 48°–50° C.

Following the procedure of Example 1, but using in place of benzyl chloride substituted benzyl chlorides of the formula

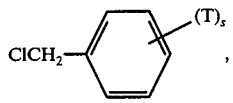

wherein T is fluoro, chloro, trifluoromethyl, alkyl of one to 3 carbon atoms, inclusive, or alkoxy of one to 3 carbon atoms, inclusive, and wherein s is zero, one, 2, or 3, with the proviso that not more than two T's are other than alkyl, and with the further proviso that the various T's may be the same or different, there are prepared the corresponding dimethyl-3,3-dimethyl-2-oxo-4-(substituted phenyl)butylphosphonates. For example, there is prepared by this procedure dimethyl 3,3-dimethyl-2-oxo-4-(p-fluorophenyl)-butylphosphonate.

Further, following the procedure of Example 1, but using in place of the isobutyric acid of Example 1, part A, propionic acid, there is prepared dimethyl 3-methyl-2-oxo-4-phenylbutylphosphonate. Following the procedure of Example 1, but using the substituted benzyl chlorides described above in place of benzyl chloride and propionic acid in place of isobutyric acid there are prepared the various dimethyl 3-methyl-2-oxo-4-(substituted phenyl)butylphosphonates wherein the phenyl substitution is as described above.

Further, following the procedure of Example 1, but using acetic acid in place of isobutyric acid as used in Example 1, part A, there is prepared dimethyl-2-oxo-4-phenylbutylphosphonate. Using acetic acid in combination with the various substituted benzyl chlorides described above according to the procedure of Example 1, there are prepared the various dimethyl 2-oxo-4-(substitutedphenyl)-butyl phosponates, wherein the phenyl substitution is as described above.

Following the procedure of Example 1, but using 2,2-difluoroacetic acid in place of isobutyric acid as used in part A of Example 1, there is prepared dimethyl 3,3-difluoro-2-oxo-4-phenylbutylphosphonate. Further, following the procedure of Example 1, but using 2,2-difluoro acetic acid in combination with substituted benzyl chlorides described above, there are prepared the corresponding dimethyl 3,3-difluoro-2-oxo-4-(substituted)phenylbutylphosphonate, wherein the phenyl substitution is as described above.

Further, following the procedure of Example 1, but using 2-fluoro acetic acid in place of isobutyric acid there is prepared dimethyl 3-fluoro-2-oxo-4-phenylbutylphosphonate.

Using 2-fluoro acetic acid and the various substituted benzyl chlorides described above according to the procedure of Example 1, there are prepared the various dimethyl 3-fluoro-2-oxo-4-(substituted)phenylbutyl phosphonates, wherein the phenyl substitution is as described above.

EXAMPLE 2

Triphenylphosphonium salt of 2,2-difluoro-5—bromopentanoic acid, $Br(C_6H_5)_3P—(CH_2)_3—CF_2—COOH$.

A. Methyl furoate (50.4 g.) is dissolved in 180 ml. of methanol. Thereafter 1 g. of 5 percent palladium-on-charcoal is added. This mixture is then hydrogenated at 1 to 3 atmospheres. After 45 hours 0.79 moles of hydrogen are consumed. The black mixture is then filtered through Celite using 50 ml. of methanol to wash the reaction flask and filter. Evaporation of the filtrate under reduced pressure at 40°–45° C. bath temperature yields 51 g. of a yellow oil which is thereafter distilled, collecting that fraction boiling at 32°–35° C. Thereby, methyl tetrahydrofurate (46.7 g.) is prepared.

B. Anhydrous hydrobromic acid is bubbled through 50 ml. of acetic anhydride with cooling until a specific gravity of 1.3 is obtained. This reagent is then added to 25 g. of the reaction product of step A of this example, with exclusion of moisture while cooling and stirring. Stirring in the ice water bath is continued for 15 min.; thereafter, the mixture is allowed to stand at room temperature overnight. The reaction mixture is then poured into 600 g. of crushed ice and water with stirring and extracted with diethyl ether. The ether extract is washed with aqueous sodium hydroxide, dried over sodium sulfate, filtered, and thereafter evaporated under reduced pressure to yield 38 g. of a pale yellow oil, which is thereafter distilled under high vacuum, yielding 31.6 g. of methyl 2-acetoxy-5-bromopentanoate.

C. To a solution of 60 g. of the reaction product of part B of this example in 200 ml. of methanol is added 100 ml. of methanol, which is saturated with hydrobromic acid at 0° C. and 1.3 specific gravity before the addition. The reaction mixture is then allowed to stand at room temperature overnight. The solvent is thereafter evaporated under reduced pressure at 35° C. bath temperature and 400 ml. of toluene is thereafter added. The solvent is again evaporated. This residue is then dissolved in 2 l. of ethyl acetate, washed with 5 percent aqueous sodium hydroxide solution and sodium chloride solution before being dried over sodium sulfate. Filtration and evaporation of the solvent under reduced pressure at 45° C. yields 42 g. of oil which is distilled under high vacuum, yielding 28.8 g. of methyl 2-hydroxy-5-bromopentanoate.

D. To a solution of 34.4 g. of the reaction product of part C of this example and 400 ml. of acetone is added with stirring and cooling 75 ml. of Jones reagent (26.73 g. of $CrO_3$ in 23 ml. of concentrated sulfuric acid, diluted to 100 ml. with water) at such a rate that the reaction temperature is maintained between 30° and 40° C. The reaction is complete in approximately 20 min. Thereafter the reaction mixture is stirred for 1.5 hr. Thereafter 150 ml. of isopropyl alcohol are slowly added with stirring during 30 min. The reaction mixture is then diluted with 1.8 l. of water and extracted with 2.4 l. of methylene chloride. These extracts are washed with brine and dried with sodium sulfate. Filtration and evaporation of the solvent under reduced pressure yields 30.8 g. of a pale yellow oil, containing methyl 2-oxo-5-bromopentanoate. This oil is used in the following steps of this example without further purification.

E. With the exclusion of moisture under a nitrogen atmosphere 195 ml. of $MoF_6.BF_3$ is cooled in a dry-ice acetone bath. A solution of 30.8 g. of the reaction product of step D of this example and 40 ml. of methylene chloride is added dropwise with stirring over a period of 15 min. The reaction temperature is maintained between −35 and −45° C. Stirring the dry ice acetone bath is continued for one hour, the cooling bath thereafter is removed, and the reaction mixture thereafter diluted with 200 ml. of methylene chloride and 400 ml. of water. The organic and aqueous layers are separated, the aqueous layer being extracted with methylene chloride and the combined methylene chloride extracts washed with 250 ml. of water, 250 ml. of 5 percent aqueous potassium bicarbonate, 250 ml. of brine, and thereafter dried over sodium sulfate. Filtration and evaporation of the solvent yields 31.1 g. of a dark brown oil, which when distilled under high vacuum yields methyl 2,2-difluoro-5-bromopentanoate (14 g.).

F. The reaction product of part E of this example (28 g.) is stirred in 175 ml. of aqueous hydrobromic acid (specific gravity 1.71) for 3 hours at room temperature. The reaction mixture is then cooled in an ice bath, and diluted with 1300 ml. of diethyl ether. The organic and aqueous layers are separated and the aqueous layer is extracted with diethyl ether. The combined etheral solutions are washed with water and the ethereal loss solutions are backwashed with 400 ml. of ether and the combined ethereal solutions is then dried over sodium sulfate. Filtration and evaporation of the solvent yields 27.7 g. of a pale yellow oil, 2,2-difluoro-5-bromopentanoic acid, which is used in the following step of this example without further purification.

G. A mixture of 15.2 g. of the reaction product of part F of this example, 80 ml. of acetonitrile and 22 g. of triphenylphosphine are heated to reflux with stirring for 30 hours. The reaction mixture is then heated to 110° C., diluted with 160 ml. of toluene, and the mixture is allowed to cool slowly at room temperature for 12 hours with stirring. The reaction mixture is then stored at 5° C. for 24 hours. A precipitate is collected, washed with 50 ml. of toluene, and dried under vacuum at room temperature. 20.9 g. of the title compound of this example is thereby obtained.

EXAMPLE 3

(6-Carboxhexyl)triphenylphosphonium bromide.

A mixture of 63.6 g. of 7-bromoheptanoic acid, 80 g. of triphenylphosphine, and 30 ml. of acetonitrile, is refluxed for 68 hours. Thereafter 200 ml. of acetonitrile is removed by distillation. After the remaining solution is cooled to room temperature, 30 ml. of benzene is added with stirring. The mixture is then allowed to stand for 12 hours. A solid separates which is collected by filtration, yielding 134.1 g. of product, melting point 185°–187° C.

Following the procedure of Example 3, but using 3-bromopropionic acid, 4-bromobutanoic acid, 5-bromopentanoic acid, or 6-bromohexanoic acid, in place of 7-bromoheptanoic acid, there are prepared the corresponding ($\omega$-carboxyalkyl)-triphenylphosphonium bromides.

EXAMPLE 4

$3\alpha$-Benzoyloxy-$5\alpha$-hydroxy-$2\beta$-(2-chloro-3-oxo-4,4-dimethyl-trans-1-octenyl)-$1\alpha$-cyclopentaneacetic acid, $\gamma$ lactone (Formula XXIII: $R_7$ is n-butyl, $R_{16}$ is benzoyloxy, $R_3$ and $R_4$ of the $L_1$ moiety are methyl, and $Y_2$ is trans—CH=C(Cl)—).

Refer to Chart A.

A. A solution of 24.3 g. of thallous ethoxide in 125 ml. of dry benzene is cooled in an ice bath, and thereafter a solution of 25.3 g. of methyl 3,3-dimethyl-2-oxo-heptylphosphonate in 75 ml. of benzene is added and thereafter rinsed with 50 ml. of benzene. The solution is stirred for 30 min. at 5° C. and thereafter 22.1 g. of crystalline $3\alpha$-benzoyloxy-$5\alpha$-hydroxy-$2\beta$-carboxaldehyde-$1\alpha$-cyclopentaneacetic acid, $\gamma$ lactone is added rapidly. This reaction mixture is then stirred for 13 hours at ambient temperature yielding a brown solution of pH 9–10. Acetic acid (6 ml.) is added and the mixture is transferred to a beaker with 600 ml. of diethyl ether. Celite and 500 ml. of water is added, followed by the addition of 30 ml. (about 33 g.) of saturated potassium iodide. The mixture (containing a bright yellow precipitate of thallous iodide) is stirred for about 45 min., and thereafter filtered through a bed of Celite. The organic layer is then washed with water, aqueous potassium bicarbonate, and brine Thereafter the resulting mixture is dried over magnesium sulfate and evaporated at reduced pressure, yielding 33.6 g. of an oil, which is then chromatographed on 600 g. of silica gel packed in 20 percent ethyl acetate in cyclohexane. Elution, collecting 500 ml. fractions, with 2 l. of 20 percent, 2 l. of 25 percent, and 4 l. of 30 percent ethyl acetate in cyclohexane yields 20.3 g. of crude product, which upon recrystallization from 240 ml. of diethyl ether in pentane (2:1) yields $3\alpha$-benzoyloxy-$5\alpha$-hydroxy-$2\beta$-(3-oxo-4,4-dimethyl-trans-1-octenyl)-$1\alpha$-cyclopentaneacetic acid, $\gamma$ lactone.

Alternatively this product is prepared by adding $3\alpha$-benzoyloxy-$2\beta$-carboxaldehyde-$5\alpha$-hydroxy-$1\alpha$-cyclopentaneacetic acid $\gamma$ lactone (3 g.) in 30 ml. of dichloromethane to a solution of dimethyl 2-oxo-3,3-dimethylheptylphosphonate (6.69 g.) and sodium hydride (1.35 g.) in 15 ml. of tetrahydrofuran. The resulting reaction mixture is then stirred for 2 hours at about 25° C., acidified with acetic acid, and concentrated under reduced pressure. The residue is partitioned between dichloromethane and water, and the organic phase is concentrated. The residue is chromatographed on silica gel, eluting with ethyl acetate in Skellysolve B (1:1).

B. A solution of the reaction product of part A of this example (1.15 g.) in dioxane (35 ml.) is treated with N-chlorosuccinimide (9.7 g.) and stirred for 6 days. The resulting solution is then diluted with methylene chloride, washed with saline and a sodium sulfate solution, dried, and evaporated to yield a viscous residue. The residue in benzene is subjected to silica gel chromatography, eluting with hexane and ethyl acetate (9:1) whereupon pure $3\alpha$-benzoyloxy-$5\alpha$-hydroxy-$2\beta$-(1,2-dichloro-3-oxo-4,4-dimethyloctyl)-$1\alpha$-cyclopentaneacetic acid $\gamma$ lactone is recovered (as a mixture of isomers). Thereafter the dichlorides so obtained are diluted with pyridine (20 ml.) and heated at 100° C. for 4.5 hours. The resulting solution is then diluted with diethyl ether and washed with ice cold dilute hydrochloric acid and brine. The resulting mixture is then dried and subject to silica gel chromatography, eluting with hexane and ethyl acetate (9:1), yielding 0.765 g. of pure product. NMR absorptions are observed at 0.85, 1.22, 1.0–1.9, 1.9–3.5, 4.8–5.1, 5.35, 6.28, 7.2–7.6, and 7.8–8.1 $\delta$. The mass spectrum shows peaks at 432, 396, 376, 378, 254, and 256.

Alternatively, the reaction product of part A above (0.190 g.) in dry pyridine (5 ml.) at 0° C. is treated with freshly distilled sulfuryl chloride (0.386 g.) and the reaction is maintained for 5 hours. Thereafter additional sulfuryl chloride (0.667 g.) and pyridine (5 ml.) is added and the reaction continued for 12 hours for ambient temperature. A resulting dark solution is then diluted with methylene chloride, washed with ice cold phosphoric acid, sodium bicarbonate, dried, and evaporated. The residue is chromatographed on silica gel eluting with hexane and ethyl acetate (9:1). Pure product identical with that recovered in the preceding paragraph is obtained.

Following the procedure of Example 4, but using in place of 3α-benzoyloxy-5α-hydroxy-2β-carboxaldehyde-1α-cyclopentaneacetic acid γ lactone; 5α-hydroxy-2β-carboxaldehyde-1α-cyclopentaneacetic acid γ lactone, there is obtained 5α-hydroxy-2β-(2-chloro-3-oxo-4,4-dimethyl-trans-1-octenyl)-1α-cyclopentaneacetic acid γ lactone.

following the procedure of Example 4, but using in place of dimethyl 2-oxo-3,3-dimethylheptylphosphonate, any of the various dimethyl phosphonates described hereinabove there are prepared the corresponding 3α-benzoyloxy-5α-hydroxy-1α-cyclopentaneacetic acid γ lactones or 5α-hydroxy-1α-cyclopentane-acetic acid γ lactones with a 2β-(2-chloro-3-oxo-trans-1-alkenyl)-substituent, optionally substituted, as follows:

4,4-difluorohexenyl; 4,4-difluoroheptenyl; 4,4-difluorooctenyl; 4,4-difluorononenyl; 4,4-difluorodecenyl; 4-fluorohexenyl; 4-fluoroheptenyl; 4-fluorooctenyl; 4-fluorononenyl; 4-fluorodecenyl; 4,4-dimethylhexenyl; 4,4-dimethyl-heptenyl; 4,4-dimethylnonenyl; 4,4-dimethyldecenyl; 4-methylhexenyl; 4-methylheptenyl; 4-methyloctenyl; 4-methyl-nonenyl; 4-methyldecenyl; hexenyl; heptenyl; octenyl; nonenyl; decenyl; 5-phenyl-pentenyl; 5-(m-trifluoromethyl-phenyl)-pentenyl; 5-(m-fluorophenyl)-pentenyl; 5-(m-chlorophenyl)-pentenyl; 5-(p-trifluoromethylphenyl)-pentenyl; 5-(p-fluorophenyl)-pentenyl; 5-(p-chlorophenyl)-pentenyl; 4-methyl-5-phenylpentenyl; 4-methyl-5-(m-trifluoromethylphenyl)pentenyl; 4-methyl-5-(m-fluorophenyl)-pentenyl; 4-methyl-5-(p-trifluoromethylphenyl)-pentenyl; 4-methyl-5-(p-fluorophenyl)-pentenyl; 4-methyl-5-(p-chlorophenyl)-pentenyl; 4,4-dimethyl-5-(m-trifluoromethylphenyl)-pentenyl; 4,4-dimethyl-5-(m-fluorophenyl)-pentenyl; 4,4-difluoro-5-(m-chlorophenyl)-pentenyl; 4,4-dimethyl-5-(p-trifluoromethylphenyl)-pentenyl; 4,4-dimethyl-5-(p-fluorophenyl)-pentenyl; 4,4-dimethyl-5-(p-chlorophenyl)-pentenyl; 4-fluoro-5-phenylpentenyl; 4-fluoro-5-(m-trifluoromethylphenyl)-pentenyl; 4-fluoro-5-(m-fluorophenyl)-pentenyl; 4-fluoro-5-(m-chlorophenyl)-pentenyl; 4-fluoro-5-(p-trifluoromethyl-phenyl)-pentenyl; 4-fluoro-5-(p-fluorophenyl)-pentenyl; 4-fluoro-5-(p-chlorophenyl)-pentenyl; 4,4-difluoro-5-phenyl-pentenyl; 4,4-difluoro-5-(m-trifluoromethylphenyl)-pentenyl; 4,4-difluoro-5-(m-fluorophenyl)-pentenyl; 4,4-difluoro-5-(m-chlorophenyl)-pentenyl; 4,4-difluoro-5-(p-trifluoromethylphenyl)-pentenyl; 4,4-difluoro-5-(p-fluorophenyl)-pentenyl; 4,4-difluoro-5-(p-chlorophenyl)-pentenyl; 4-phenoxybutenyl; 4-(m-trifluoromethylphenoxy)-butenyl; 4-(p-fluorophenoxy)-butenyl; 4-(m-chlorophenoxy)-butenyl; 4-(m-trifluoromethylphenoxy)-butenyl; 4-(p-fluorophenoxy)-butenyl; 4-(p-chlorophenoxy)-butenyl; 4-methyl-4-phenoxybutenyl; 4-methyl-4-(m-trifluoromethylphenoxy)-butenyl; 4-methyl-4-(m-fluorophenoxy)-butenyl; 4-methyl-4-(m-chlorophenoxy)-butenyl; 4-methyl-4-(p-trifluoromethylphenoxy)-butenyl; 4-methyl-4-(p-fluorophenoxy)-butenyl; 4-methyl-4-(p-chlorophenoxy)-butenyl; 4,4-dimethyl-4-phenoxybutenyl; 4,4-dimethyl-4-(trifluoromethylphenoxy)-butenyl; 4,4-dimethyl-4-(m-fluorophenoxy)-butenyl; 4,4-dimethyl-4-(m-chlorophenoxy)-butenyl; 4,4-dimethyl-4-(p-trifluoromethyl-phenoxy)-butenyl; 4,4-dimethyl-4-(p-fluorophenoxy)-butenyl; 4,4-dimethyl-4-(p-chlorophenoxy)-butenyl; and the like.

PGF$_\alpha$, PGE, PGF$_\beta$, PGA, and PGB analogs described herein are prepared from the formula XXIII compound wherein the C-3 position of the cyclopentane ring is substituted by a benzoyloxy moiety at C-3, as described above (Example 4).

Likewise, intermediates useful in preparing 11-deoxy-PGF$_\alpha$, 11-deoxy-PGE, and 11-deoxy-PGF$_\beta$-type compounds of these disclosed are prepared as described above in and following Example 4 except the starting material employed is a 3-unsubstituted lactone; that is 5α-hydroxy-2β-carboxaldehyde-1α-cyclopentaneacetic acid γ lactone. Accordingly, there are prepared 5α-hydroxy-1α-cyclopentaneacetic acid γ lactones with the various 2β-side chains described following Example 4 which are useful in the same manner as the 3α-benzoyloxy compounds in the procedures of succeeding examples for preparing the 11-deoxy-PGF$_\alpha$-, PGE-, or PGF$_\beta$-type compounds corresponding to the PGF$_\alpha$-, PGE-, and PGF$_\beta$-type compounds therein prepared.

EXAMPLE 5

3α-Benzoyloxy-5α-hydroxy-2β-[2-chloro-(3R)-3-hydroxy-4,4-dimethyl-trans-1-octenyl]-1α-cyclopentaneacetic acid γ lactone (Formula XXIV: $R_3$ and $R_4$ of the $L_1$ moiety are methyl, $R_5$ and $R_6$ of the $M_5$ moiety are hydrogen, $R_7$ is n-pentyl, $R_{16}$ is benzoyloxy, and $Y_2$ is trans—CH=C(Cl) or its (3S)-hydroxy epimer.

Sodium borohydride (0.92 g.) is slowly added to a stirred suspension of 2.1 g. of anhydrous zinc chloride in 45 ml. of dimethyl ether in ethylene glycol (glyme) with ice bath cooling. The mixture is stirred for 20 hours at ambient temperature and thereafter cooled to −18° C. A solution of 0.76 g. of 3α-benzoyloxy-5α-hydroxy-2β-(2-chloro-3-oxo-4,4-dimethyl-trans-1-octenyl)-1α-cyclopentaneacetic acid γ lactone (prepared according to Example 4) in 12 ml. of glyme is added over a period of 20 minutes. Stirring is continued for 24 hours at −20° C. and thereafter 40 ml. of water is cautiously added. The reaction mixture is warmed to room temperature, diluted with ethyl acetate, and washed twice with brine. The aqueous layers are extracted with ethyl acetate. The combined organic extracts are dried over sodium sulfate and evaporated to yield crude product, which when chromatographed on 12 g. of silica gel eluting with hexane and in ethyl acetate (3:1) yields the epimerically pure title product.

The 3R epimer exhibits ultraviolet absorptions at $\lambda_{max}$. equals 229.5 nm. ($\epsilon$ 13,550). The mass spectrum shows absorption at 337, 336, 335, 217, 216, 215, 214, and 213. NMR absorptions in CDCl$_3$ are observed at 0.85, 0.90, 0.80–1.0, 1.0–1.5, 1.9–3.0, 3.0–3.6, 4.0, 4.7–5.5, 5.65, 7.2–7.7, and 7.8–8.2 δ.

The 3S epimer exhibits NMR absorptions in CDCl$_3$ at 0.86, 0.90, 0.8–1.0, 1.0–1.5, 2.1–3.0, 3.0–3.8, 4.0, 7.1–7.7, and 7.8–8.2 δ.

Following the procedure of Example 5, but using in place of the 3α-benzoyloxy-5α-hydroxy-2β-(2-chloro-3-oxo-4,4-dimethyl-trans-1-octenyl)-1α-cyclopentaneacetic acid γ lactone starting material employed therein, the various 3α-benzoyloxy-5α-hydroxy-2β-(2-chloro-3-oxo-trans-1-alkenyl, trans-1-cis-5-alkadienyl, or substituted alkenyl or alkadienyl)-1α-cyclopentaneacetic acid γ lactones there are prepared the corresponding 3R or 3S hydroxy products.

Following the procedure of Example 5, but using in place of the 3α-benzoyloxy-5α-hydroxy-2β-(2-chloro-3-oxo-4,4-dimethyl-trans-1-octenyl)-1α-cyclopentaneacetic acid γ lactone used therein, 5α-hydroxy-2β-(2- chloro-3-oxo-trans-1-alkenyl, trans-1-cis-5-alkadienyl, or substituted alkenyl or alkadienyl)-1α-cyclopentaneacetic acid γ lactones described following Example 4, there are prepared the corresponding 3R or 3S-hydroxy products. For example, there are obtained the above 3α-benzoyloxy-5α-hydroxy- or 5α-hydroxy-1α-cyclopentaneacetic acid γ lactones wherein the 2β-side chain in either the 3R or 3S form consists of 2-chloro-3-hydroxy-trans-1-hexenyl;
2-chloro-3-hydroxy-trans-1-heptenyl;
2-chloro-3-hydroxy-trans-1-octenyl;
2-chloro-3-hydroxy-trans-1-nonenyl;
2-chloro-3-hydroxy-trans-1-decenyl;
2-chloro-3-hydroxy-4-methyl-trans-1-octenyl;
2-chloro-3-hydroxy-4-fluoro-trans-1-octenyl;
2-chloro-3-hydroxy-4,4-difluoro-trans-1-octenyl;
2-chloro-3-hydroxy-5-phenyl-trans-1-pentenyl;
2-chloro-3-hydroxy-5-(p-fluorophenyl)-trans-1-pentenyl;
2-chloro-3-hydroxy-5-(m-chlorophenyl)-trans-1-pentenyl;
2-chloro-3-hydroxy-5-(m-trifluoromethylphenyl)-trans-1-pentenyl;
2-chloro-3-hydroxy-4,4-dimethyl-5-phenyl-trans-1-pentenyl;
2-chloro-3-hydroxy-4,4-dimethyl-5-(p-fluorophenyl)-trans-1-pentenyl;
2-chloro-3-hydroxy-4,4-dimethyl-5-(m-chlorophenyl)-trans-1-pentenyl;
2-chloro-3-hydroxy-4,4-dimethyl-5-(m-trifluoromethyl-phenyl)-trans-1-pentenyl;
2-chloro-3-hydroxy-4,4-difluoro-5-phenyl-trans-1-pentenyl;
2-chloro-3-hydroxy-4,4-difluoro-5-(p-fluorophenyl)-trans-1-pentenyl;
2-chloro-3-hydroxy-4,4-difluoro-5-(m-chlorophenyl)-trans-1-pentenyl;
2-chloro-3-hydroxy-4,4-difluoro-5-(m-trifluoromethylphenyl)-trans-1-pentenyl;
2-chloro-3-hydroxy-4-phenoxy-trans-1-butenyl;
2-chloro-3-hydroxy-4-(p-fluorophenoxy)-trans-1-butenyl;
2-chloro-3-hydroxy-4-(m-chlorophenoxy)-trans-1-butenyl;
2-chloro-3-hydroxy-4-(m-trifluoromethylphenoxy)-trans-1-butenyl;
2-chloro-3-hydroxy-4,4-dimethyl-4-phenoxy-trans-1-butenyl;
2-chloro-3-hydroxy-4,4-dimethyl-4-(p-fluorophenoxy)-trans-1-butenyl;
2-chloro-3-hydroxy-4,4-dimethyl-4-(m-chlorophenoxy)-trans-1-butenyl;
2-chloro-3-hydroxy-4,4-dimethyl-4-(m-trifluoromethyl-phenoxy)-trans-1-butenyl; and the like.

EXAMPLE 6

3α-Benzoyloxy-5α-hydroxy-2β-[2-chloro-(3R)-3-methoxy-4,4-dimethyl-trans-1-octenyl]-1α-cyclopentaneacetic acid γ lactone (Formula XXIV: $R_3$ and $R_4$ of the $L_1$ moiety are methyl, $M_5$ is

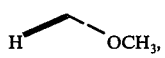

$R_7$ is n-pentyl, $R_{16}$ is benzoyloxy, and Y is trans—CH=C(Cl)—or its (3S) epimer.

Refer to Chart A. A mixture of the (3R) or (3S) reaction product of Example 5 (3.6 g.), silver oxide (4.0 g.) in 50 ml. of methyl iodide and 150 ml. of benzene is stirred and heated at reflux for 18 hours. The resulting mixture is then cooled and filtered and the filtrate concentrated. The resulting concentrate is then subjected to silica gel chromatography, and those fractions as shown by thin layer chromatography to contain pure title compound are combined, yielding respectively the 3R or 3S epimer.

For 3R epimer NMR absorptions are observed at 3.21, 3.8–4.2, 4.9–5.6, 7.25–7.7, and 7.9–8.2 δ.

Following the procedure of Example 6, but using in place of the lactone starting material therein, the various 3-hydroxy lactones described following Example 5, there are prepared the corresponding 3-methoxy products.

EXAMPLE 7

3α-Benzoyloxy-5α-hydroxy-2β-[2-chloro-(3S)-3-hydroxy-3-methyl-trans-1-octenyl]-1α-cyclopentaneacetic acid γ lactone (Formula XXIV as in Example 6 except $M_5$ is

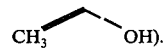

Refer to Chart A.

A solution of 18 g. of 3α-benzoyloxy-5α-hydroxy-2β-(2-chloro-3-oxo-trans-1-octenyl)-1α-cyclopentaneacetic acid γ lactone in 890 ml. of dry benzene is cooled to 9° C. under a nitrogen atmosphere. A toluene solution of trimethylaluminum (60 ml.) is added over a period of 4 min. to the resulting mixture. This mixture is then stirred for 1.5 hours at 20°–25° C. then cooled to 10° C. Thereupon 370 ml. of saturated ammonium chloride is slowly added at such a rate so as to maintain the reaction mixture at ambient temperature. After 0.5 hours the reaction mixture is diluted with ethyl acetate and water and filtered, the filter cake being washed with the ethyl acetate-water solvent. The aqueous layer is extracted with ethyl acetate and the combined organic extracts are washed with brine, dried over magnesium sulfate, and evaporated to yield crude product, which is chromatographed on one kg. of silica gel packed in 10 percent ethyl acetate and Skellysolve B. Elution with 10 to 16 percent ethyl acetate in Skellysolve B (18 l.), 28 percent ethyl acetate in Skellysolve B (8 l.) yields pure title compound or pure (3R)-epimer.

Omitting the chromatographic separation described above, the (3RS)-epimeric mixture obtained on trimethylaluminum alkylation are separated in high yield as prostaglandin-type products.

Following the procedure of Example 7, but using in place of the 2-chloro-3-oxo lactone starting material therein, the various lactones described following Example 4, there are obtained 2-chloro-3-hydroxy-3-methyl products corresponding to each of the 2-chloro-3-hydroxy products of Example 5.

EXAMPLE 8

3α,5α-dihydroxy-2β-[2-chloro-(3R)-3-hydroxy-4,4-dimethyl-trans-1-octenyl]-1α-cyclopentaneacetaldehyde, γ lactol, bis-tetrahydropyranyl ether (Formula XXVII: $R_3$ and $R_4$ of the $L_1$ moiety are methyl, $M_6$ is

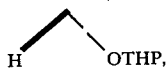

$R_7$ is n-butyl, $R_{18}$ is tetrahydropyran-2-yloxy, and $Y_2$ is trans—CH=C(Cl)—and its (3S)-epimer.

Refer to Chart A.

A. A solution of 100 mg. of the reaction product of Example 5 in 20 ml. of methanol is purged with nitrogen. Thereafter, potassium carbonate (30 mg.) is added and the resulting mixture is stirred at ambient temperature until thin layer chromatographic analysis shows the solvolysis to be complete (about 12 hours). The solution is then diluted with ice water and neutralized with cold, dilute phosphoric acid. The resulting mixture is then dried and evaporated under reduced pressure. The residue is then chromatographed using silica gel eluting with hexane and ethylacetate (3:2). Accordingly, 40 mg. of the deacylated lactone are prepared. NMR absorptions are observed at 0.92, 0.95, 1.1–1.6, 2.0–3.3, 4.02, 4.8–5.2, 5.57, and 5.66 δ.

B. A solution of 0.39 g. of the reaction product of part A above, in 25 ml. of methylene chloride (containing 1.2 ml. of dihydropyran and 1.2 mg. of a saturated solution of pyridine in methylene chloride) is allowed to stand for one hour at ambient temperature. Additional dihydropyran (1.2 ml.) is added and the reaction continued for 36 hours. The reaction mixture is then washed with water, aqueous sodium bicarbonate, dried, and evaporated, yielding an oil (0.371 g.), the bis-tetrahydropyranyl lactone corresponding to the lactone reaction product of part A above. NMR absorptions are observed at 0.6–1.05, 1.05–1.4, 1.4–1.9, 1.9–3.0, 3.0–4.3, 4.0, 4.3–5.2, and 5.48 δ.

C. A solution of the reaction product of part B above (0.39 g.) in 10 ml. of toluene is cooled to −70° C. and thereafter 10 ml. of 10 percent diisobutylaluminum hydride (1.64 mmoles) in toluene (10 ml.) is slowly added. The reaction mixture is then stirred at −70° C. until thin layer chromatographic analysis indicates that the reduction is complete (about 10 min.). Thereafter the cooling bath is removed and 9 ml. of a mixture of tetrahydrofuran and water (3:1) is added slowly. The reaction mixture is then stirred and allowed to warm to room temperature, and is then filtered through a cellulose bed. The filter cake is rinsed with benzene, combined organic extracts are then dried and evaporated to yield 0.40 g. of the title compound. NMR absorptions are observed at 0.7–1.05, 1.05–1.35, 1.35–1.9, 1.9–2.8, 2.8–4.2, 4.00, and 5.60 δ.

Following the procedure of Example 8, the 3α-benzoyloxy-5-hydroxy or 5-hydroxy lactones described in and following Examples 5, 6 and 7 are transformed into corresponding γ-lactols.

Following the procedure of Example 8 there is prepared from (3S) starting material, respectively:

1  3α,5α-Dihydroxy-2β-[2-chloro-(3S)-3S)-3-hydroxy-4,4-dimethyl-trans-1-octenyl]-1α-cyclopentaneacetic γ lactone. NMR absorptions are observed at 0.92, 1.1–1.7, 1.8–3.2, 3.2–3.5, 4.0, 4.8–5.2, and 5.66 δ. The mass spectrum shows peaks at 312, 233, 232, 231, 216, and 215.

2 3α,5α-Dihydroxy-2β-[2-chloro-(3S)-3-hydroxy-4,4-dimethyl-trans-1-octenyl]-1α-cyclopentaneacetic acid γ lactone bis-tetrahydropyranyl ether. NMR absorptions are observed at 0.6–1.05, 1.05–1.4, 1.4–2.0, 2.0–3.0, 3.0–4.4, 4.00, 4.4–5.7, and 5.48 δ.

3 3α,5α-Dihydroxy-2β[2-chloro-(3S)-3-hydroxy-4,4-dimethyl-trans-1-octenyl]-1α-cyclopentane acetaldehyde γ lactol bis-tetrahydropyranyl ether. NMR absorptions are observed at 0.6–1.1, 1.35–1.85, 1.85–3.0, 3.2–4.3, 4.00, 4.3–5.1, and 5.58 δ.

Further following the procedure of Example 8, but using the various lactones described following Examples 5 and 7 wherein $R_{16}$ is hydrogen, there are prepared the corresponding 5α-hydroxy-1α-cyclopentaneacetaldehyde γ lactol bis-tetrahydropyranyl ethers. Further following the procedure of Example 8, parts A and B, but using as starting material the various lactones described following Example 6, wherein $R_{16}$ is hydrogen, there are prepared the corresponding 5α-hydroxy-1α-cyclopentaneacetaldehyde γ lactols.

Further following the procedure of Example 8, but using as starting material the various lactols described following Example 5 and in and following Example 7, wherein $R_{16}$ is benzoyloxy, there are prepared the corresponding 3α,5α-dihydroxy-1α-cyclopentaneacetaldehyde γ lactol bis-tetrahydropyranyl ethers. Finally, following the procedure of Example 8, but using as starting material the various lactones described in the following Example 6, wherein $R_{16}$ is benzoyloxy, there are prepared the corresponding 3α,5α-dihydroxy-1α-cyclopentaneacetaldehyde γ lactol bis-tetrahydropyranyl ethers.

EXAMPLE 9

3-Oxa-14-chloro-PGF$_{1α}$, 11,15-bis-(tetrahydropyranyl ether), methyl ester (Formula XXXV: g is one, $R_3$ and $R_4$ of the $L_1$ moiety are hydrogen, $M_6$ is

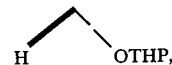

$R_7$ is n-butyl, $R_{18}$ is tetrahydropyranyloxy, and $Y_2$ is trans—CH=C(Cl)—) or its 15-epimer.

Refer to Chart B.

A. 3α,5α-Dihydroxy-2β-[2-chloro-(3S)-3-hydroxy-trans-1-octenyl]-1α-cyclopentaneacetaldehyde γ-lactol, bis-tetrahydropyranyl ether, (10.0 g.) is dissolved in 150 ml. of absolute ethanol (containing 3 drops of acetic acid). To this solution is added carbethoxymethylenetriphenylphosphorane (10 g.) and the mixture is stirred at ambient temperature for 72 hours. The resulting mixture is concentrated under reduced pressure to a volume of about 35 ml., mixed with ice, and dilute sodium bicarbonate solution, and shaken with ethyl acetate. The organic phase is washed with brine, dried over magnesium sulfate, and concentrated to yield a residue. The residue is slurried in 100 ml. of diethyl ether and filtered. The filtrate is concentrated to a residue which is subjected to silica gel chromatography, eluting with 20 to 40 percent ethyl acetate in Skellysolve B. There is obtained 2,3,4-trinor-14-chloro-PGF$_{2α}$, ethyl ester, bis(-tetrahydropyranyl)ether.

B. The reaction product of step A above is mixed with the 5 percent palladium-on-charcoal catalyst (0.3 g.) in 30 ml. of ethyl acetate and hydrogenated at atmospheric pressure. When about one equivalent of hydrogen is consumed, the catalsyt is filtered off and the filtrate concentrated under reduced pressure to yield 2,3,4-trimor-14-chloroPGF$_{1\alpha}$, ethyl ester, bis(tetrahydropyranyl)ether.

C. The reaction product of step B above (1.1 g.) in 30 ml. of diethyl ether is added with stirring to a mixture of lithium aluminum hydride (0.3 g.) in 60 ml. of diethyl ether. The addition continues over a 10 min. period. The mixture is heated at reflux for 2 hours then cooled, and treated with 0.35 ml. of water cautiously added. Thereafter 0.35 ml. of 15 percent aqueous sodium hydroxide solution is added, and thereafter one ml. of water. The solids are removed by filtration and filtrate is concentrated under reduced pressure to yield 2-decarboxy-2-hydroxymethyl-2,3,4-trinor-14-chloro-PGF$_{1\alpha}$, bis-tetrahydropyranyl ether.

D. The reaction product of part C above (1.7 g.) together with 15 ml. of dimethyl sulfoxide and 5 ml. of tetrahydrofuran is treated with 2.28 ml. of 1.6 molar n-butyllithium in hexane, with stirring and cooling. After 5 min. there is added 5 ml. of dimethylformamide. The resulting solution is then stirred and cooled to 0° C. Thereafter lithium chloroacetate (0.7 g.) is added. The mixture is then stirred at 0° C. for 2 hours and at about 25° C. for 22 hours. Thereafter the resulting solution is diluted with 200 ml. of ice-water, acidified with a cold solution of 3 ml. of concentrated hydrochloric acid in 50 ml. of water, and immediately extracted with dichloromethane. The organic phase is washed with cold water and brine and dried over magnesium sulfate. Accordingly, there is prepared 3-oxa-14-chloro-PGF$_{1\alpha}$, 11,15-bis-tetrahydropyranyl ether.

E. To the above solution is added excess ethereal diaxomethane and after a few minutes the excess reagent is destroyed with acetic acid. The mixture is then washed with a mixture of sodium bicarbonate solution and brine and thereafter with brine. The resulting solution is then dried and concentrated under reduced pressure. The residue so obtained is subjected to silica gel chromatography eluting with ethyl acetate and Skellysolve B to yield the title compounds.

Following the procedure of Example 9, but using the (3R) starting material there is obtained the corresponding 15-epi product.

Following the procedure of Example 9, but using the various lactols described following Example 8, there are obtained the corresponding products. For those lactols described following Example 8, wherein the C-3 position of the cyclopentane ring is unsubstituted (R$_{18}$ is hydrogen), there are obtained the corresponding 11-deoxy products wherein the C-11 position is not etherified. When the 3-methoxy lactones described following Example 8 are employed there are obtained the corresponding 14-chloro-prostaglandintype compounds wherein the C-15 position is methoxy-substituted.

Following the procedure of Example 9, but omitting the etherification step (part E) there are obtained the above compounds in free acid form.

Following the procedure of Example 9, but replacing lithium chloroacetate used in part D of Example 9 with lithium chloropropionate or lithium chlorobutyrate, there are obtained the corresponding 3-oxa-14-chloro-PGF$_{1\alpha}$-type compounds wherein g is 2 or 3. Further, using the various lactols described following Example 8, there are obtained the corresponding 3-oxa-14-chloro-PGF$_{1\alpha}$-type compounds wherein g is 2 or 3 when the above chloroalkanoates are substituted for lithium choloroacetate.

EXAMPLE 10

5-Oxa-14-chloro-PGF$_{1\alpha}$, methyl ester, 11,15-bis-(tetrahydropyranyl) ether (Formula XLIII: g is one, R$_3$ and R$_4$ of the L$_1$ moiety are hydrogen, M$_6$ is

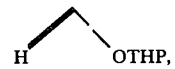

R$_1$ is methyl, R$_7$ is n-butyl, R$_{18}$ is tetrahydropyranyloxy, and Y$_2$ is trans—CH=C(Cl)—) or its 15-epimer.

Refer to Chart C.

A. A mixture of lactol starting material of Example 9 (6.3 g.) and 50 ml. of 95 percent ethanol is treated at 0° C. with stirring with a solution of sodium borohydride in 10 ml. of water (added over a period of one minute). The resulting mixture is then stirred at 0° C. for 10 minutes and then shaken with 10 ml. of water, 250 ml. of ethyl acetate, and 150 ml. of brine. The organic phase is then washed with brine, dried, and concentrated under reduced pressure to yield 2-decarboxy-2-hydroxymethyl-2,3,4,5,6-pentanor-14-chloro-PGF$_{1\alpha}$, 11,15-bis-tetrahydropyranyl ether.

B. A solution of potassium tert-butoxide (1.77 g.) in 30 ml. of tetrahydrofuran is mixed at 0° C., with stirring, with a solution of the reaction product of part A (5.8 g.) in 30 ml. of tetrahydrofuran. The resulting mixture is then stirred at 0° C. for 5 minutes and thereafter 5 ml. of trimethyl ortho-4-bromobutyrate is added. Stirring is continued at 0° C. for 2 hours and at about 25° C. for 16 hours. To this mixture is added 30 ml. of dimethylformamide and 0.5 g. of potassium-t-butoxide. The resulting mixture is then stirred for 20 hours. Some of the solvent is then removed under reduced pressure and the residue is then shaken with water and diethyl ether and dichloro methane (3:1). The organic phase is then washed with water and brine, dried, and concentrated. The residue, containing the ortho ester, is dissolved in 6 ml. of methanol at 0° C. and treated with 15 ml. of cold water containing 2 drops of concentrated hydrochloric acid. The resulting mixture is then stirred at 0° C. for 5 minutes, shaken with 200 ml. of diethyl ether, 50 ml. of dichloromethane, and 200 ml. of brine. The organic phase is then washed with brine, dried, and concentrated under reduced pressure. The residue is subjected to silica gel chromatography, yielding the title compounds.

C. Trimethylortho-4-butyrate is prepared as follows:

Refer to S. M. McEldian, et al., Journal of the American Chemical Society 64, 1825 (1942). A mixture of 4-bromobutyronitrile (74 g.), 21 ml. of methanol, and 150 ml. of diethyl ether is treated at 0° C. with stirring, with hydrogen bromide (40 g.). The mixture is then stirred for an additional 4 hours at 0° C. and 100 ml. of hexane is added. The precipitated imino ester hydrobromide is separated from the liquid by filtration and washed with 400 ml. of diethyl ether in hexane (1:1). The imino ester salt is treated in 250 ml. of diethyl ether with 150 ml. of methanol and 25 ml. of methyl orthoformate, with stirring, at about 25° C. for 24 hours. The resulting mixture is then cooled to about 10° C. and the organic solution is separated from the ammonium bromide thereby formed. Diethyl ether (100 ml.) is then added. The resulting solution is then immediately and quickly washed with an ice cold solution prepared from potassium carbonate (20 g.) and 300 ml. of brine. The organic phase is washed with brine, treated with 3 drops of pyridine, and dried over anhydrous magnesium sulfate. The solution is then concentrated under reduced pressure, diluted with 150 ml. of benzene, and again concentrated. The residue is then distilled to yield the title ortho-4-bromobutyrate.

Following the procedure of part C of Example 10, but using 5-bromo pentanonitrile or 6-bromo hexanonitrile there is prepared trimethylortho-5-bromo pentanoate or trimethylortho-6-bromo hexanoate.

Following the procedure of Example 10, but using the corresponding (3R) lactone, there is obtained the corresponding 15-epi-PGF$_{1\alpha}$-type product.

Following the procedure of Example 10, but using any of the various lactols described following Example 8, there is prepared the corresponding 5-oxa-14-chloro-PGF$_{1\alpha}$-type product. For those lactols wherein the C-3 position of the cyclopentane ring is unsubstituted ($R_{18}$ is hydrogen), the corresponding 11-deoxy-PGF$_{1\alpha}$-type product produced is not etherified at the C-11 position. For those lactols described following Example 8, wherein the C-3 position of the side chain contains a methoxy group, the corresponding 3-oxa-14-chloro-13-PGF$_{1\alpha}$-type product contains no tetrahydropyranyl ether at the C-15 position.

Further, following the procedure of Example 10, but using trimethylortho-5-bromopentanoate or trimethylortho-6-bromohexanoate there is prepared by corresponding 5-oxa-14-chloro-PGF$_{1\alpha}$-type product wherein g is 3 or 4. Likewise using the various lactols described following Example 8, corresponding 2a-homo or 2a,2b-dihomo products are obtained.

EXAMPLE 11

4-Oxa-14-chloro-PGF$_{1\alpha}$ 11,15-bis(tetrahydropyranyl)ether (Formula LVIII: g is one, $R_3$ and $R_4$ of the $L_1$ moiety are hydrogen, $M_6$ is

$R_1$ is hydrogen, $R_7$ is n-butyl, $R_{18}$ is tetrahydropyranyloxy, and $Y_2$ is trans—CH=C(Cl)—).

Refer to Chart D.

A. A suspension of methoxymethyltriphenylphosphonium chloride (32.4 g.) in 150 ml. of tetrahydrofuran is cooled to −15° C. To the suspension is added 69.4 ml. of n-butyllithium in hexane (1.6 molar) in 45 ml. of tetrahydrofuran. After 30 minutes there is added a solution of 3α,5α-dihydroxy-2β-[2-chloro-(3S)-3-hydroxy-trans-1-octenyl]-1α-cyclopentaneacetaldehyde γ lactol bis-(tetrahydropyranyl)-ether, (10 g.), in 90 ml. of tetrahydrofuran. The mixture is stirred for 1.5 hours while warming to 25° C. The resulting solution is thereafter concentrated under reduced pressure. The residue is partitioned between dichloromethane and water, the organic phase being dried and concentrated. This dry residue is then subjected to chromatography over silica gel eluting with cyclohexane and ethyl acetate (2:1). Those fractions as shown by thin layer chromatography to contain pure formula LII product are combined.

B. The reaction product of part A above in 20 ml. of tetrahydrofuran is hydrolyzed with 50 ml. of 66 percent aqueous acetic acid at about 57° C. for 2.5 hours. The resulting mixture is then concentrated under reduced pressure. Toluene is added to the residue and the solution is again concentrated. Finally the residue is subjected to chromatography on silica gel, eluting with chloroform and methanol (6:1). The title compound is thereby obtained by combining and concentrating fractions as shown by thin layer chromatography to contain pure product. Accordingly, there is obtained the corresponding formula LIII δ-lactol.

C. Silver oxide is prepared by the addition of silver nitrate (1.14 g.) in water (3 ml.) dropwise to a 2 normal sodium hydroxide solution (6.8 ml.). A precipitate is formed. Added to the precipitate in ice water bath is the δ lactol of part B above (1 g.) in tetrahydrofuran (4 ml.). When the addition is complete, the ice bath is removed and the reaction mixture allowed to warm to ambient temperature. When the reaction is complete, as shown by thin layer chromatography (chloroform and methanol), (9:1), impurities are removed by filtration. The filtrate is then extracted with diethyl ether. The aqueous layer is then chilled in an ice bath and acidified with 10 percent potassium bisulfate solution to pH less than 2. This aqueous mixture is then extracted with diethyl ether. The ethereal extracts are then combined, washed with brine, dried over magnesium sulfate, filtered, and evaporated under reduced pressure to yield the formula LIV lactone.

D. The formula LIV lactone prepared in part C above is then transformed to its bis-tetrahydropyranyl ether derivative following the procedure described in Example 8, part B.

E. The formula LV compound prepared in part D above is then reduced to the corresponding δ lactol bis-tetrahydropyranyl ether by the procedure described in Example 8, part C.

F. The formula LVI lactol prepared in part E above is then transformed to the corresponding formula LVII primary alcohol by the procedure described in Example 10, part A.

G. The formula LVIII compound is prepared from the formula LVII compound by etherification of the primary alcohol moiety following the procedure described in Example 10, part B, but by substituting trimethylortho-3-bromopropionate in place of trimethylortho 4-bromobutyrate.

Following the procedure of Example 11, but using the corresponding (3R) starting material in places of the (3S) starting material there is obtained the corresponding 15-epi-PGF$_{1\alpha}$-type product.

Following the procedure of Example 11, but using in step G, trimethyl ortho-4-bromobutyrate or ortho-5-bromopentanoate in place of trimethylortho-3-bromopropionate, there are obtained the corresponding formula LVIII compound wherein g is 2 or 3.

Following the procedure of Example 11, but using in place of the formula LVI lactol, the various formula XXVII lactols described following Example 8, there are obtained the corresponding 4-oza-14-chloro-PGF$_{1\alpha}$-type products. Finally using the above ortho-ω-alkanoates there are prepared corresponding 2a-homo or 2a,2b-dihomo compounds.

EXAMPLE 12 cis-4,5-Didehydro-14-chloro-PFG$_1\alpha$, 11,15-bis(tetrahydropyranyl) ether (Formula LIX: g is one, $R_3$ and $R_4$ of the $L_1$ moiety are hydrogen, $M_6$ is

$R_1$ is hydrogen, $R_7$ is n-butyl, $R_{18}$ is tetrahydropyranyloxy, and $Y_2$ is trans—CH=C(Cl)—) and its 15-epimer.

Refer to Chart D.

A. Following the procedure of Example 11, parts A, B, C, D, and E there is prepared the formula LVI lactol wherein $L_1$, $M_6$, $R_7$, $R_{18}$, and $Y_2$ are as defined for the title compound.

B. 3-Carboxypropyltriphenylphosphonium bromide (prepared by heating 4-bromobutyric acid and triphenylphosphine in benzene at reflux for 18 hours, and thereafter purifying), 106 g., is added to sodiomethylsulfinylcarbanide prepared from sodium hydride (2.08 g., 57 percent) and 30 ml. of dimethylsulfoxide. The resulting Wittig reagent is combined with the formula LVI lactol of part A above and 20 ml. of dimethylsulfoxide. The mixture is stirred overnight, diluted with about 200 ml. of benzene, and washed with potassium hydrogen sulfate solution. The two lower layers are washed with dichloromethane, the organic phases are combined, washed with brine, dried, and concentrated under reduced pressure. The residue is subjected to chromatography over acid washed silica gel, eluting with ethyl acetate and isomeric hexanes (3:1). Those fractions as shown to contain the desired compound by thin layer chromatography are combined to yield pure product.

Following the procedure of Example 12, but using in place of the (3S) starting material the corresponding (3R) starting material there is obtained the corresponding 15-epi-14-chloro-PGF$_1\alpha$-type compound.

Following the procedure of Example 12, but using in place of the 3-carboxypropyltriphenylphosphonium bromide, 4-carboxybutyltriphenylphosphonium bromide, or 5-carboxypentyltriphenylphosphonium bromide, there are prepared the corresponding formula LIX compounds wherein g is 2 or 3.

Further, following the procedure of Example 12, but using in place of the formula LI starting material the various formula XXVII lactols described following Example 8, there are prepared the corresponding cis-4,5-didehydro-14-chloro-PGF$_1\alpha$- or 11-deoxy-$_1\alpha$-type products.

EXAMPLE 13

14-Chloro-16,16-dimethyl-PGF$_2\alpha$, methyl ester, 11,15-bis-tetrahydropyranyl ether (Formula LXII : g is 1, $R_3$ and $R_4$ of the $L_1$ moiety are methyl, $M_6$ is

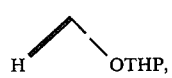

$R_1$ is methyl, $R_2$ is hydrogen, $R_7$ is n-butyl, $R_{18}$ is tetrahydropyranyloxy, and $Y_2$ is trans-CH=C(Cl)-) or its 15-epimer.

Refer to Chart E.

A. Sodium hydride (0.40 g., 57 percent in mineral oil in 20 ml. of dimethylsulfoxide, is added to 1.82 g. of 4-carboxybutyltriphenylphosphonium bromide. The reaction mixture is maintained at 20° C. with stirring for 25 min. A solution of the title compound of Example 8 (0.39 g.) in 10 ml. of toluene is added. The reaction mixture is stirred at ambient temperature for 2 hours and diluted with benzene. Potassium bisulfate (2.7 g. in 30 ml. of water) is slowly added, maintaining the reaction temperature at less than or equal to 10° C. The aqueous layer is extracted with 50 ml. of benzene and the organic extracts are washed successfully with 50 ml. of water and 50 ml. of brine before combining, drying, and evaporating. Evaporation yields semi-crystalline residue which is chromatographed on 100 g. of acid washed silica gel eluting 20 percent ethyl acetate m-hexane. Thereby 0.241 g. of the pure free acid of the title product is obtained. NMR absorptions are observed at 0.65–1.1, 1.1–1.4, 1.4–1.8, 1.8–2.6, 2.8–4.4, 4.05, 4.4–4.8, 5.2–5.75, and 6.0–6.9 δ.

B. A solution of the reaction product of part A above and 15 ml. of diethyl ether is esterified with diazomethane, used in stoichiometric excess. The crude methyl ester is chromatographed on 100 g. of silica gel packed in 2 percent acetone methylene chloride. Elution with 2-12 percent acetone in methylene chloride yields the title compound.

Following the procedure of Example 13, but using the (3R) lactol there is obtained the corresponding 15-epi-14-chloro-PGF$_2\alpha$, methyl ester, 11,15-bis-tetrahydropyranyl ether. NMR absorptions are observed at 0.7–1.1, 1.1–1.4, 1.4–1.8, 1.8–2.55, 3.15–4.2, 3.66, 4.05, 4.5–4.8, 5.2–5.8, and 5.6 δ.

Following the procedure of Example 13, but using 5-carboxypentyltriphenylphosphonium bromide or 6-carboxyhexyl-triphenylphosphonium bromide in place of 4-carboxybutyltriphenylphosphonium bromide there is obtained the corresponding 2a-homo or 2a,2b-dihomo-14-chloro-PGF$_2\alpha$-type compound or its 15-epimer.

Further, following the procedure of Example 13, but using in place of 4-carboxybutyltriphenylphosphonium bromide, 4,4-difluoro-4-carboxybutyltriphenylphosphonium bromide there is obtained the corresponding 2,2-difluoro-14-chloro-PGF$_2\alpha$-type tetrahydropyranyl ether or its 15-epimer.

Further, following the procedure of Example 13, but using in place of the formula LXI lactol starting material therein one of the various lactols described following Example 8, and optional by any of the Wittig reagents described above, there are prepared the corresponding 14-chloro or 11-deoxy-14-chloro-PGF$_2\alpha$-type products.

EXAMPLE 14 15-Methyl-14-chloro-PGF$_2\alpha$, methyl ester (Formula LXXVI: $R_3$ and $R_4$ of the $L_1$ moiety are hydrogen, $M_1$ is

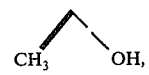

$M_{18}$ is

$R_1$ is methyl, $R_7$ is n-butyl, $R_8$ is hydroxy, $Y_2$ is trans—CH=C(Cl)—, and $Z_2$ is cis—CH=CH(CH$_2$)$_3$—) or its 15-epimer.

A. A solution of 5.7 g. of the reaction product of Example 7, α-benzoyloxy-5α-hydroxy-2β-[(3S)3-hydroxy-3-methyl-cis-1-octenyl]-1α-cyclopentaneacetic acid γ lactone in 150 ml. of methanol is deacylated according to the procedure of Example 8, part A, yielding of 3α,5α-dihydroxy-2β-[2-chloro-(3S)-3-hydroxy-3-methyl-trans-1-octenyl]-1α-cyclopentaneacetic acid γ lactone.

A sample of the corresponding (3R) starting material is deacylated in a similar fashion, yielding the corresponding (3R) product.

B. A solution of 3.65 g. of the reaction product of part A in 150 -carboxybutyltriphenylphosphonium m. of tetrahydrofuran is cooled to −60° C. Diisobutylaluminum hydride and toluene (85 ml.) is added over a period of 23 minutes at a temperature of −70° C. The reaction mixture is stirred for an additional 24 minutes. Thereafter 100 ml. of saturated aqueous ammonium chloride solution is slowly added at a temperature of −60° C. The resulting mixture is then stirred and allowed to warm to room temperature, yielding a gelatin as precipitate. This mixture is then diluted with 70 ml. of water and 150 ml. of ethyl acetate, mixed thoroughly and filtered. The filter cake is washed with water and ethyl acetate. The aqueous layer is extracted with ethyl acetate. The combined organic extracts are washed with brine, dried over sodium sulfate, and evaporated to yield the lactol corresponding to lactone starting material.

C. Following the procedure of Example 13, sodium hydride in dimethylsulfoxide is combined with 4-carbosybutyltriphenylphosphonium bromide to yield the title compound in free acid form.

The reaction product of part C above is esterified with diazomethane following the procedure described above, yielding the title compound.

Following the procedure of steps B-D above, but using the deacylated (3R)-lactone there is obtained 1.15-epi-15-methyl-14-chloro-PGF$_{2\alpha}$,methyl ester.

The preparation of the above title compound or its 15-epimer is optionally accomplished following the procedure of Chart F. Accordingly, the 3(RS)-3-methyl lactone corresponding to Example 7 is prepared by omitting the chromatographic separation step therein. Thereafter, by the procedure of Example 8 the corresponding 3(RS)-3-methyl lactol is prepared. Thereafter, following the procedure of Example 13, the (15RS)-15-methyl-14-chloro-PGF$_{2\alpha}$-bistetrahydropyranyl ether, methyl ester is prepared by methyl esterification of the free acid so formed. The tetrahydropyranyl ether moieties may then be hydrolyzed and the C-15 epimers separated by chromatographic techniques.

Following the procedure of Example 14, or the optional procedure discussed above, there are prepared 15-epi-15-methyl or 15-methyl-PGF$_{2\alpha}$-type compounds from the corresponding lactols described following Example 8.

Further, using the compounds described in or following Examples 9, 10, 11, 12, or 13 there are prepared the corresponding 3-oxa-, 4-oxa-, 5-oxa-, or cis-4,5-didehydro-15-methylor 15-epi-15-methyl-14-chloro-PGF$_{2\alpha}$-type products.

EXAMPLE 15 15-Methyl-14-chloro-PGF$_{2\alpha}$ (Formula LXXVI: R$_3$ and R$_4$ of the L$_1$ moiety are hydrogen, M$_1$ is

M$_{18}$ is

R$_1$ is hydrogen, R$_7$ is n-butyl, R$_8$ is hydroxy, Y$_1$ is trans—CH=C(Cl)—, and A$_2$ is cid—CH—(CH$_2$)$_3$—) or its 15-epimer.

A solution of 2.0 g. of the reaction product of Example 14, or its 15-epimer, in 20 ml. of methanol is cooled to 0° C. The resulting mixture is thereafter treated cropwise under a nitrogen atmosphere with 12 ml. of 10 percent aqueous sodium hydroxide solution. The mixture is then allowed to warm to room temperature and stirred for 2 hours. After removal of the methanol by evaporation under reduced pressure the residue is diluted with water and extracted with methylene chloride. The aqueous layer is then cooled with ice, treated with 24 ml. of 2 molar aqueous sodium bisulfate solution and extracted immediately with ethyl acetate. The combined organic extracts are washed with brine, dried over anhydrous sodium sulfate, and concentrated. Crude product may then be chromatographed on 150 g. of silica gel, yielding the title compound or its 15-epimer.

Following the procedure of Example 15, but using any of the 15-methyl-14-chloro-PGF α or 11-deoxy-15-methyl-14-chloro-PGF α-type methyl esters, there are prepared the corresponding free acid products.

EXAMPLE 16

14-Chloro-16,16-dimethyl-PGF2α methyl ester (Formula LXXVI: R$_3$ and R$_4$ of the L$_1$ moiety are methyl, M$_1$ is

M$_{18}$ is

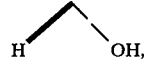

R$_1$ is methyl, R$_7$ is n-butyl, R$_8$ is hydroxy, Y$_1$ is trans—CH=C(Cl)—, and Z$_2$ is cis—CH=CH—(CH$_2$)$_3$—) or its 15-epimer.

Refer to Chart F.

14-Chloro-16,16-dimethyl-PGF$_{2\alpha}$-bis-tetrahydropyranyl ether (0.241 g.) is reacted with 20 ml. of tetrahydrofuran, water, and acetic acid (1:3:6) at 40° C. for 4 hours. Thereafter, the resulting mixture is diluted with 60 ml. of water andlyophylized. The residue is then esterified with diazomethane, quenching with ethereal acetic acid, and thereafter washing with sodium bicarbonate and brine, drying and evaporating to a residue. The chromatographed (eluting with methylene chloride and acetone, 3:1) residue yields 0.056 g. of pure product. NMR absorptions are observed at 0.44, 0.98, 1.1–1.42, 1.42–2.6, 2.7–3.4, 3.7, 3.8–4.5, 4.04, 5.25–5.8, and 5.65 δ. The mass spectrum shows peaks at 395, 340, 331, 296, and 281. Characteristic ester IR absorptions are observed at 1550, 1577, 1760, and 3450 cm$^{-1}$.

Using corresponding 15-epimeric starting material the corresponding 15-epimeric product is prepared.

Following the procedure of Example 16, but using as starting material any of the 11,15-bis-tetrahydropyranyl ethers, 11-tetrahydropyranyl ethers, or 15-tetrahydropyranyl esters described in and following Examples 9, 10, 11, 12, or 13, there are prepared respectively the corresponding 14-chloro-PGF$_{2\alpha}$-15-methyl ether, 14-chloro-PGF$_{2\alpha}$-, or 11-deoxy-14-chloro-PGF$_{2\alpha}$, 15-methyl ether or 11-deoxy-14-chloro-PGF$_{2\alpha}$-type compounds.

EXAMPLE 17

15-Methyl-14-chloro-PGE$_2$, methyl ester, (Formula LXXVI: R$_3$ and R$_4$ of the L$_1$ moiety and P$_6$ of the M$_1$ moiety are hydrogen, M$_{18}$ is

R$_1$ and R$_5$ are methyl, R$_7$ is n-butyl, R$_8$ is hydroxy, Y$_2$ is trans—CH=C(Cl), and Z$_2$ is cis—CH=CH—(CH$_2$)$_3$—) or its 15-epimer.

A. A solution of 15-methyl-14-chloro-PGF$_{2\alpha}$, methyl ester, 11,15-bis-tetrahydropyranyl ether, prepared above, in 60 ml. of acetone is cooled to −25° C. Thereupon 1.9 ml. of Jones reagent is added. The reaction mixture is then stirred for 25 minutes at −25° C. and isopropyl alcohol (1.9 ml.) is added after an additional 15 minutes at −25° C. the reaction mixture is diluted with 200 ml. of water (0° C.) and extracted with diethyl ether. Ethereal extracts are washed with 75 ml. of cold 0.1 normal potassium bicarbonate, 150 ml. of brine, dried over magnesium sulfate, and evaporated, thereby yielding 15-methyl-14-chloro-PGE$_2$, methyl ester, 11,15-bis-tetrahydropyranyl ether.

B. A solution of the crude product of part A above is reacted with 16 ml. of tetrahydrofuran, water, and acetic acid (1:3:6) and allowed to stand at 40° C. for 4 hours. The resulting mixture is thereafter diluted with 120 ml. of water and freeze dried. The residue is dissolved in diethyl ether and washed with potassium bicarbonate, brine, and thereafter dried and evaporated to yield crude product. The crude product is chromatographed on 25 g. of silica gel packed in 5 percent acetone in methylene chloride. Elution with 5 to 40 percent acetone in methylene chloride yields the pure product.

Following the above procedure but using 15-epimeric starting material, the corresponding 15-epimer is prepared.

Following the procedure of Example 17, but using the various 15-methyl-14-chloro-PGF$_\alpha$ or 11-deoxy-PGF$_\alpha$ methyl ester, 11,15-bis tetrahydropyranyl ethers, or 15-tetrahydropyranyl ethers, as prepared in or following Examples 9, 10, 11, 12, and 13 there are prepared the corresponding 15-methyl-14-chloro-PGE or 11-deoxy-14-chloro-PGE-type products.

EXAMPLE 18

15-Methyl-14-chloro-PGE$_2$ or its 15-epimer.

The title compound is prepared by enzymatic hydrolysis of the methyl ester of the reaction product of Example 17 or its 15-epimer.

The enzyme is prepared as follows:

Freshly narvested colony pieces of Plexaura homomalla (Esper), 1792, forma S (10 kg.), are chopped into pieces less than 3 cm. in their longest dimension and then covered with about 3 volumes (20 l.) of acetone. The mixture is stirred at about 25° C. for one hour. The solids are separated by filtration, washed with a quantity of acetone, air dried, and finally stored at about 20° C. as a coarse enzymatic powder.

The esterase hydrolysis then proceeds as follows:

The suspension of the esterase composition prepared above in 25 ml. of water is combined with the solution of the above indicated starting material. 8 ml. of methanol is added, and the resulting mixture is stirred at about 25° C. for 24 hours. 50 ml. of acetone is then added and the mixture is stirred briefly, filtered, and the filtrate is then concentrated under reduced pressure. The aqueous residue is then acidified to pH 3.5 with citric acid and extracted with dichloromethane. The combined extracts are concentrated under reduced pressure to yield the title acid.

Following the procedure of Example 18, but using the various methyl esters described following Example 17, the corresponding products are prepared.

EXAMPLE 19

14-Chloro-PGF$_{1\alpha}$, methyl ester, or its 15-epimer.

A solution of 4.8 g. of 14-chloro-PGF$_{2\alpha}$, methyl ester in 90 ml. of acetone and 60 ml. of benzene containing 0.75 g. of tris(triphenylphosphine)rhodium (I) chloride is shaken under hydrogen atmosphere at ambient temperature at 1 to 3 atmospheres pressure for 3.5 hours. Thereafter the solvent is evaporated and the residue chromatographed on 400 g. of silica gel packed in methylene chloride eluting with one to 6 percent methanol in methylene chloride. There is recovered 0.90 g. of impure product. The above product is purified using silica gel chromatography, thereby preparing pure product.

Following the above procedure, but using 15-epi-14-chloro-PGF$_{2\alpha}$, methyl ester, there is prepared the corresponding 15-epi-14-chloro-PGF$_{1\alpha}$, methyl ester.

Following the procedure of Example 20, but using in place of the indicated starting material any of the PGF$_{2\alpha}$ or 11-deoxy-PGF$_{2\alpha}$-type compounds described in or following Example 13, there are prepared the corresponding PGF$_{1\alpha}$ or 11-deoxy-PGF$_{1\alpha}$-type products.

EXAMPLE 20

14-Chloro-PGE$_1$, methyl ester, or its 15-epimer.

The title compound of this Example is prepared by oxidation of the compound of Example 19, using the procedure described in Example 17, part A.

Using the corresponding 15-epimer, there is prepared 15-epi-14-chloro-PGE$_1$, methyl ester.

Following the procedure of Example 20, but using any of the 11-deoxy-PGF$_{1\alpha}$- or PGF$_{1\alpha}$-type compounds described following Example 19, there are prepared the corresponding 11-deoxy-PGE$_1$- or PGE$_1$-type compounds.

Accordingly, following the procedures of Examples 14-20 there are prepared the various 14-chloro-PGF$_{2\alpha}$-, 2,2-difluoro-PGF$_{2\alpha}$-, 2a, 2b-dihomo-PGF$_{2\alpha}$-, 3-oxa-PGF$_{1\alpha}$-, 5-oxa-PGF$_{1\alpha}$-, 4-oxa-PGF$_{1\alpha}$-, cis-4,5-didehydro-PGF$_{1\alpha}$-, PGF$_{1\alpha}$-, 2,2-difluoro-PGF$_{1\alpha}$-, or 2a,2b-dihomo-PGF$_{1\alpha}$-type compounds or the corresponding PGE-type compounds, optionally substituted at C-15 with methyl or methoxy, at C-16 with one or 2-methyl, or one or 2 fluoro, or phenoxy, or optionally substituted at C-17 with a phenyl or substituted phenyl moiety.

EXAMPLE 21

14-Chloro-16,16-dimethyl-PGF$_{2\beta}$, methyl ester (Formula LXXVII: R$_3$ and R$_4$ of the L$_1$ moiety are methyl, M$_1$ is

$R_1$ is methyl, $R_7$ is n-butyl, $R_8$ is hydroxy, $Y_2$ is trans—CH=C(Cl)—, and $Z_2$ is cis—CH=CH—(CH$_2$)$_3$-).

Refer to Chart F.

A solution of 0.3 g. of 14-chloro-16,16-dimethyl-PGE$_2$, methyl ester, in 15 ml. of methanol is cooled to −15° C. Thereafter 16 mg. of borohydride is added. After 45 minutes, 2 ml. of 50 percent acetic acid in water is slowly added. The reaction mixture is then allowed to warm to ambient temperature and then evaporated at reduced pressure. The residue is then shaken with ethyl acetate and water. The organic phase is then washed with aqueous sodium bicarbonate, brine, and then dried and evaporated to yield crude product. A column of 25 g. of silica gel packed in ethyl acetate is eluted with 70–100 percent ethyl acetate in cyclohexane. Crude product is then rechromatographed eluting with 0.5 to 3 percent methanol in methylene chloride. Rechromatographing yields the 9β-epimer.

Using the corresponding 15-epimeric starting material the corresponding 15-epimeric product is prepared.

Following the procedure of Example 21, but using the various PGE$_2$-, 11-deoxy-PGE$_2$-, PGE$_1$-, or 11-deoxy-PGE$_1$-type compounds described in the preceding examples, there are obtained the corresponding PGF$_{2\beta}$, 11-deoxy-PGF$_{2\beta}$, PGF$_{1\beta}$, or 11-deoxy-PGF$_{1\beta}$-type compounds.

EXAMPLE 22

14-Chloro-16,16-dimethyl-PGA$_2$ (Formula LXXVIII: $R_3$ and $R_4$ of the $L_1$ moiety are methyl, $M_1$ is

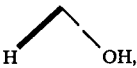

$R_1$ is hydrogen, $R_7$ is n-butyl, $Y_2$ is trans—CH=C(Cl)—, and $Z_2$ is cis—CH=CH—(CH$_2$)$_3$—). Refer to Chart F.

A solution of 14-chloro-16,16-dimethyl-PGE$_2$ (300 mg.), 4 ml. of tetrahydrofuran, and 4 ml. of 0.5 normal hydrochloric acid is left standing at ambient temperature for 5 days. Brine and dichloromethane in ether (1:3) are added and the mixture is stirred. The organic phase is separated, dried, and concentrated. The residue is dissolved in diethyl ether and the solution is extracted with aqueous sodium bicarbonate. The aqueous phase is acidified with dilute hydrochloric acid and then extracted with dichloromethane. This extract is then dried and concentrated to yield the title compound.

Following the procedure of Example 22, but using any of the PGE$_2$- or PGE$_1$-type compounds described above there are respectively prepared the corresponding PGA$_2$- or PGA$_1$- type compounds.

EXAMPLE 23

14-Chloro-16,16-dimethyl-PGB$_2$ (Formula LXXIX: $R_3$ and $R_4$ of the $L_1$ moiety are methyl, $M_1$ is

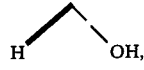

$R_1$ is hydrogen, $R_7$ is n-butyl, $Y_2$ is trans—CH=C(Cl)—, and $Z_2$ is cis—CH=CH—(CH$_2$)$_3$—).

Refer to Chart F.

A solution of 14-chloro-16,16-dimethyl-PGE$_2$ (200 mg.) and 100 ml. of 50 percent aqueous methanol containing about 1 g. of potassium hydroxide is kept at ambient temperature for 10 hours under nitrogen atmosphere. The resulting solution is then cooled to 10° C. and neutralized by addition of 3 normal hydrochloric acid at 10° C. This solution is then extracted repeatedly with ethyl acetate and the combined organic extracts are washed with water, then washed with brine, dried, and concentrated to yield the title compound.

Following the procedure of Example 23, but using any of the PGE$_2$ or PGE$_1$-type compounds described in the above Examples, there are prepared the corresponding PGB$_2$ and PGB$_1$-type compounds.

EXAMPLE 24

14-Chloro-16,16-dimethyl-PGF$_{2\alpha}$ sodium salt.

A solution of 14-chloro-16,16-dimethyl-PGF$_{2\alpha}$ (100 mg.) in 50 ml. of water ethanol mixture (1:1) is cooled at 5° C. and neutralized with an equivalent amount of .1 normal aqueous sodium hydroxide solution. The neutral solution is then concentrated to a residue of the title compound.

Following the procedure of Example 24, using potassium hydroxide, calcium hydroxide, tetramethyl ammonium hydroxide, or benzyltrimethylammonium hydroxide in place of sodium hydroxide there is obtained the corresponding salts of 14-chloro-16,16-dimethyl-PGF$_{2\alpha}$. Likewise following the procedure of Example 24 each of the various other prostaglandin-type acids described above is transformed to the corresponding sodium, potassium, calcium, trimethylammonium, or benzyltrimethylammonium salt.

EXAMPLE 25

3-oxa-3,7-inter-m-phenylene-4,5,6-trinor-PGF$_{1\alpha}$ (Formula XC: $R_1$ is hydrogen, $R_3$ and $R_4$ of the $L_1$ moiety are hydrogen, g is one, and $R_7$ is n-butyl) or 3,7-inter-m-phenylene-4,5,6-trinor-PGF$_{1\alpha}$.

Refer to Chart G.

A. Optically Active Bicyclo[3.1.0]-hex-2-ene-6-endocarboxaldehyde.

Following the procedure of Preparation 1 of U.S. Pat. No. 3,711,515, racemic bicyclo[3.1.0]hex-2-ene-6-endo-carboxaldehyde is prepared from bicyclo[2.2.1-]hepta-2,5-diene and peracetic acid.

The racemic compound is resolved by the procedure of Example 13 of U.S. Pat. No. 3,711,515, forming an oxazolidine as follows:

Racemic bicyclo[3.1.0]hex-2-ene-6-endo-carboxaldehyde (12.3 g.) and 1-ephedrine (16.5 g.) are dissolved in about 150 ml. of benzene. The benzene is removed under vacuum and the residue taken up in about 150 ml. of isopropyl ether. The solution is filtered, then cooled to −13° C. to yield crystals of 2-endo-bicyclo-[3.1.0]hex-2-en-6-yl-3,4-dimethyl-5-phenyl-oxazolidine, 11.1 g., m.p. 90°–92° C. Three recrystallizations from isopropyl ether, cooling each time to about −2° C., yield crystals of the oxazolidine, 2.2 g., m.p. 100°–103°

C., now substantially a single isomeric form as shown by NMR.

The above re-crystallized oxazolidine (1.0 g.) is dissolved in a few ml. of dichloromethane, charged to a 20 g. silica gel column and eluted with dichloromethane. The silica gel is chromatograph-grade (Merck), 0.05–0.2 mm particle size, with about 4–5 g. of water per 100 g. Fractions of the eluate are collected, and those shown by thin layer chromatography (TLC) to contain the desired compound are combined and evaporated to an oil (360 mg.). This oil is shown by NMR to be the desired title compound, substantially free of the ephedrine, in substantially a single optically-active isomeric form. Points on the circular dichroism curve are ($\lambda$ in nm., $\theta$): 350, 0; 322.5, 4,854; 312, −5,683; 302.5, −4,854; 269, 0; 250, 2,368; 240, 0; and 210, −34,600.

B. 1-Bicyclo[3.1.0]hex-2-ene-6-endo-carboxaldehyde Neopentyl Glycol Acetal (Formula LXXXI: $R_{55}$ and $R_{56}$ taken together are $-CH_2-C(CH_3)_2-CH_2-$ and $\sim$ is endo).

A mixture of 2,2-dimethyl-1,3-propanediol (900 g.), 5 l. of benzene, and 3 ml. of 85 percent phosphoric acid is heated at reflux. To it is added, in 1.5 hours, a solution of optically active bicyclo[3.1.0]hex-2-ene-6-endo-carboxaldehyde (part A, 500 g.) in one liter of benzene. Provision is made to take off azeotropically distilled water with a Dean-Stark trap. After 3 hours the mixture is cooled and extracted with 2 liters of 5 percent sodium bicarbonate. The organic phase is dried over sodium sulfate and concentrated under reduced pressure. The resulting semisolid residue is taken up in methanol and recrystallized, using a total of 1200 ml. of methanol to which 600 ml. of water is added, then chilled to −13° C. to yield 300 g. of the title compound, m.p. 52°–55° C., and having NMR peaks at 0.66, 1.20, 0.83–2.65, 3.17–3.8, 3.96, and 5.47–5.88 $\delta$, $[\alpha]_D$ −227° (C=0.8976 in methanol), and $R_f$ 0.60 (TLC on silica gel in 25 percent ethyl acetate in mixed isomeric hexanes). Further work-up of the mother liquors yields 50–100 g. of additional product.

C. d-8-(m-Acetoxyphenyl)-7-oxa-tricyclo-[4.2.0.0$^{2,4}$]-octene-6-endo-carboxaldehyde Neopentyl Glycol Acetal (formula LXXXII: $R_{55}$ and $R_{56}$ taken together are $-CH_2-C(CH_3)_2-CH_2-$, $R_{63}$ is

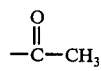

and $\sim$ is endo).

A solution of the formula LXXXI 1-bicyclo[3.1.0-]hex-2-ene-6-endo-carboxaldehyde neopentyl glycol acetate (Part B, 5.82 g.) and m-acetoxy-benzaldehyde (1.64 g.) in 25 ml. of benzene is charged to a Pyrex photolysis vessel equipped with an immersible water-cooled cold-finger and a fritted gas inlet tube. Dissolved oxygen is removed by bubbling nitrogen through the solution. The mixture is then irradiated at 350 nm. with a Rayonet Type RS Preparative Photochemical Reactor (The Southern New England Ultraviolet Co., Middletown, Conn.) equipped with siz RUL 3500 A lamps. After 24 hours the photolysate is concentrated under reduced pressure to a pale yellow oil, 10 g., which is subjected to silica gel chromatography. Elution with 10–70 percent ethyl acetate in Skellysolve B (mixture of isomeric hexanes) yields separate fractions of the recovered starting materials and the formula LXXXII title compound, a pale yellow oil, 0.86 g., having NMR peaks at 0.68, 1.20, 0.8–2.5, 2.28, 2.99, 3.12–3.88, 3.48, 4.97–5.52, and 6.78–7.60 $\delta$; infrared absorption bands at 3040, 2950, 2860, 2840, 1765, 1610, 1590, 1485, 1470, 1370, 1205, 1115, 1020, 1005, 990, 790 and 700 cm.$^{-1}$; mass spectral peaks at 358, 357, 116, 115, 108, 107, 79, 70, 69, 45, 43, and 51; $[\alpha]_D$ +55° (C=0.7505 in 95 percent ethanol); and $R_f$ 0.18 (TLC on silica gel in 25 percent ethyl acetate in mixed isomeric hexanes).

D. d-2-Exo-[m-(pivaloyloxy)benzyl]-3-exo-bicyclo[3.1.0]hexane-6-endo-carboxaldehyde Neopentyl Glycol Acetal (Formula LXXXIV: $R_{55}$ and $R_{56}$ taken together, $R_{68}$ is

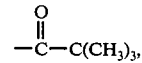

and $\sim$ is endo).

A mixture of lithium (0.25 g.) in 70 ml. of ethylamine is prepared at 0° C. and cooled to −78° C. A solution of the formula LXXXII d-8-(m-acetoxyphenyl)-7-oxa-tricyclo[4.2.0.0$^{2,4}$]-octane-6-endo-carboxaldehyde neopentyl glycol acetal (part C 1.83 g.) in 10 ml. of tetrahydrofuran is added dropwise in about 5 minutes. After stirring at −78° C. for about 3.5 hours the reaction is quenched with solid ammonium chloride and water-tetrahydrofuran. Unreacted lithium is removed, the mixture is warmed slowly to about 25° C., and ethylamine is removed. The residue is neutralized with dilute acetic acid, mixed with 200 ml. of brine, and extracted with ethyl acetate. The organic phase is washed with brine and a mixture of brine and saturated aqueous sodium bicarbonate (1:1), and dried over sodium sulfate. Concentration under reduced pressure yields the formula LXIII diol as a pale tan foamed oil, 1.64 g., having $R_f$ 0.03 (TLC on silica gel in 25 percent ethyl acetate in mixed isomeric hexanes).

The product of the preceeding paragraph is dissolved in 30 ml. of pyridine and treated with 1.5 ml. of pivaloyl chloride over a period of 22 hours at about 25° C. The reaction mixture is mixed with water, then brine and extracted with ethyl acetate. The organic phase is washed successively with brine, water, saturated aqueous copper (ll) sulfate, saturated aqueous sodium bicarbonate, and brine, and dried over sodium sulfate. Concentration under reduced pressure yields a residue, 2.53 g., which is subjected to silica gel chromatography to yield the formula LXXIV title compound, 1.87 g., having NMR peaks at 0.71, 1.20, 1.33, 0.9–3.1, 3.28–4.00, 4.17, 4.7–5.2, and 6.77–7.53 $\delta$; mass spectral peaks at 486, 485, 115, 73, 72, 57, 44, 43, 42, 41, 30, 29, 15; $[\alpha]_D$ +10° (C=0.8385 in ethanol); and $R_f$ 0.50 (TLC on silica gel in 25 percent ethyl acetate in mixed isomeric hexanes).

E. 2-Exo-[m-(pivaloyloxy)benzyl]-3-exo-(pivaloyloxy)-bicyclo[3.1.0]hexane-6-endo-carboxaldehyde (Formula LXXXV: $R_{66}$ is

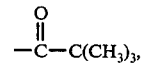

and $\sim$ is endo).

The formula LXXXIV acetal, i.e. d-2-exo-[m-(pivaloyloxy)-benzyl]-3-exo-(pivaloyloxy)-bicyclo[3.1.0]hexane-6-endo-carboxaldehyde neopentyl glycol acetal (part D, 0.48 g.) is treated at 0° C. with 25 ml. of 88 percent formic acid for 4 hours. The mixture is diluted with 200 ml. of brine and extracted with ethyl acetate. The organic phase is washed with brine and saturated aqueous sodium bicarbonate, and dried over magnesium sulfate. Concentration under reduced pressure yields an oil, 0.55 g., which is subjected to silica gel chromatography. Elution with 5–15 percent ethyl acetate in Skellysolve B yields the formula LXXXV title compound as an oil, 0.37 g., having NMR peaks at 1.20, 1.33, 0.6–3.2, 5.1–5.5, 6.6–7.5, and 9.73 $\delta$; and $R_f$ 0.50 (TLC on silica gel in 25 percent ethyl acetate in mixed isomeric hexanes).

F. 2-Exo-[m-(pivaolyloxy)benzyl]-3-exo-(pivaloyloxy)-6-endo-(cis-1-heptenyl0-bicyclo[3.1.0]hexane Formula LXXXVI: $R_3$ and $R_4$ of the $L_1$ moiety are both hydrogen, $R_7$ is n-butyl $R_{66}$ is

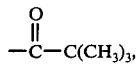

$R_{53}$ is hydrogen, and $\sim$ is endo); and 2-Exo-(m-hydroxybenzyl)-3-exo-hydroxy-6-endo-(cis-1-heptenyl)bicyclo[3.1.0]hexane (Formula LXXXVII: $R_3$ and $R_4$ of the $L_1$ moiety are both hydrogen, $R_7$ is n-butyl, $R_{53}$ and $R_{66}$ are hydrogen, and $\sim$ is endo).

A Wittig ylid reagent is prepared in 10 ml. of benzene from n-hexyltriphenylphosphonium bromide (0.79 g.) and n-butyllithium (0.6 ml. of 2.32 M. solution in hexane) at about 25° C. for 0.5 hours. After the precipitated lithium bromide has settled, the solution is removed and added to a cold (0° C.) slurry of the formula LXXXV aldehyde (part E, 0.37 g.). After 15 minutes there is added 1.0 ml. of acetone and the mixture is heated to 60° C. for 10 minutes. The mixture is concentrated under reduced pressure. The residue is washed with 10 percent ethyl acetate in Skellysolve B and these washings are concentrated to the formula LXXXVI title compound, an oil, 0.33 g. having NMR peaks at 1.18, 1.33, 0.6–3.2, 4.5–6.0, and 6.67–7.62 $\delta$ and $R_f$ 0.78 (TLC on silica gel in 25 percent ethyl acetate in Skellysolve B).

The above product of the preceeding paragraph is transformed to the formula LXXXVII diol by treatment with sodium methoxide (2.5 ml. of a 25 percent solution in methanol) for 4 hours, followed by addition of 0.5 g. of solid sodium methoxide and further stirring for 15 hours at 25° C., then at reflux for 6 hours. The mixture is cooled, mixed with 300 ml. of brine, and extracted with ethyl acetate. The organic phase is washed with brine, dried over magnesium sulfate, and concentrated under reduced pressure to a residue, 0.27 g. The residue is subjected to silica gel chromatography, eluting with 25–35 percent ethyl acetate in Skellysolve B, to yield the formula-LXXXVII title compound as an oil, 0.21 g., having NMR peaks at 0.87, 0.6–3.25, 3.88–4.35, 4.82–5.92, and 6.47–7.33 $\delta$; and $R_f$ 0.13 (TLC on silica gel in 25 percent ethyl acetate in Skellysolve B).

G. 2-Exo-{m-[(methoxycarbonyl)methoxybenzyl]}-3-exo-hydroxy-6-endo-(cis-1-heptenyl)bicyclo[3.1.0-]hexane (Formual LXXXVIII: $R_3$ and $R_4$ of the $L_1$ moiety are both hydrogen, $g$ is one, $R_7$ is n-butyl, $R_1$, $R_{53}$, and $R_{66}$ are hydrogen, and $\sim$ is endo).

The formula LXXXVII diol, i.e. 2-exo(m-hydroxybenzyl)-3-exo-hydroxy-6-endo(cis-1-heptenyl)bicyclo[3.1.0]hexane (part F, 0.19 g.) is treated in 8 ml. of dioxane with bromacetic acid (0.61 g.) and 6 ml. of 1N aqueous sodium hydroxide. After the mixture has been heated at reflux for 3 hours, with sodium hydroxide solution added when necessary to maintain a pH of about 10, the mixture is cooled, diluted with 100 ml. of water, and extracted with diethyl ether. The aqueous phase is acidified to pH 1 $\propto$ 2 and extracted with ethyl acetate to yield the formula-LXXXVII title compound, a pale yellow oil, 0.20 g. Recovered formula LXXXVII diol is obtained from the diethyl ether organic phase on drying and concentrating, 0.025 g.

H. 3-Oxa-3,7-inter-m-phenylene-4,5,6-trinor-PGF$_{1\alpha}$(-Formula XC: $R_3$ and $R_4$ of the $L_1$ moiety and $R_5$ and $R_6$ of the $M_8$ moiety are all hydrogen, $R_7$ is n-butyl, $g$ is one, and $R_1$ is hydrogen).

The formula LXXXVIII alkene is transformed to formula XC compound applying the procedure disclosed in U.S. Pat. No. 3.711,515. Thus, compound LXXXVIII (part G) is hydroxylated by the procedures of Example 6 of that patent to the formula LXXXIX glycol of Chart G, using osmium tetroxide either alone or in combination with N-methylmorpholine oxide-hydrogen peroxide complex.

The glycol is then either (1) sulfonated, for example to yield the bismesylate, and then hydrolyzed to a mixture of the title compound and its 15-epimer, applying the procedures of Example 7 of that patent, or (2) treated with substantially 100 percent formic acid to form the diformate of VIII and thereafter hydrolyzed to a mixture of the title compound and its 15-epimer, applying the procedures of Examples 20 and 21 of that patent. The epimers are separated by silica gel chromatography to yield the formula XC compound or its 15-epimer.

A third route from glycol LXXXIX to the formula XC compound is by way of a cyclic ortho ester

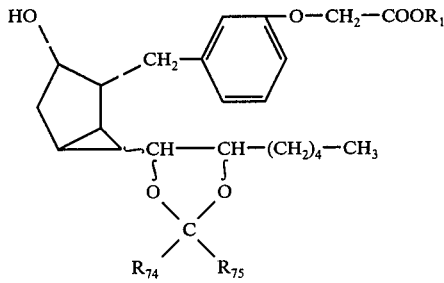

wherein $R_{74}$, $R_{75}$, and $\sim$ are as defined above. The glycol is treated as a 1–20 percent solution in benzene with trimethyl orthoformate (1.5–10 molar equivalents) and a catalytic amount (1 percent of the weight of the glycol) of pyridine hydrochloride at about 25° C. The reaction is followed by TLC (thin layer chromatography) and is complete in a few minutes. There is thus obtained the cyclic ortho ester in 100 percent yield.

The cyclic ester is then treated with 20 volumes of 100 percent formic acid at about 25° C. In about 10 minutes the reaction mixture is quenched in water or aqueous alkaline bicarbonate solution and extracted with dichloromethane. The organic phase is shaken with 5 percent aqueous sodium bicarbonate, dried over sodium sulfate, and concentrated to yield the corresponding diester. The diester is contacted with 10–50 volumes of anhydrous methanol and 10–20 percent of its weight of potassium carbonate at about 25° C. until the ester groups are removed. The mixture of epimers thusly obtained is separated by silica gel chromatography yielding the two 15-epimeric forms of the formula XC compound.

I. 2-Exo-[m-(carboxyethyl)benzyl]-3-exo-hydroxy-6-endo(cis-1-heptenyl)bicyclo[3.1.0]hexane (Formula CII: $Z_3$ is methylene, g is one, $R_3$ and $R_4$ of the $L_1$ moiety are hydrogen, $R_7$ is n-butyl, $R_1$ and $R_{53}$ are hydrogen and ~ is endo).

With respect to Chart H, there is first prepared the formula XCVII oxetane. Following the procedures of parts B and C, but replacing the m-acetoxybenzaldehyde of part B with the aldehyde of the formula

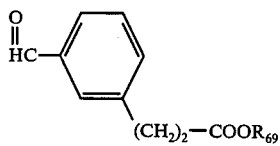

wherein $R_{69}$ is as defined above, the corresponding formula XCVII oxetanes are obtained with a fully developed side chain.

Thereafter, following the procedures of parts D, E, and F, but replacing the formula LXXXII oxetane of part D with the oxetane obtained by the procedure of the preceeding paragraph of this part, there are obtained the corresponding formula CI products.

Finally, the blocking groups on each CI compound are removed by methods disclosed herein or known in the art to yield the formula CII compound.

J. 3,7-inter-m-phenylene-4,56-trinor-$PGF_{1\alpha}$. Following the procedures of part H, the formula CII alkene is transformed in several steps to the title product.

Following the procedure of Example 25 or optionally following the procedure described in the text accompanying Charts I or J, there are prepared the various 3,7-inter-m-phenylene-3-oxa-4,5,6-trinor- or 3,7-inter-m-phenylene-4,5,6-trinor-$PGF_{1\alpha}$-type compounds described in Charts G, H, I, and J, particularly those optionally substituted at C-16 with methyl, fluoro, phenoxy, or substituted phenoxy, or at C-17 with phenyl or substituted phenyl.

EXAMPLE 26

15-Methyl-13,14-didehydro-$PGF_{2\alpha}$, methyl ester (Formula CLXXXII: $R_1$ and $R_5$ are methyl, $R_3$ and $R_4$ of the $L_1$ moiety and $R_6$ of the $M_1$ moiety are all hydrogen, $R_7$ is n-butyl, $Y_1$ is —C≡C—, $Z_1$ is cis—CH=CH—$(CH_2)_3$— and D is

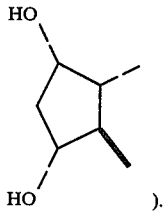

Refer to Charts L and R.

A. 15-Keto-$PGF_{2\alpha}$, methyl ester, (14.4 g.) a formula CXXXII compound, in pyridine (35 ml.) is treated with benzoyl chloride (10.5 ml.) and the reaction is allowed to continue for 2 hours. Thereafter, the resulting mixture is diluted with ice water, cooled, and diluted with ice cold 10 percent sulfuric acid and methylene chloride. The layers are then separated and the organic layer is then dried and evaporated yielding 24.18 g. of crude formula CXXXIII product ($R_{16}$ is benzoyloxy). Chromatographic purification of this crude product (15.8 g.) on silica gel (600 g.) eluting with 15 percent ethyl acetate in hexane yields 13.6 g. of pure compound.

B. The reaction product of part A (5.0 g.) in carbontetrachloride (35 ml.) is cooled to freezing and bromine (1.38 g.) is added dropwise. The reaction is then diluted with methylene chloride, washed with sodium bicarbonate, dried, and evaporated to yield 5.6 g. of a crude 13,14-dibromo product. This crude dibromo product in pyridine (25 ml.) is heated to 90°–95° C. for 1.5 hours. The mixture is then allowed to stand at room temperature for 24 hours and thereafter diluted with methylene chloride. The resulting dark solution is then partitioned with ice cold 5 percent sulfuric acid. The organic extract is washed with brine and sodium bicarbonate, dried, and evaporated to yield 5 g. of crude formula CXXXIV product. Chromatographic purification on silica gel (320 g.), eluting with 5 percent ethyl acetate in benzene, yields 2.13 g. of product.

C. A solution of the reaction product of part B (6.32 g.) in tetrahydrofuran (45 ml.) at −78° C. is treated dropwise with excess ethereal methyl magnesium bromide. The reaction proceeds for 5 minutes, and is thereafter quenched by addition of aqueous potassium bisulfate. The reaction is then diluted with diethyl ether, washed with brine, dried, and evaporated to yield 6.5 g. of crude formula CXXXV compound. The crude product is then purified on silica gel (315 g.), eluting with 7.5 percent ethyl acetate in benzene, yielding 4.28 g. of the formula CXXXV compound as a mixture of C-15 epimers.

D. A solution of the reaction product of part C above (4.28 g.) in methanol (45 ml.) is treated with potassium carbonate (1.5 g.) at ambient temperature for 72 hours. The resulting solution is thereafter concentrated under reduced pressure, diluted with 5 percent sodium chloride solution, and extracted with methylene chloride. The aqueous phase is then cooled, acidified with 0.2 molar potassium bisulfate, and thereafter extracted successively with methylene chloride in methyl acetate. The carboxylic acid containing fraction is washed with brine, dried and evaporated to yield 3.2 g. of the formula CXXXVI compound ($R_1$ is hydrogen) as an epimeric mixture. This epimeric mixture is then esterified with excess diazomethane, yielding 2.32 g. of the corresponding methyl ester. High pressure liquid chromatography of this mixture of methyl esters on silica gel (512 g.) yields 15-epi-15-methyl-14-bromo-$PGF_{2\alpha}$, methyl ester, (0.75 g.) and 15-methyl-14-bromo-$PGF_{2\alpha}$, methyl ester (0.21 g.). Additional chromatographic runs yield 0.26 g. of the (15S)-compound.

The reaction product of part A exhibits NMR absorption at 0.89, 1.3–1.5, 3.61, 5.25–5.75, 6.3, 6.8–7.25, 7.25–7.7, and 7.75–8.2 δ. Infrared absorptions are observed at 1250, 1575, 1594, 1625, 1680, and 1740.

The reaction product of part B exhibits NMR absorptions at 0.70–1.1, 1.1–3.05, 3.63, 5.25–5.8, 7.17, and 7.2–8.25 δ. The mass spectrum shows peaks at 652, 530, 451, 408, 328, 497, and 105. Characteristic infrared absorptions are observed at 1720, 1610, and 1270 cm$^{-1}$.

The (15RS) epimeric mixture produced in step 3 exhibits NMR absorptions at 0.8–1.1, 1.1–3.4, 1.48, 3.62, 3.9–5.8, 6.15, 6.06, and 7.10–8.2 δ.

For 15-methyl-14-bromo-$PGF_{2\alpha}$, methyl ester, NMR absorptions are observed at 0.7–1.1, 1.1–1.3, 1.49, 3.68, 3.85–4.4, 5.2–5.6, and 5.90 δ. The mass spectrum shows base peak absorption at 604.2587, and other peaks at 586, 571, 533, 525, 507, 347, and 217. For 15-epi-15-methyl-14-bromo-$PGF_{2\alpha}$, methyl ester, NMR absorptions are observed at 0.7–1.1, 1.1–3.4, 1.47, 3.8–4.4, 4.25–5.6, and 5.93 δ. Mass spectrum shows base peak absorption at 504.2615 and other peaks at 586, 573, 571, 533, 525, 514, 507, 496, 437, and 217.

E. A solution of the reaction product of part D, the 15-epi compound (0.19 g.) in dimethyl sulfoxide (9 ml.) is treated with 0.5 molar potassium tert-butoxide in dimethyl sulfoxide (0.9 ml.). Silver nitrate impregnated silica gel thin layer chromatography is used to monitor the progress of the reaction. After 2 hours, the reaction being complete, the reaction mixture is diluted with diethyl ether, washed with ice cold potassium bisulfate, a 5 percent sodium chloride solution, and a 5 percent sodium bicarbonate solution. Thereafter drying and evaporation of solvent yields 0.126 g. of crude (15R) title product.

The 15-epimer is prepared by the above process or is alternatively prepared by saponification of the methyl ester of the formula CXXXVI compound, dehydrohalogenation of the saponified product, and finally methyl esterification of the dehydrohalogenated product. According to this route a solution of the reaction product of part D (0.55 g.) in methanol (30 ml.) is treated with 2N sodium hydroxide (5ml.) for 18 hours. The reaction is thereafter diluted with benzene and 0.2 M potassium bisulfate solution. The organic phase is then washed with 5 percent sodium chloride solution, dried, and evaporated to yield 0.49 g. of 15-epi-15-methyl-14-bromo-PGF$_{2\alpha}$. NMR absorptions are observed at 0.7–1.1, 1.1–3.4, 3.7–4.4, 5.1–5.75, and 5.95 δ. Characteristic infrared absorptions are observed at 3300, 2600, and 1725 cm.$^{-1}$. Thereafter dehydrohalogenation proceeds by reacting the above free acid (0.49 g.) in 10 percent methanolic dimethylsulfoxide (7 ml.) with sodium methoxide (4.43 mmol) in 10 percent methanolic dimethyl sulfoxide (10.2 ml.). This mixture reacts for 20 hours. Thereafter the reaction mixture is diluted with benzene, washed with ethyl acetate and benzene (1:1). The combined organic extracts are then washed with saturated sodium chloride, dried, and evaporated to yield 0.31 g. of crude 15-epi-15-methyl-13,14-didehydro-PGF$_{2\alpha}$. This crude product is then esterified with excess diazomethane, under a nitrogen atmosphere, followed by evaporation to yield 2.8 g. of crude methyl ester. Purification on silica gel (25 g.) eluting with methylene chloride in acetone yields 0.211 g. of pure 15-epi-15-methyl-13,14-didehydro-PGF$_{2\alpha}$, methyl ester. For the free acid NMR absorptions are observed at 0.7–1.1, 1.1–3.2, 1.45, 4.0–4.5, and 5.4–6.0 δ. Characteristic absorptions are observed at 3200 to 3400, 2600 to 2700, 2220, and 1710 cm.$^{-1}$. For methyl ester NMR absorptions are observed at 0.8–1.1, 1.1–3.2, 1.46, 4.0–4.5, 5.3–5.6 δ.

Following the alternate procedure described above for the preparation of 15-epi-15-methyl-13,14-didehydro-PGF$_{2\alpha}$, methyl ester, there is prepared 15-methyl-13,14-didehydro-PGF$_{2\alpha}$, methyl ester. Accordingly, a solution of 15-methyl-14-bromo-PGF$_{2\alpha}$, methyl ester (0.41 g.) in methanol (25 ml.) is treated with 10 percent aqueous sodium hydroxide (6ml.) and the resulting reaction is allowed to proceed overnight at ambient temperature. The corresponding acid is thereafter isolated as in the procedure described above for the preparation of 15-epimer to yield 0.34 g. of crude free acid.

Without further purification 0.32 g. of the free acid obtained above in a mixture of dimethylsulfoxide in methanol (9:1; 10 ml.) is treated with 0.43 M sodium methoxide in a mixture of dimethyl sulfoxide and methanol (9:1; 6.6 ml.). After 20 hours the resulting solution is partitioned by adding ice cold 0.2 M potassium bisulfate in benzene. The aqueous phase is extracted with the mixture of benzene and ethyl acetate (1:1) and the combined extracts are washed with brine, dried, and evaporated to yield 0.180 g. of crude 15-methyl-13,14-didehydro-PGF$_{2\alpha}$. After diazomethane esterification (following the procedure described above) crude title product is prepared which is subjected to silica gel chromatography (25 g.), eluting with acetone and methylene chloride (4:1). Thereby pure 15-methyl-13,14-didehydro-PGF$_{2\alpha}$, methyl ester (0.109 g.) is obtained. NMR absorptions are observed at 0.7–1.1, 1.1–3.5, 1.46, 3.69, 4.0–4.5, and 5.3–5.7 δ. The mass spectrum shows base peak absorption at 581.3508 and other peaks at 596, 525, 506, 491, 435, 416, 345, 255, and 217. Characteristic infrared absorptions are observed at 3350, 2900, 2220, and 1740 cm$^{-1}$.

Following the procedure of Example 26, but using in place of 15-keto-PGF$_{2\alpha}$, methyl ester, each of the various 15-keto-PGF-type compounds known in the art or readily available by methods known in the art, there are prepared the corresponding 13,14-didehydro-PGF-type products. Accordingly, 3,7-inter-m-phenylene-3-oxa-4,5,6-trinor-PGF$_{1\alpha}$ is transformed to 15-keto-3,7-inter-m-phenylene-3-oxa-4,5,6-trinor-PGF$_{1\alpha}$, and this 15-keto compound is transformed following the procedure of Example 26 to 3,7-inter-m-phenylene-3-oxa-4,5,6-trinor-13,14-didehydro-PGF$_{1\alpha}$. Likewise, 3,7-inter-m-phenylene-4,5,6-trinor-PGF$_{1\alpha}$ is transformed to 3,7-inter-m-phenylene-4,5,6-trinor-13,14-didehydro-PGF$_{1\alpha}$. Further, following the procedure described in Examples 4–16 and Example 19, but omitting the 2-chlorination of Example 4, there are prepared various PGF-type compounds which are transformed, as described above to corresponding 15-keto-PGF-type compounds. Each of these 15-keto-PGF-type compounds are transformed according to the procedure of Example 26 to the corresponding 13,14-didehydro-PGF-type compound. Accordingly, each of the various 13,14-didehydro-PGFα-type compounds disclosed herein is prepared according to the procedure of Example 26, by selection of the appropriate PGF$_\alpha$-type starting material.

EXAMPLE 27

15-Methyl-13,14-didehydro-PGE$_2$, methyl ester (Formula CLXXXII: R$_1$ and R$_5$ are methyl, R$_3$ and R$_4$ of the L$_1$ moiety and R$_6$ of the M$_1$ moiety are all hydrogen, R$_7$ is n-butyl, R$_8$ is hydroxy, Y$_1$ is —C≡C—, and Z$_1$ is cis—CH=CH—(CH$_2$)$_3$—) or its 15-epimer.

Refer to Chart P and R.

A. A solution of 15-methyl-13,14-didehydro-PGF$_{2\alpha}$, methyl ester (Example 26, 0.142 g.), in acetone (18 ml.) at −45° C. is treated with trimethylsilyldiethylamine (0.6 ml.). After 2.5 hours additional reagent (2.1 ml.) is added and the reaction is continued for 5 hours. The resulting mixture is then diluted with pre-cooled diethyl ether and partitioned with aqueous sodium bicarbonate solution. The organic layer is then dried and evaporated to a yellow oil (15-methyl-13,14-didehydro-PGF$_{2\alpha}$, methyl ester, 11-(trimethylsilyl ether).

B. The oil obtained in part A is thereafter dissolved in methylene chloride (10 ml.) and thereafter added to a solution of CrO$_3$ (0.26 g.), methylene chloride (20 ml.), and pyridine (0.4 ml.) at 0° C. This oxidation mixture is then vigorously agitated at 0° C. for 5 minutes and thereafter at ambient temperature for 10 minutes. The resulting suspension is then filtered through silica gel, with the combined filtrate and methylene chloride components being thereafter evaporated to yield 0.103 g. of 15-methyl-13,14-didehydro-PGE$_2$, methyl ester, 11-trimethylsilylether (a formula CLXXiII compound).

C. Crude reaction product of part B above in methanol (20 ml.) is treated with water (10 ml.) and acetic acid (1 ml.) and reacted for 5 minutes at 0° C. and thereafter stirred for 10 minutes at ambient temperature. The reaction is then diluted with diethyl ether and partitioned with 0.2 M sodium bisulfate. The organic layer is then washed with sodium chloride and sodium bicarbonate solutions, dried, and evaporated to yield 0.082 g. of crude title product.

Following the procedure described above, the corresponding 15-epimer is obtained.

For 15-methyl-13,14-didehydro-PGE$_2$, methyl ester, the mass spectrum shows base peak absorption at 407.2981 and other peaks at 522, 491, 451, 432, 361, 307, 277, and 187. For the 15-epimer, NMR absorptions are observed at 0.8–1.1, 1.1–3.2, 1.48, 3.68, 4.1–4.7, and 5.3–5.6 δ. The mass spectrum shows base peak absorption at 507.2981, 522, 491, 451, 432, 361, 307, 277, and 187. Characteristic infrared absorptions are observed at 3300, 2257, and 1740 cm$^{-1}$.

Following the procedure of Example 27, the various 13,14-didehydro-PGF-type compounds described following Example 26 are transformed to corresponding 13,14-didehydro-PGE-type compounds.

EXAMPLE 28

15-Methyl-13,14-didehydro-PGF$_{1\alpha}$, methyl ester, or its 15-epimer.

Refer to Charts L and R.

A. A solution of 8.5 g. of PGF$_{1\alpha}$, methyl ester in dioxane (60 ml.) is treated with 2,3-dichloro-5,6-dicyano-1,4-benzoquinone (6.8 g.). The reaction proceeds for 21 hours and thereafter the suspension so formed is filtered, the filter cake being washed with dioxane and the combined filtrate and wash concentrated under reduced pressure. The residue is triturated with methylene chloride, filtered, and the solvent removed to yield 11.6 g., of crude 15-keto-PGF$_{1\alpha}$, methyl ester. Crude product is chromatographed on silica gel (450 g.), eluting with hexane and ethyl acetate (1:1). Pure compound (7.04 g.) is thereby obtained. NMR absorptions are observed at 0.89, 1.05–2.05, 2.05–2.75, 3.20–3.8, 3.67, 6.13, and 6.76 δ.

B. A solution of the reaction product of part A (7.07 g.) in pyridine (40 ml.) is treated with benzoyl chloride (6.3 ml.) and the reaction is allowed to proceed to ambient temperature for 3 hours. The resulting mixture is then diluted with ice water and extracted with methylene chloride. The methylene chloride extract is washed with solutions of ice cold dilute sulfuric acid, sodium bicarbonate, and sodium chloride. The washed extract is then dried and evaporated to yield 11.4 g. of a viscous oil. This oil is chromatographed on silica gel (200 g.) and pure product is obtained diluting with hexane in ethyl acetate (85:15). Accordingly, there is recovered pure 15-keto-9,11-dibenzoyl-PGF$_{1\alpha}$, methyl ester (10.76 g.). NMR absorptions are observed at 0.89, 1.5–1.80, 2.0–2.3, 2.3–2.7, 3.63, 5.1–5.65, 6.26, 6.92, 7.2–7.7, and 7.8–8.2 δ.

C. A solution of the reaction product of part B (4.77 g.) in carbon tetrachloride (20 ml.) is treated dropwise with a solution of bromine (8.3 mmol.) in tetrachloroethane (30 ml.). Coloration is observed to disappear in 10 minutes. The solvent is then removed under reduced pressure to yield 5.0 g. of 13,14-dibromo-9,11-dibenzoyl-15-keto-PGF$_{1\alpha}$, methyl ester. NMR absorptions are observed at 0.9, 1.10–2.0, 2.0–3.3, 3.65, 4.4–4.95, 5.08, 5.45–5.85, 7.10–7.8, and 7.9–8.2 δ.

D. The reaction product of part C (2.56 g.) in pyridine (18 ml.) is heated at 90°–95° C. for 1 hour. Thereafter the resulting dark green solution is diluted with methylene chloride, washed with ice cold 10 percent sulfuric acid, 5 percent sodium bicarbonate, and 5 percent sodium chloride solutions, dried, and evaporated. This process is then repeated for 2 additional runs and 9.0 g. of crude product is thereby recovered. Crude product is chromatographed on silica gel (210 g.), eluting with hexane and ethyl acetate (85:15). Thereby 5.5 g. of pure 14-bromo-9,11-dibenzoyl-15-keto-PGF$_{1\alpha}$, methyl ester is prepared. NMR absorptions are observed at 0.92, 1.1–2.0, 2.0–2.6, 2.6–3.1, 3.64, 5.1–5.7, 7.12, 7.2–7.7, and 7.8–8.7 δ.

E. A solution of the reaction product of part D above (0.43 g.) in tetrahydrofuran (15 ml.) is cooled to $-78°$ C. and treated with ethereal methyl magnesium bromide (1.6 ml.) in tetrahydrofuran (10 ml.). After 3.5 hours the reaction mixture thereby obtained is poured with stirring into a cold mixture of diethyl ether and saturated ammonium chloride. The combined ethereal extracts are then washed with sodium chloride, dried and evaporated to yield 0.43 g. of crude (15RS)-15-methyl-14-bromo-9,11-dibenzoyl-PGF$_{1\alpha}$, methyl ester. Chromatographing on silica gel (25 g.), eluting with benzene in acetone (97:3) yields 0.280 g. of pure product. NMR absorptions are observed 0.83, 1.0–2.0, 1.47, 2.0–3.4, 3.63, 5.0–5.8, 6.13, 7.2–7.7, and 7.8–8.2 δ.

F. A solution of the reaction product of part E above (0.28 g.) in methanol (15 ml.) is treated with potassium carbonate (0.1 g.). The solution is stirred for 24 hours, thereafter being concentrated under reduced pressure, diluted with sodium chloride solution and extracted with ethyl acetate. Thereby, 0.197 g. of crude deacylated product is obtained. This crude product (0.19 g.) is then chromatographed on silica gel (25 g.) eluting with methylene chloride in acetone (85:15). Thereby 43 mg. of 14-bromo-15-methyl-PGF$_{1\alpha}$, methyl ester, and 40 mg. of 15-epi-14-bromo-15-methyl-PGF$_{1\alpha}$, methyl ester is obtained. For the (15S) product NMR absorptions are observed at 0.88, 1.10–2.1, 1.45, 2.1–2.7, 3.67, 3.8–4.4, and 5.92 δ. Mass spectrum shows peaks at 426, 395, and 372. For the 15-epimeric product NMR absorptions are observed at 0.88, 1.10–2.1, 1.45, 2.1–2.5, 2.5–3.3, 3.67, 3.8–4.4, and 5.97 δ. The mass spectrum shows peaks at 408 and 329.

G. A solution of potassium t-butoxide (0.37 g.) in tert-butanol (15 ml.) is treated with the reaction product of part F above (0.36 g.). After 3.5 hours the reaction mixture is diluted with diethyl ether and one percent aqueous potassium bisulfate is added. The aqueous phase is extracted with diethyl ether and benzene solutions and the combined organic extracts washed with brine, dried, and evaporated to yield 0.35 g. of crude product. The crude product is then purified on silica gel eluting with 40 percent ethyl acetate in benzene. Thereby 78 mg. of 15-methyl-13,14-didehydro-PGF$_{2\alpha}$ is obtained.

Esterification of the product of the preceeding paragraph with diazomethane and thereafter chromatographing on silica gel, eluting with 12 percent acetone in methylene chloride yields 38 mg. of pure title product. The melting point is 50° C. The mass spectrum shows peaks at 598, 583, 527, 508, 469, 411, 217, and 187.

Characteristic infrared absorptions are observed at 1740 and 2220.

Following the procedure of part G above 0.362 g. of 15-epi-15-methyl-14-bromo-PGF$_{1\alpha}$, methyl ester is transformed to 30 mg. of the 15-epimeric title product. NMR absorptions are observed at 0.9, 1.45, 2.1–2.4, 3.67, and 4.0–4.4 δ. The mass spectrum shows peaks at 598, 583, 508, 493, 477, 469, 411, 217, and 187. Characteristic infrared absorptions are observed at 1740 and 2240 cm.$^{-1}$.

EXAMPLE 29

13,14-Didehydro-PGF$_{1\alpha}$, methyl ester or its 15-epimer.

A. Sodium borohydride (0.44 g.) in methanol (30 ml.) at −35° C. is treated with a solution of the reaction product of Example 28, part D (5.04 g.) and methanol. The solution is stirred for 20 minutes, quenched with acetic acid (20 ml.), diluted with diethyl ether, and ice cold 0.2 M sulfuric acid is added. The combined organic extracts are washed with sodium bicarbonate and saline solutions, dried, and evaporated. The crude residue, 14-bromo-(15RS)-9,11-dibenzoyl-PGF$_{1\alpha}$, methyl ester (5.0 g.) is used without further purification. NMR absorptions are observed at 0.7–1.0, 1.0–1.9, 1.9–2.3, 2.3–3.3, 3.63, 3.9–4.3, 5.0–5.6, 6.02, 7.2–7.7, and 7.2–8.2 δ.

B. A solution of the reaction product of part A above (5.0 g.) in methanol (35 ml.) is treated with potassium carbonate (1.5 g.) and agitated for 20 hours. The resulting suspension is then concentrated under reduced pressure, diluted with water, and extracted with ethyl acetate. Drying and evaporation of solvent yields 4.52 g. of crude epimerically mixed deacylated product. The aqueous phase above is acidified and extracted with ethyl acetate to yield 0.45 g. of the free acid of the above epimerically mixed acylated product. These acids are esterified with excess ethereal diazomethane and the combined methyl ester fractions are combined on silica gel eluting with methylene chloride and acetone (7:3) yielding 1.38 g. of 14-bromo-PGF$_{1\alpha}$, methyl ester and 1.23 g. of 15-epi-14-bromo-PGF$_{1\alpha}$, methyl ester. For the (15S) compound NMR absorptions are observed at 0.7–1.1, 1.1–2.0, 2.0–2.6, 2.6–3.5, 3.68, 3.75, 4.4, and 5.85 δ. The mass spectrum shows peaks at 414, 412, 360, 358, 351, 333, 279, and 278.

For the 15-epimeric product NMR absorptions are observed at 0.7–1.10, 1.1–2.0, 2.0–2.5, 2.5–3.5, 3.68, 3.8–4.5, and 5.88 δ. The mass spectrum shows peaks at 360, 258, 333, 279, and 278.

C. A suspension of 50 percent sodium hydride (0.7 g.) in dimethylsulfoxide (10 ml.) is treated with tert-butanol (1.3 ml.) and stirred until the resulting effervescence is ceased. A solution of the reaction product of part B above (1.38 g.) in dimethylsulfoxide (15 ml.) is added. After 20 hours the reaction is diluted with benzene and diethyl ether (1:1), and ice cold potassium bisulfate in water is added. The layers are separated and combined. The organic extracts are washed with a sodium chloride solution, dried, and evaporated. The residue is esterified with diazomethane. The resulting crude ester product (1.13 g.) is chromatographed on silica gel and the product eluted with methylene chloride in acetone (7:3). Thereby 0.61 g. of pure title product is obtained. Melting point is 68° C. NMR absorptions are observed at 0.90, 1.1–2.0, 2.0–3.0, 3.0–3.9, 3.68, and 4.0–4.45 δ. Characteristic infrared absorptions are observed at 1740, 2250, and 3200 to 3600 cm.$^{-1}$. Mass spectrum shows peaks at 322, 319, 306, 297, 295, 294, 279, 278, 276, 250, and 222.

Following the procedure of Example 29, 1.23 g. of 15-epi-14-bromo-PGF$_{1\alpha}$, methyl ester is transformed to 0.53 g. of 15-epi-13,14-didehydro-PGF$_{1\alpha}$, methyl ester. NMR absorptions are observed 0.90, 1.1–2.0, 2.0–3.4, 3.68, and 3.9–4.7 δ. Characteristic infrared absorptions are observed at 1740, 2250, and 3450. The mass spectrum shows peaks at 350, 337, 332, 319, 306, 297, 295, 294, 279, 278, 276, 250, and 222.

EXAMPLE 30

13,14-Didehydro-PGE$_1$, methyl ester or its 15-epimer.

A. A solution of 13,14-didehydro-PGF$_{1\alpha}$, methyl ester (Example 29, 0.22 g.) in acetone (18 ml.) at −45° C. is treated with trimethylsilyldiethylamine (0.8 ml.) and the resulting mixture stirred for 3.5 hours. Additional silylating agent (0.8 ml.) is added. After 45 minutes the reaction is quenched by sodium bicarbonate solution and extracted with diethyl ether. Drying and evaporation of solvent yields 0.34 g. of crude 13,14-didehydro-PGF$_{1\alpha}$, methyl ester, 11,15-bis(trimethylsilyl ether).

B. The reaction product of part A (0.6 g.) in methylene chloride (25 ml.) at 0° C. is treated with chromium trioxide (0.5 g.) methylene chloride (40 ml.) and pyridine (0.8 ml.). The oxidation conditions are then maintained (0° C.) for 5 minutes and thereafter the temperature is allowed to warm to ambient temperature for an additional 10 minutes. The resulting mixture is then diluted with methylene chloride, and filtered through silica gel. The resulting eluant is then evaporated to yield 0.41 g. of crude 13,14-didehydro-PGE$_1$, methyl ester, 11,15-bis(trimethylsilyl ether).

C. The product of part B above is combined with a mixture of methanol water and acetic acid (20:10:1, 31 ml.). The reaction is allowed to proceed at 0° C. for 5 minutes and thereafter at ambient temperature for 15 minutes. The resulting product is then diluted with water and extracted with diethyl ether. The combined ethereal extracts are then washed with sodium bicarbonate and brine and dried and evaporated to yield 0.33 g. of crude title product. This crude product is then chromatographed on 25 g. of silica gel eluting with methylene chloride in acetone (9:1) yielding 80 ml. of pure 13,14-didehydro-PGE$_1$, methyl ester. Melting point is 46° C. characteristic 0.9, 1.1–2.05, 2.05–3.4, 3.67, and 4.0–4.6 δ. The mass spectrum shows absorptions at 348, 320, 319, 295, 292, and 263. The infrared absorption spectrum shows characteristic absorptions at 1675, 1740, 2220, and 3400 cm.$^{-1}$.

Following the procedure of Example 30, parts A, B, and C, 130 mg. of 15-epi-13,14-didehydro-PGF$_{1\alpha}$, methyl ester is transformed to 26.5 mg. of 15-epi title product. Characteristic infrared absorptions are observed at 1740, 2225, and 3450 cm$^{-1}$. The mass spectrum shows peaks at 348, 320, 319, 317, 295, 292, and 263.

EXAMPLE 31

13,14-Didehydro-PGF$_{1\alpha}$ or its 15-epimer.

Potassium t-butoxide (6.79 g.) in tert-butanol (45 ml.) and methanol (8 ml.) is treated with 14-bromo-PGF$_{1\alpha}$ (3.02 g., see Example 29) and the reaction is allowed to proceed for 25 hours. The resulting reaction mixture is then diluted with diethyl ether, washed with ice cold 8 percent phosphoric acid, and the phases are separated.

The aqueous phase is then extracted with benzene, and thereafter extracted with ethyl acetate. The combined organic extracts are then washed with a sodium chloride solution, dried, and evaporated to yield 2.86 g. of title product. The melting point is 74°–75° C. The mass spectrum shows base peak absorption at 642.3961 and other peaks at 627, 571, 552, 537, 481, and 436. Characteristic NMR absorptions are observed at 3150 to 3525, 2700, 2220, 1710, and 1680.

Following the procedure of the preceding paragraph, but using as starting material 15-epi-14-bromo-PGF$_{1\alpha}$ (1.84 g.) there is prepared 15-epi-13,14-didehydro-PGF$_{1\alpha}$ (1.46 g.). The melting point is 95°–96° C. NMR absorptions are observed at 0.8–1.1, 1.1–1.9, 2.0–2.8, and 3.9–4.7 δ. The mass spectrum shows base peak absorptions at 642.4021 and other peaks at 627, 571, 552, 537, 481, and 217. The infrared absorption spectrum shows characteristic absorptions at 3150 to 3300, 2700, 2220, 1725, and 1700 cm.$^{-1}$.

EXAMPLE 32

13,14-Didehydro-16-phenoxy-17,18,19,20-tetranor-8β,12α-PGF$_2$β, methyl ester (Formula CXLVI: $R_1$ is methyl, $R_2$ and $R_3$ of the $L_1$ moiety and $R_5$ and $R_6$ of the $M_1$ moiety are hydrogen, $R_7$ is phenoxy, $Y_2$ is —C≡C—, $Z_2$ is cis—CH=CH—CH$_2$—(CH$_2$)$_3$—CH$_2$—, $R_8$ is hydroxy, and $M_{18}$ is

Refer to Chart M.

A. To a well stirred mixture of 15.2 g. of a 77 percent sodium hydride dispersion in mineral oil in 2 l. of tetrahydrofuran under a nitrogen atmosphere at 0° C. is added a solution of 92.9 g. of dimethyl-2-oxo-3-phenoxypropyl phosphate and 220 ml. of tetrahydrofuran. After stirring at 0° for 5 minutes the resulting ylide solution is then stirred at ambient temperature for 75 minutes, thereafter being cooled at 0° C. Into the ylide solution is decanted 3β-benzoyloxy-5β-hydroxy-2α-carboxaldehyde-1β-cyclopentaneacetic acid γ lactone. The resulting mixture is then stirred at ambient temperature for 24 hours. The reaction is thereafter quenched by addition of 2 l. of 2M sodium bisulfate and ice. The aqueous mixture is then extracted well with chloroform. The organic extracts are then combined, washed with water, and saturated with sodium bicarbonate and brine, dried over sodium sulfate, and evaporated to yield a dark oil. This oil is then chromatographed on 2 kg. of silica gel packed in 25 percent ethyl acetate and Skellysolve B. Eluting with 4 l. of 75 percent ethyl acetate in Skellysolve B yields 3β-benzoyloxy-5β-hydroxy-2α-(3-oxo-4-phenoxy-trans-1-butenyl)-1β-cyclopentoneacetic acid γ lactone.

B. Following the procedure of Example 4, part B, the reaction product of part A of this example is transformed to 3β-benzoyloxy-5β-hydroxy-2α-(2-chloro-3-oxo-4-phenoxytrans-1-butenyl)-1β-cyclopentaneacetic acid γ lactone.

C. To the stirred mixture of 2.3 g. of sodium borohydride in 213 ml. of methanol at −20° C. under nitrogen atmosphere is added dropwise 17.7 g. of the reaction product of part B above in 67 ml. of methanol and 200 ml. of tetrahydrofuran. After 1 hour, the resulting mixture is quenched at −20° C. by slow addition of 11 ml. of acetic acid. The resulting solution is then allowed to warm to ambient temperature and diluted with ethyl acetate and washed with 2 M sodium bisulfate, water, and thereafter saturated with sodium bicarbonate and brine, dried over sodium sulfate, and evaporated to yield an oil. This oil containing a mixture of epimers is separated employing high pressure liquid chromatography on a 250 g. column eluting with 10 percent acetone in methylene chloride at 75 pounds per square inch. Pure (15R) and (15S) epimers of 3β-benzoyloxy-5β-hydroxy-2α-(2-chloro-3-hydroxy-4-phenoxy-trans-1-butenyl)-1β-cyclopentaneacetic acid γ lactone.

D. The reaction product of part C (6.8 g.) 10.8 g. of dihydropyran and 0.7 g. of pyridine hydrochloride in 93 ml. of methylene chloride is stirred at ambient temperature for 16 hours. The resulting solution is then filtered through silica gel washing well with ethyl acetate. Evaporation of the filtrate yields 3β-benzoyloxy-5β-hydroxy-2α-(2-chloro-3α-tetrahydropyranyloxy-4-phenoxy-trans-1-butenyl)-1β-cyclopentaneacetic acid γ lactone.

E. The reaction product of part D (8.3 g.) in 167 ml. of dry methanol at ambient temperature under a nitrogen atmosphere is added to 16.7 ml. of a 25 percent solution of sodium methoxide in methanol. After 1 hour the resulting reaction mixture is quenched by addition of 10 ml. of acetic acid. The resulting solution is then evaporated cautiously under reduced pressure. The residue is then cautiously dissolved in saturated sodium bicarbonate and methyl acetate. After equilibration the aqueous phase is separated and extracted well with ethyl acetate. The organic extracts are then combined, washed with brine, dried over sodium sulfate, and evaporated to yield 3β,5β-dihydroxy-2α-(2-chloro-3α-tetrahydropyranyloxy-4-phenoxy-trans-1-butenyl)-1β-cyclopentaneacetic acid γ lactone.

F. A solution of the reaction product of step E (6.8 g.) 6.1 g. of tosyl chloride and 160 ml. of dry pyridine is stirred at 50° C. under a nitrogen atmosphere. After 4 days the resulting solution is diluted with ice and ethyl acetate. To the resulting mixture is added 1 l. of 2M sodium bisulfate in small portions with frequent equilibration. The resulting mixture is then extracted well with ethyl acetate and the organic extracts are combined, washed with water, saturated with sodium bicarbonate and brine, dried over sodium sulfate, evaporated, and azeotroped with benzene to yield 3β-tosyloxy-5β-hydroxy-2α-(2-chloro-3α-tetrahydropyranyloxy-4-phenoxy-trans-1-butenyl)-1β-cyclopentaneacetic acid γ lactone.

G. A mixture of the reaction product of part F (4.8 g.), 8.2 g. of sodium benzoate, in 194 ml. of dimethylsulfoxide is stirred under a nitrogen atmosphere at 80°–85° C. After 3 hours the resulting solution is diluted with ice and diethyl ether. After equilibration the aqueous phase is extracted well with diethyl ether. The organic extracts are then combined, washed with saturated sodium bicarbonate and brine, dried over sodium sulfate, and evaporated to yield 3α-benzoyloxy-5β-hydroxy-2α-(2-chloro-3α-hydroxy-4-phenoxy-trans-1-butenyl)-1β-cyclopentaneacetic acid γ lactone, 3-tetrahydropyranyl ether.

H. To a stirred solution of the reaction product of part G (3.8 g.) in 77 ml. of dry methanol at embient temperature under a nitrogen atmosphere is added 7.7 ml. of sodium methoxide in methanol. After 45 minutes the reaction is quenched by addition of 4.6 ml. of acetic acid. The solution is then cautiously evaporated under reduced pressure and the residue cautiously dissolved in saturated sodium bicarbonate and ethyl acetate. After equilibration the aqueous phase is separated and extracted with ethyl acetate. Organic extracts are then combined, washed with brine, dried over sodium sulfate, and evaporated to yield 3α,5β-dihydroxy-2α-(2-chloro-3'α-hydroxy-4-phenoxy-trans-1-butenyl)-1β-cyclopentaneacetic acid γ lactone, 3-tetrahydropyranyl ether.

I. A solution of the reaction product of part H (2.1 g.) 3.1 g. of dihydropyran, and 0.2 g. of pyridine hydrochloride in 30 ml. of methylene chloride is stirred at ambient temperature for 17 hours. The resulting solution is then filtered through silica gel washing well with ethyl acetate. Evaporation of the filtrate yields 3α,5β-dihydroxy-2α-(2-chloro-3α-hydroxy-4-phenoxy-trans-1-butenyl)-1β-cyclopentaneacetic acid γ lactone, bis-(tetrahydropyranyl ether).

J. The reaction product of part I is transformed to 3α,5β-dihydroxy-2α-(2-chloro-3α-hydroxy-4-phenoxy-trans-1-butenyl)-1β-cyclopentaneacetaldehyde γ lactol bis-tetrahydropyranyl ether following the procedure of Example 8, part C. Thereafter, this compound is transformed to 14-chloro-16-phenoxy-17,18,19,20-tetranor-8β,12α-PGF$_2$β, methyl ester, 11,15-bis(tetrahydropyranyl ether) following the procedure of Example 13.

K. A solution of 0.3 g. of the reaction product of part J in 20 ml. of acetic acid, water, and tetrahydrofuran (20:10:3) is heated at 40° C. for 3 hours. The resulting solution is then cooled to ambient temperature and diluted with 20 ml. of water and freeze dried to yield 14-chloro-16-phenoxy-17,18,19,20-tetranor-8β,12α-PGF$_2$β, methyl ester.

L. The reaction product of part K (0.04 g.) and dimethylsulfoxide (10 ml.) is treated with potassium tert-butoxide (40 mg.) and reacted for 28 hours at ambient temperature. The resulting solution is then diluted with diethyl ether and poured into a mixture of ice cold potassium bisulfate and diethyl ether. The resulting mixture is then diluted with benzene, partitioned, washed with a sodium chloride solution, dried, and evaporated. The residue is chromatographed and esterified with excess ethereal diazomethane. The crude methyl ester product is chromatographed on silica gel eluting with methylene chloride in acetone (75:35), yielding pure title product.

Following the procedure of Example 32, the various 8β,12α-PGF$_2$β-type compounds of Chart M are prepared. Further following the procedure of Chart M the various other PGF, PGE, or PGA-type compounds of Chart M are prepared. Further, following the procedure of Example 32, the various 11-deoxy-PGF- or PGE- compounds are prepared.

EXAMPLE 33

3,7-inter-m-Phenylene-4,5,6-trinor-13,14-didehydro-8β,12α-PGF$_{1α}$, methyl ester (Formula CLXVII: R$_1$ is methyl, Z$_1$ is M$_{18}$ is

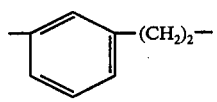

Y$_2$ is —C≡C—, R$_3$ and R$_4$ of the L$_1$ moiety and R$_5$ and R$_6$ of the M$_1$ moiety are all hydrogen, and R$_7$ is n-butyl).

Refer to Chart O.

A. Following the procedure of Example 25, the enantiomer of 3,7-inter-m-phenylene-4,5,6-trinor-15-epi-PGF$_{1α}$ is prepared from ent starting material. Thereafter, following the procedure of Examples 26 and 27 there is prepared the enantiomer of 3,7-inter-m-phenylene-4,5,6-trinor-14-chloro-15-epi-PGF$_{1α}$.

B. Thereafter, following the procedure of Example 22, there is prepared 3,7-inter-m-phenylene-4,5,6-trinor-8β,12α-PGA$_2$, a compound according to formula CLXI.

C. The reaction product of part B in 5 ml. of methanol is treated with stirring at −25° C. under nitrogen with a solution of 0.7 ml. of 30 percent aqueous hydrogen peroxide and 0.35 ml. of a 1N sodium hydroxide solution. After 1 hour there is added a 2N hydrochloric acid solution dropwise, thereby adjusting pH to 5 or 6. The resulting mixture is then diluted with brine and extracted with diethyl ether. The organic phase is washed with a sodium bicarbonate and brine, dried over sodium sulfate, and evaporated to yield 3,7-inter-m-phenylene-4,5,6-trinor-14-chloro-8β,12α-PGA$_2$, 10,11-epoxide.

D. A mixture of the reaction product of part C (0.20 g.), aluminum amalgam (0.16 g.), 8 ml. of diethyl ether, 1.6 ml. of methanol, and 4 drops of water is stirred at ambient temperature for 2 days. The resulting mixture is then filtered and the filtrate concentrated to yield the title compound as a mixture of 11α and 11β isomers. Separation by silica gel chromatography eluting with ethyl acetate in Skellysolve B yields pure 11α- product, 3,7-inter-m-phenylene-4,5,6-trinor-14-chloro-8β,12α-PGE$_2$.

The aluminum amalgam is prepared as follows:

Granular aluminum metal (50 g.) is added to a solution of mercuric chloride (50 g.) in 2 l. of water. The mixture is swirled until hydrogen gas evolution starts to become vigorous (about 30 minutes). Then most of the aqueous solution is decanted and the rest removed by rapid filtration. The amalgamated aluminum is then washed rapidly and successively with two 200 ml. portions of methanol and two 200 ml. portions of anhydrous diethyl ether. The amalgamated aluminum is then covered with anhydrous diethyl ether until ready for use.

E. Following the procedure of Example 21, the product of part D is transformed to 3,7-inter-m-phenylene-4,5,6-trinor-14-chloro-8β,12α-PGF$_{1α}$. Thereafter, following the dehydrohalogenation procedure of Example 32, there is prepared the title product.

Following the procedure of Example 33, each of the various 8β,12α-PGA-type compounds described herein is transformed to the corresponding 8β,12α-PGF or PGE-type compound.

EXAMPLE 34

17-Phenyl-18,19,20-trinor-13,14-didehydro-11-deoxy-PGE$_2$ (Formula CLVI: R$_1$ is hydrogen, R$_3$ and R$_4$ of the L$_1$ moiety and R$_5$ and R$_6$ of the M$_1$ moiety are all hydrogen, R$_7$ is benzyl, Y$_2$ is —C≡C—, and Z$_1$ is cis—CH=CH— (CH$_2$)$_3$—).

Refer to Chart N.

A. Employing 2,3-dichloro-5,6-dicyano-benzoquinone, 15-keto-17-phenyl-18,19,20-trinor-PGF$_{2α}$ is prepared from 17-phenyl-18,19,20-trinor-PGF$_{2α}$.

B. Thereafter following the procedure of Examples 26 and 27 the reaction product of part A is transformed to 13,14-didehydro-17-phenyl-18,19,20-trinor-PGE$_2$, methyl ester.

C. Following the procedure of Example 22, the reaction product of part B is transformed to 13,14-didehydro-17-phenyl-18,19,20-trinor-PGA$_2$, methyl ester.

D. To a solution of the reaction product of part C above (0.77 g.) in pyridine (5 ml.) is added acetic anhydride (1.5 ml.). The mixture is then stirred for 4 hours under nitrogen and thereafter water (50 ml.) is added. The resulting mixture is then stirred for 55 minutes and thereafter extracted with ethyl acetate. The combined organic extracts are washed, dried, and concentrated to yield a formula CLIII compound, 13,14-didehydro-17-phenyl-18,19,20-trinor-PGA$_2$, 15-acetate.

E. To a stirred solution of the reaction product of step D dissolved in methanol (25 ml.) at $-25°$ C. under a nitrogen atmosphere, a solution of sodium borohydride (2 g.) in 5 ml. of water and 20 ml. of methanol is added. This resulting mixture is then stirred at $-20°$ C. for 20 minutes and 3.5 ml. of acetic acid is thereafter cautiously added. The resulting mixture is concentrated and thereafter 50 ml. of water is added. The pH of the mixture is then adjusted to about 3 by addition of citric acid. The mixture is then extracted with dichloromethane and the combined organic extracts are washed with water and brine, dried, and concentrated to yield a formula CLIV compound.

F. To a solution of the reaction product of part E (dissolved in acetone, 50 ml.) at $-20°$ C., there is added dropwise with stirring over a one minute period the Jones reagent (1.5 ml.). This mixture is stirred at $-20°$ C. for 20 minutes and thereafter 1.5 ml. of isopropanol is added and the resulting mixture is stirred at $-20°$ C. for 10 minutes. This mixture is then diluted with 50 ml. of water and extracted with diethyl ether. The combined ethereal extracts are washed with water and brine, dried, and concentrated. The residue is then chromatographed on silica gel, eluting with acetone and methylene chloride. Those fractions containing the 15-acetate, methyl ester of the title compound are combined and concentrated.

G. To a solution of the reaction product of step F dissolved in methanol (15 ml.), there is added sodium hydroxide (0.5 g.) in 3 of water and the resulting mixture is stirred at 25° C. for 17 hours. This mixture is then acidified with 10 ml. of 3N hydrochloric acid and thereafter concentrated to an aqueous residue. The residue is diluted with 25 ml. of water and extracted with diethyl ether. The combined ethereal extracts are washed with brine, dried, and concentrated. The residue is chromatographed on acid washed silica gel, eluting with ethyl acetate and hexane. Those fractions shown to contain pure title compound compound are combined.

Following the procedure of Example 34, each of the PGF-type compounds described herein is transformed to the corresponding 13,14-didehydro-PGA-type compound, which is in turn transformed to each of the various 13,14-didehydro-11-deoxy-PG-type compounds described herein.

EXAMPLE 35

13,14-Didehydro-16,16-dimethyl-PGF$_{2\alpha}$, methyl ester.

Refer to Chart R.

A solution of the reaction product of Example 16 in dimethyl sulfoxide (10 ml.) is treated with potassium t-butoxide (40 mg.) and reacted for 28 hours at ambient temperature. The resulting solution is then diluted with diethyl ether and poured into a mixture of ice cold potassium bisulfate and diethyl ether. This mixture is then diluted with benzene partitioned, washed with a sodium chloride solution, dried, and evaporated. The residue is then esterified with excess ethereal diazomethane. The crude methyl ester is then chromatographed on silica gel (10 g.) eluting with methylene chloride and acetone (75:35). Thereby, 0.016 g. of title product is recovered. A characteristic IR absorption ($-C\equiv C-$) is observed at 2250 cm.$^{-1}$. The mass spectrum shows peaks at 327, 320, 304, 303, 302, 295, 284, 263, 247, 245, 235, 227, and 57.

Following the procedure of Example 35, each of the various 14-halo-11-deoxy-PGF$_\alpha$- or PGF$_\alpha$-type compounds described above is transformd to a corresponding 13,14-didehydro-11-deoxy-PGF$_\alpha$- or PGF$_\alpha$-type product.

Further, following the procedures of the above Examples each of the various 13,14-didehydro-11-deoxy-PGF$_\alpha$- or PGF$_\alpha$-type products is transformed to a corresponding 13,14-didehydro-11-deoxy-PGE- or PGE-type product.

Further, following the procedure of the above Examples each of the various 13,14-didehydro-11-deoxy-PGE- or PGE-type products is transformed to the corresponding 13,14-didehydro-11-deoxy-PGF$_\beta$- or 11-deoxy-PGF$_\beta$-type products.

Further, following the procedure of the above Examples each of the various 13,14-didehydro-PGE-type products is transformed to the corresponding 13,14-didehydro-PGA- or PGB-type product.

EXAMPLE 36

13,14-Didehydro-PGF$_{3\alpha}$, 13,14-didehydro-16,16-dimethyl-PGF$_{3\alpha}$, and 13,14-didehydro-16,16-difluoro-PGF$_{3\alpha}$.

A. Grignard reagents are prepared by reacting magnesium turnings with 1-bromo-cis-2-pentene; 1-bromo-1,1-dimethyl-cis-2-pentene or 1-iodo-1,1-difluoro-cis-2-pentene. 1-Iodo-1,1-difluoro-cis-2-pentene is prepared as follows:

2,2-difluoro-acetic acid is esterified with excess ethereal diazomethane. Thereafter the resulting methyl 2,2-difluoro-acetate is iodinized to methyl 2,2-difluoro-2-iodo-acetate by the procedure of Tetrahedron Lett. 3995 (1971) (e.g., addition of lithium diisopropylamine to the starting material, followed by treatment with iodine). This product is then reduced to a corresponding aldehyde 2,2-difluoro-2-iodo-acetaldehyde, employing diisobutyl aluminum hydride at $-78°$ C. This aldehyde is then alkylated by a Wittig alkylation, employing the ylid ethyl triphenylphosphorane, $(C_8H_5)_3P=CH_2-CH_3$, thereby yielding the title iodide.

B. The Grignard reagent of part A is reacted with 3$\alpha$-t-butyldimethylsilyloxy-5$\alpha$-hydroxy-2$\beta$-(2-formyl-trans-1-ethenyl)-1$\alpha$-cyclopentaneacetic acid $\gamma$ lactone, thereby preparing a corresponding 2$\beta$-[(3RS)-3-hydroxy-trans-1-cis-5-octandienyl] compound which is oxidized to a corresponding 3-oxo compound with the Collins reagent.

C. Following the procedures of the above examples the reaction product of step B is transformd to 13,14-didehyro-PGF$_{3\alpha}$.

Following the procedure of parts B and C above, but using a methyl or fluoro-substituted Grignard reagent, correspondingly 13,14-didehydro-16,16-dimethyl- PGF$_{3\alpha}$ or 13,14-didehydro-16,16-difluoro-PGF$_{3\alpha}$ is prepared.

Following the procedure of the above example, there are prepared the 11-deoxy-PGF$_\alpha$- or 11-deoxy-8$\beta$,12$\alpha$-PGF$_\alpha$-type compounds of Tables A, B, C, and D. Further, following the procedure of the above examples, there are prepared 11-deoxy-PGE- or 11-deoxy-8-,12$\alpha$-PGE-; or 11-deoxy-PGF$_\beta$- or 11-deoxy-8$\beta$,12$\alpha$-PGF$_\beta$-type compounds corresponding to each of the 11-deoxy-PGF$_\alpha$- or 11-deoxy-8$\beta$,12$\alpha$-PGF$_\alpha$-type compounds of these tables.

In interpreting these Tables, each formula listed in the Table represents a prostaglandin-type product whose complete name is given by combining the name provided in the respective legends below the formula with the prefix found in the "Name" column in the tabular section of the Tables for each example.

Table A

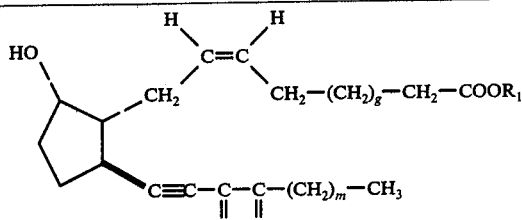

13,14-didehydro-11-deoxy-PGF$_{2\alpha}$-type compounds

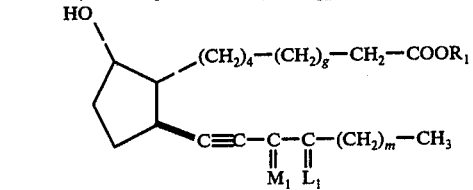

13,14-didehydro-11-deoxy-PGF$_{1\alpha}$-type compounds

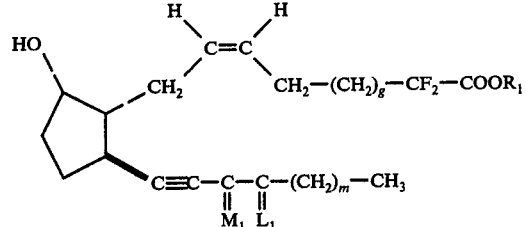

2,2-difluoro-13,14-didehydro-11-deoxy-PGF$_{2\alpha}$-type compounds

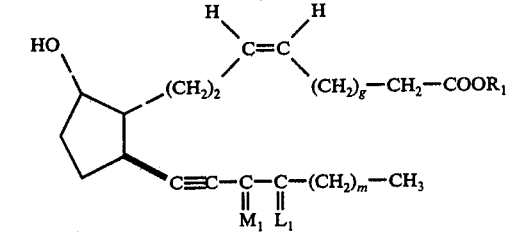

cis-4,5-didehydro-13,14-didehydro-11-deoxy-PGF$_{1\alpha}$-type compounds

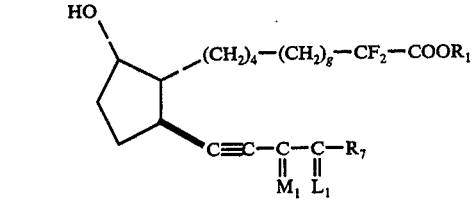

2,2-difluoro-13,14-didehydro-11-deoxy-PGF$_{1\alpha}$-type compounds

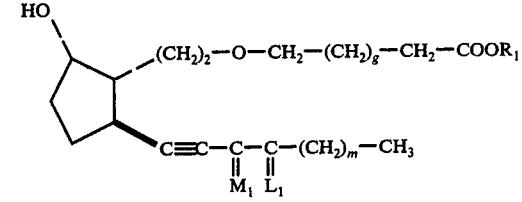

5-oxa-13,14-didehydro-11-deoxy-PGF$_{1\alpha}$-type compounds

Table A-continued

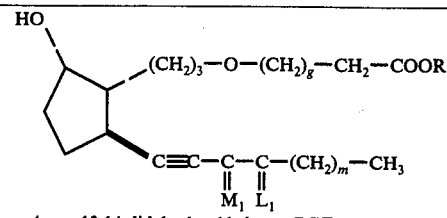
4-oxa-13,14-didehydro-11-deoxy-PGF$_{1\alpha}$-type compounds

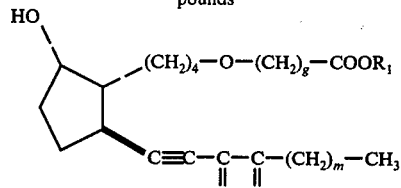
3-oxa-13,14-didehydro-11-deoxy-PGF$_{1\alpha}$-type compounds

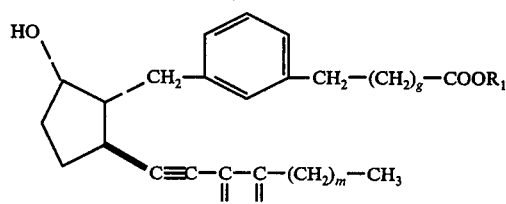
3,7-inter-m-phenylene-4,5,6-trinor-13,14-didehydro-11-deoxy-PGF$_{1\alpha}$-type compounds

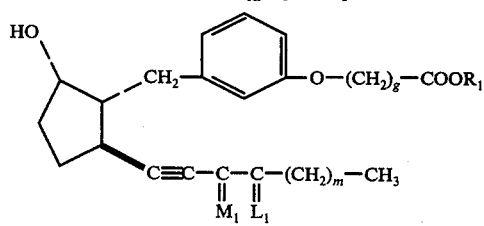
3,7-inter-m-phenylene-4,5,6-trinor-3-oxa-13,14-didehydro-11-deoxy-PGF$_{1\alpha}$-type compounds

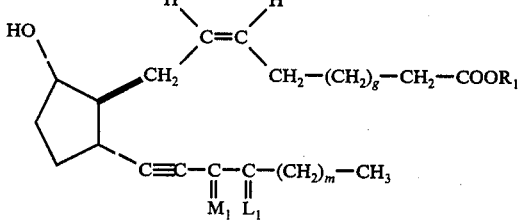
13,14-didehydro-11-deoxy-8β,12α-PGF$_{2\alpha}$-type compounds

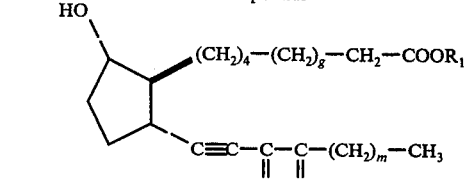
13,14-didehydro-11-deoxy-8β,12α-PGF$_{1\alpha}$-type compounds

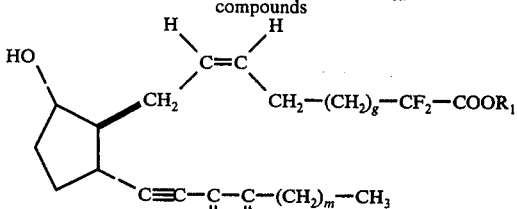
2,2-difluoro-13,14-didehydro-11-deoxy-8β,12α-

Table A-continued

PGF$_{2\alpha}$-type compounds

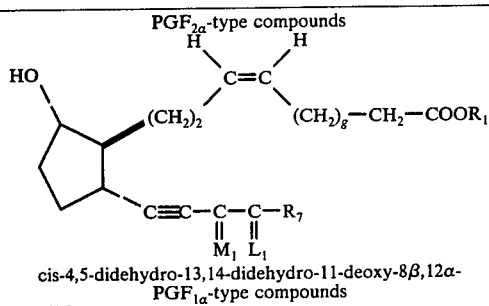
cis-4,5-didehydro-13,14-didehydro-11-deoxy-8β,12α-
PGF$_{1\alpha}$-type compounds

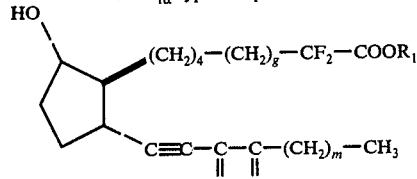
2,2-difluoro-13,14-didehydro-11-deoxy-8β,12α-
PGF$_{1\alpha}$-type compounds

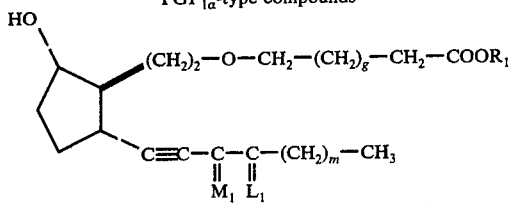
5-oxa-13,14-didehydro-11-deoxy-8β,12α-PGF$_{1\alpha}$-
type compounds

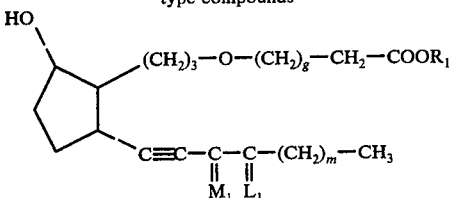
4-oxa-13,14-didehydro-11-deoxy-8β,12α-PGF$_{1\alpha}$-
type compounds

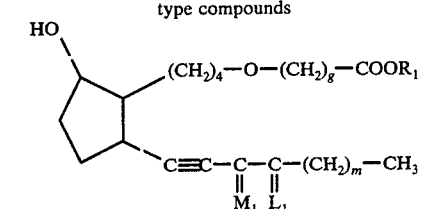
3-oxa-13,14-didehydro-11-deoxy-8β,12α-PGF$_{1\alpha}$-
type compounds

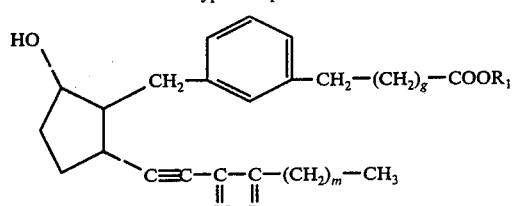
3,7-inter-m-phenylene-4,5,6-trinor-13,14-didehydro-
11-deoxy-8β,12α-PGF$_{1\alpha}$-type compounds

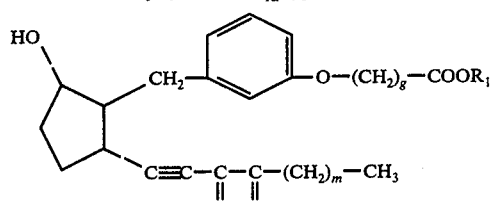
3,7-inter-m-phenylene-4,5,6-trinor-3-oxa-13,14-
didehydro-11-deoxy-8β,12α-PGF$_{1\alpha}$-type compounds Table A-continued

| Ex. | g | m | L₁ R₃ | L₁ R₄ | M₁ R₅ | M₁ R₆ | ~OR₆ | R₁ | Name |
|---|---|---|---|---|---|---|---|---|---|
| A-1 | 1 | 3 | methyl | hydrogen | hydrogen | hydrogen | α | hydrogen | 16-methyl |
| A-2 | 1 | 3 | methyl | hydrogen | methyl | hydrogen | α | hydrogen | 15,16-dimethyl |
| A-3 | 1 | 3 | methyl | hydrogen | hydrogen | methyl | α | hydrogen | 16-methyl, 15-methyl ether |
| A-4 | 1 | 3 | methyl | methyl | hydrogen | hydrogen | α | hydrogen | 16,16-dimethyl |
| A-5 | 1 | 3 | methyl | methyl | methyl | hydrogen | α | hydrogen | 15,16,16-trimethyl |
| A-6 | 1 | 3 | methyl | methyl | hydrogen | methyl | α | hydrogen | 16,16-dimethyl, 15-methyl ether |
| A-7 | 1 | 3 | fluoro | hydrogen | hydrogen | hydrogen | α | hydrogen | 16-fluoro |
| A-8 | 1 | 3 | fluoro | hydrogen | methyl | hydrogen | α | hydrogen | 15-methyl-16-fluoro |
| A-9 | 1 | 3 | fluoro | hydrogen | hydrogen | methyl | α | hydrogen | 16-fluoro, 15-methyl ether |
| A-10 | 1 | 3 | fluoro | fluoro | hydrogen | hydrogen | α | hydrogen | 16,16-difluoro |
| A-11 | 1 | 3 | fluoro | fluoro | methyl | hydrogen | α | hydrogen | 15-methyl-16,16-difluoro |
| A-12 | 1 | 3 | fluoro | fluoro | hydrogen | methyl | α | hydrogen | 16,16-difluoro, 15-methyl ether |
| A-13 | 1 | 3 | hydrogen | hydrogen | hydrogen | hydrogen | α | hydrogen | (title compound) |
| A-14 | 1 | 3 | hydrogen | hydrogen | hydrogen | methyl | α | hydrogen | 15-methyl ether |
| A-15 | 3 | 3 | hydrogen | hydrogen | hydrogen | hydrogen | α | hydrogen | 2a,2b-dihomo |
| A-16 | 3 | 3 | methyl | methyl | hydrogen | hydrogen | α | hydrogen | 2a,2b-dihomo-16,16-dimethyl |
| A-17 | 3 | 3 | methyl | methyl | methyl | hydrogen | α | hydrogen | 2a,2b-dihomo-15,16,16-trimethyl |
| A-18 | 3 | 3 | fluoro | fluoro | hydrogen | hydrogen | α | hydrogen | 2a,2b-dihomo-16,16-difluoro |
| A-19 | 3 | 3 | fluoro | fluoro | methyl | hydrogen | α | hydrogen | 2a,2b-dihomo-15-methyl-16,16-difluoro |

Table B

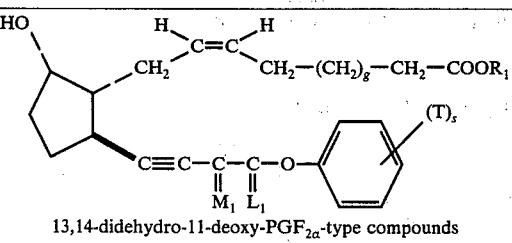

13,14-didehydro-11-deoxy-PGF$_{2\alpha}$-type compounds

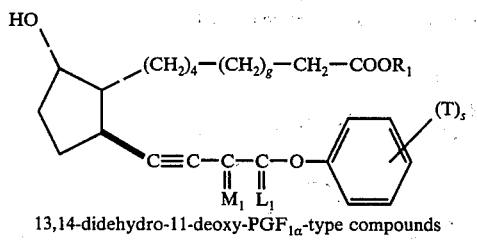

13,14-didehydro-11-deoxy-PGF$_{1\alpha}$-type compounds

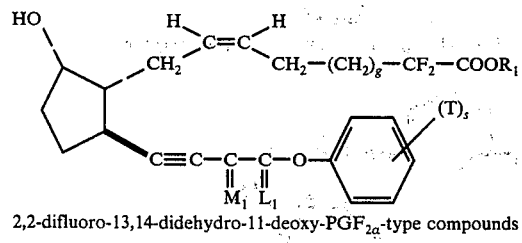

2,2-difluoro-13,14-didehydro-11-deoxy-PGF$_{2\alpha}$-type compounds

Table B-continued

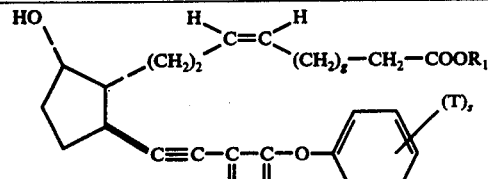
cis-4,5-didehydro-13,14-didehydro-11-deoxy-PGF$_{1\alpha}$-type compounds

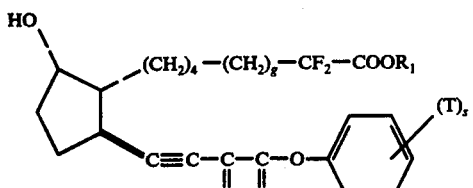
2,2-difluoro-13,14-didehydro-11-deoxy-PGF$_{1\alpha}$-type compounds

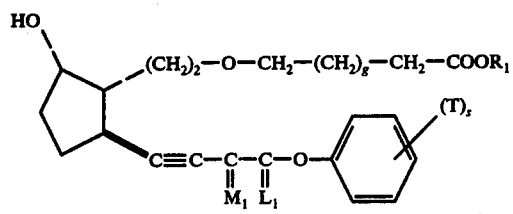
5-oxa-13,14-didehydro-11-deoxy-PGF$_{1\alpha}$-type compounds

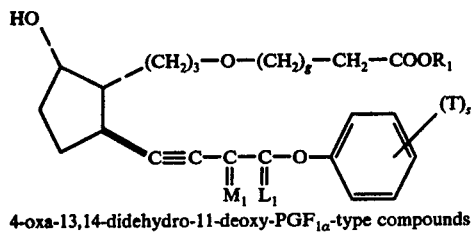
4-oxa-13,14-didehydro-11-deoxy-PGF$_{1\alpha}$-type compounds

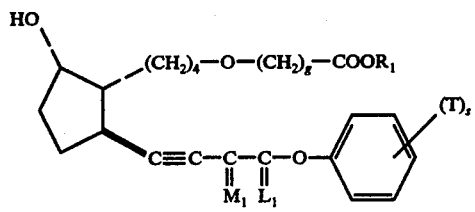
3-oxa-13,14-didehydro-11-deoxy-PGF$_{1\alpha}$-type compounds

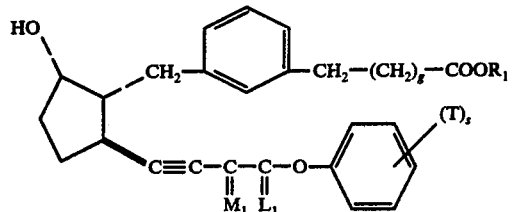
3,7-inter-m-phenylene-4,5,6-trinor-13,14-didehydro-11-deoxy-PGF$_{1\alpha}$-type compounds

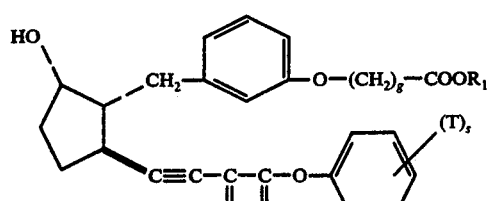
3,7-inter-m-phenylene-4,5,6-trinor-3-oxa-13,14-didehydro-11-deoxy-PGF$_{1\alpha}$-type compounds

Table B-continued

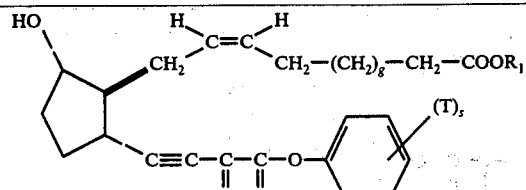

13,14-didehydro-11-deoxy-8β,12α-PGF$_{2α}$-type compounds

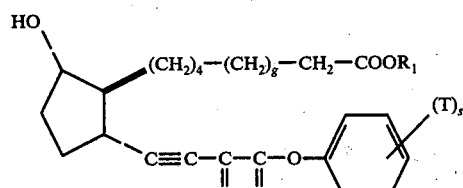

13,14-didehydro-11-deoxy-8β,12α-PGF$_{1α}$-type compounds

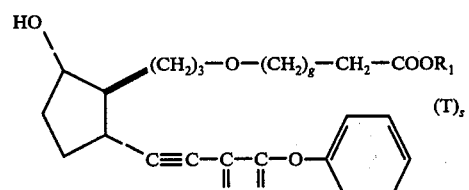

4-oxa-13,14-didehydro-11-deoxy-8β,12α-PGF$_{1α}$-type compounds

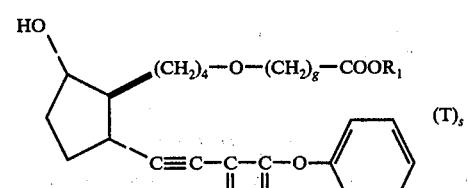

3-oxa-13,14-didehydro-11-deoxy-8β,12α-PGF$_{1α}$-type compounds

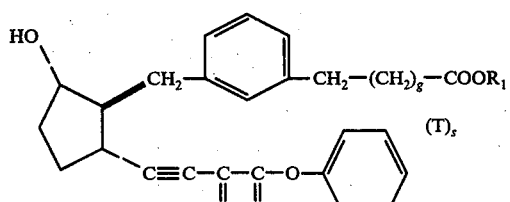

3,7-inter-m-phenylene-4,5,6-trinor-13,14-didehydro-11-deoxy-8β,12α-PGF$_{1α}$-type compounds

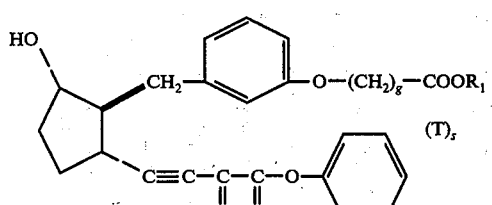

3,7-inter-m-phenylene-4,5,6-trinor-3-oxa-13,14-didehydro-11-deoxy-8β,12α-PGF$_{1α}$-type compounds

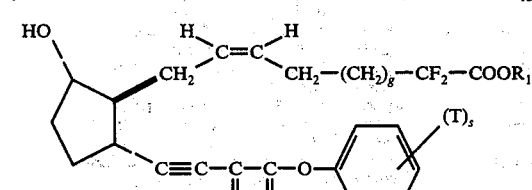

2,2-difluoro-13,14-didehydro-11-deoxy-8β,12α-PGF$_{2α}$-type compounds

Table B-continued

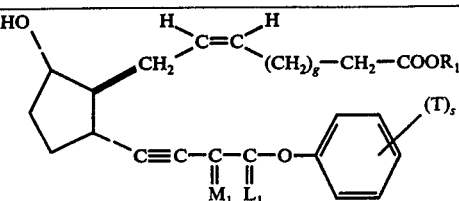

cis-4,5-dihydro-13,14-didehydro-11-deoxy-8β,12α-PGF$_{1α}$-type compounds

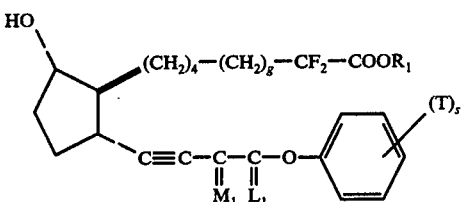

2,2-difluoro-13,14-didehydro-11-deoxy-8β,12α-PGF$_{1α}$-type compounds

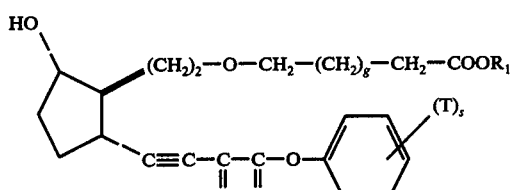

5-oxa-13,14-didehydro-11-deoxy-8β,12α-PGF$_{1α}$-type compounds

| Ex. | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| B-1 | 1 | 0 | | hydrogen | hydrogen | hydrogen | hydrogen | α | hydrogen | 16-phenoxy-17,18,19,20-tetranor |
| B-2 | 1 | 1 | p-fluoro | hydrogen | hydrogen | hydrogen | hydrogen | α | hydrogen | 16-(p-fluorophenoxy)-17,18,19,20-tetranor |
| B-3 | 1 | 1 | m-chloro | hydrogen | hydrogen | hydrogen | hydrogen | α | hydrogen | 16-(m-chlorophenoxy)-17,18,19,20-tetranor |
| B-4 | 1 | 1 | m-trifluoromethyl | hydrogen | hydrogen | hydrogen | hydrogen | α | hydrogen | 16-(m-trifluoromethylphenoxy)-17,18,19,20-tetranor |
| B-5 | 1 | 0 | | hydrogen | hydrogen | methyl | hydrogen | α | hydrogen | 15-methyl-16-phenoxy-17,18,19,20-tetranor |
| B-6 | 1 | 1 | p-fluoro | hydrogen | hydrogen | methyl | hydrogen | α | hydrogen | 15-methyl-16-(p-fluorophenoxy)-17,18,19,20-tetranor |
| B-7 | 1 | 1 | m-chloro | hydrogen | hydrogen | methyl | hydrogen | α | hydrogen | 15-methyl-16-(m-chlorophenoxy)-17,18,19,20-tetranor |
| B-8 | 1 | 1 | m-trifluoromethyl | hydrogen | hydrogen | methyl | hydrogen | α | hydrogen | 15-methyl-16-(m-trifluoromethylphenoxy) |
| B-9 | 1 | 0 | | hydrogen | hydrogen | hydrogen | methyl | α | hydrogen | 16-phenoxy-17,18,19,20-tetranor, 15-methyl ether |
| B-10 | 1 | 1 | p-fluoro | hydrogen | hydrogen | hydrogen | methyl | α | hydrogen | 16-(p-fluorophenoxy)-17,18,19,20-tetranor, 15-methyl ether |
| B-11 | 1 | 1 | m-chloro | hydrogen | hydrogen | hydrogen | methyl | α | hydrogen | 16-(m-chlorophenoxy)-17,18,19,21-tetranor, 15-methyl ether |
| B-12 | 1 | 1 | m-trifluoromethyl | hydrogen | hydrogen | hydrogen | methyl | α | hydrogen | 16-(m-trifluoromethylphenoxy)-17,18,19,20-tetranor, 15-methyl ether |
| B-13 | 1 | 0 | | methyl | methyl | hydrogen | hydrogen | α | hydrogen | 16-methyl-16-phenoxy-18,19,20-trinor |
| B-14 | 1 | 1 | p-fluoro | methyl | methyl | hydrogen | hydrogen | α | hydrogen | 16-methyl-16-(p-fluorophenoxy)-18,19,20-trinor |
| B-15 | 1 | 1 | m-chloro | methyl | methyl | hydrogen | hydrogen | α | hydrogen | 16-methyl-16-(m-chlorophenoxy)-18,19,20-trinor |
| B-16 | 1 | 1 | m-trifluoromethyl | methyl | methyl | hydrogen | hydrogen | α | hydrogen | 16-methyl-16-(m-trifluoromethylphenoxy)-18,19,20-trinor |
| B-17 | 1 | 0 | | methyl | methyl | methyl | hydrogen | α | hydrogen | 15,16-dimethyl-16-phenoxy-18,19,20-trinor |
| B-18 | 1 | 1 | p-fluoro | methyl | methyl | methyl | hydrogen | α | hydrogen | 15,16-dimethyl-16-(p-fluorophenoxy)-18,19,20-trinor |
| B-19 | 1 | 1 | m-chloro | methyl | methyl | methyl | hydrogen | α | hydrogen | 15,16-dimethyl-16-(m-chlorophenoxy)-18,19,20-trinor |
| B-20 | 1 | 1 | m-trifluoromethyl | methyl | methyl | methyl | hydrogen | α | hydrogen | 15,16-dimethyl-16-(m-trifluoromethylphenoxy)-18,19,20-trinor |
| B-21 | 1 | 0 | | methyl | methyl | hydrogen | methyl | α | hydrogen | 16-methyl-16-phenoxy-18,19,20-trinor, 15-methyl ether |
| B-22 | 1 | 1 | p-fluoro | methyl | methyl | hydrogen | methyl | α | hydrogen | 16-methyl-16-(p-fluorophenoxy)-18,19,20-trinor, 15-methyl ether |
| B-23 | 1 | 1 | m-chloro | methyl | methyl | hydrogen | methyl | α | hydrogen | 16-methyl-16-(m-chlorophenoxy)-18,19,20-trinor, 15-methyl ether |

Table B-continued

| | | | | | | | | | | |
|---|---|---|---|---|---|---|---|---|---|---|
| B-24 | 1 | 1 | m-tri-fluoro-methyl | methyl | methyl | hydrogen | methyl | α | hydrogen | 16-methyl-16-(m-trifluoromethyl-phenoxy)-18,19,20-trinor, 15-methyl ether |
| B-25 | 3 | 0 | | hydrogen | hydrogen | hydrogen | hydrogen | α | hydrogen | 2a,2b-dihomo-16-phenoxy-17,18,19,20-tetranor |
| B-26 | 3 | 1 | p-fluoro | hydrogen | hydrogen | hydrogen | hydrogen | α | hydrogen | 2a,2b-dihomo-16-(p-fluorophenoxy)-17,18,19,20-tetranor |
| B-27 | 3 | 1 | m-chloro | hydrogen | hydrogen | hydrogen | hydrogen | α | hydrogen | 2a,2b-dihomo-16-(m-chlorophenoxy)-17,18,19,20-tetranor |
| B-28 | 3 | 1 | m-tri-fluoro-methyl | hydrogen | hydrogen | hydrogen | hydrogen | α | hydrogen | 2a,2b-dihomo-16-(m-trifluoromethylphenoxy)-17,18,19,20-tetranor |
| B-29 | 3 | 0 | | hydrogen | hydrogen | methyl | hydrogen | α | hydrogen | 2a,2b-dihomo-15-methyl-16-phenoxy-17,18,19,20-tetranor |
| B-30 | 3 | 1 | p-fluoro | hydrogen | hydrogen | methyl | hydrogen | α | hydrogen | 2a,2b-dihomo-15-methyl-16-)p-fluorophenoxy)-17,18,19,20-tetranor |
| B-31 | 3 | 1 | m-chloro | hydrogen | hydrogen | methyl | hydrogen | α | hydrogen | 2a,2b-dihomo-15-methyl-16-(m-chlorophenoxy)-17,18,19,20-tetranor |
| B-32 | 3 | 1 | m-tri-fluoro-methyl | hydrogen | hydrogen | methyl | hydrogen | α | hydrogen | 2a,2b-dihomo-15-methyl-16-(m-trifluoromethylphenoxy)-17,18,19,20-tetranor |

Table C

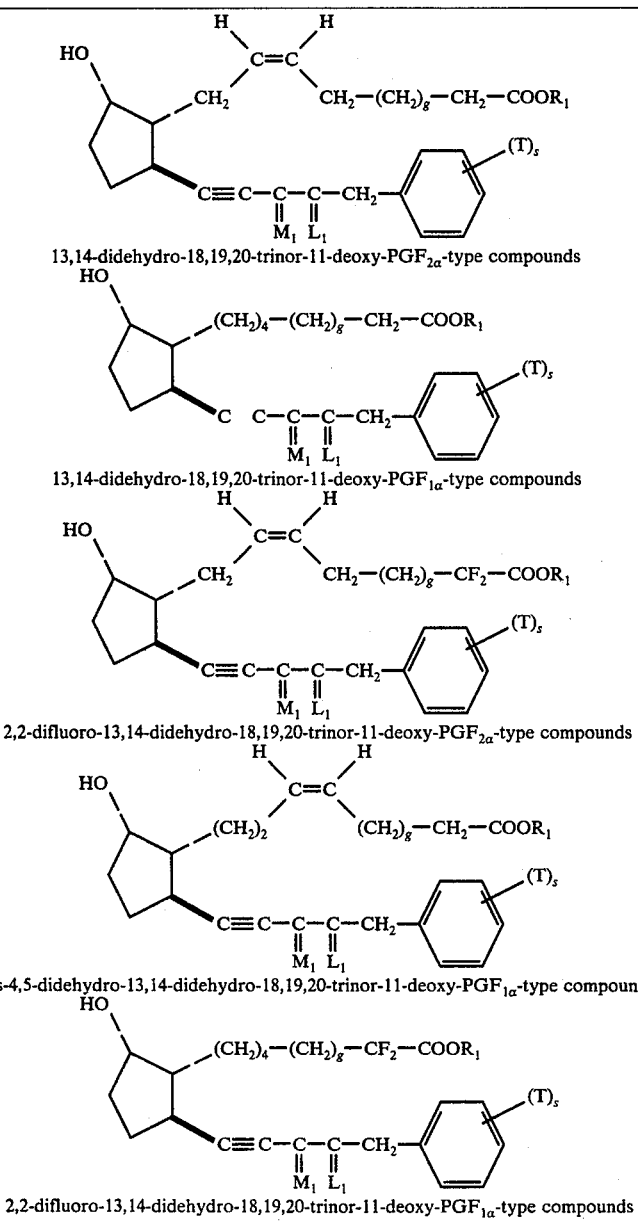

13,14-didehydro-18,19,20-trinor-11-deoxy-PGF$_{2\alpha}$-type compounds 13,14-didehydro-18,19,20-trinor-11-deoxy-PGF$_{1\alpha}$-type compounds 2,2-difluoro-13,14-didehydro-18,19,20-trinor-11-deoxy-PGF$_{2\alpha}$-type compounds cis-4,5-didehydro-13,14-didehydro-18,19,20-trinor-11-deoxy-PGF$_{1\alpha}$-type compounds 2,2-difluoro-13,14-didehydro-18,19,20-trinor-11-deoxy-PGF$_{1\alpha}$-type compounds Table C-continued

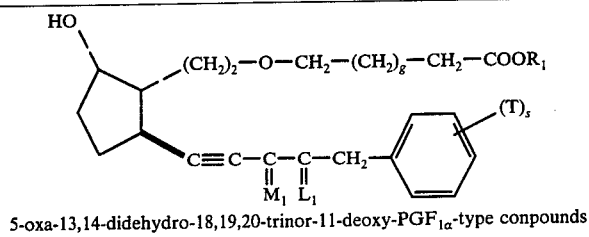

5-oxa-13,14-didehydro-18,19,20-trinor-11-deoxy-PGF$_{1\alpha}$-type conpounds

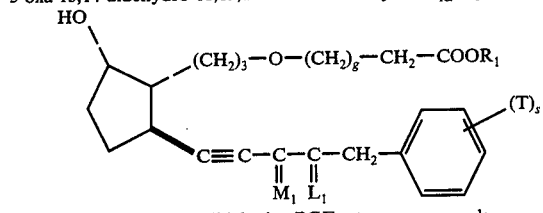

4-oxa-13,14-didehydro-PGF$_{1\alpha}$-type compounds

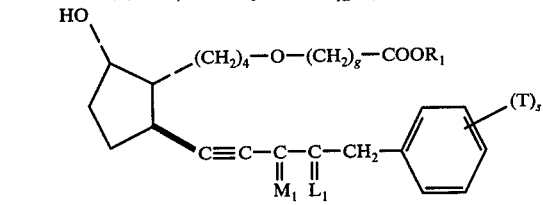

3-oxa-13,14-didehydro-18,19,20-trinor-11-deoxy-
PGF$_{1\alpha}$-type compounds

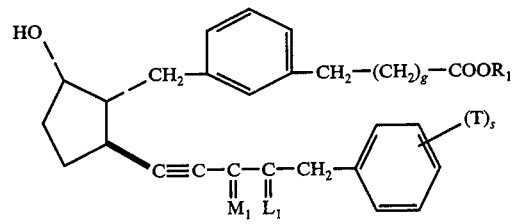

3,7-inter-m-phenylene-4,5,6-trinor-13,14-didehy-
dro-18,19,20-trinor-11-deoxy-PGF$_{1\alpha}$-type compounds

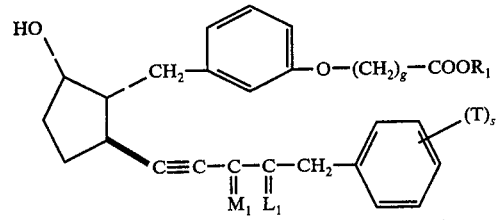

3,7-inter-m-phenylene-4,5,6-trinor-3-oxa-13,14-di-
dehydro-18,19,20-trinor-11-deoxy-PGF$_{1\alpha}$-type compounds

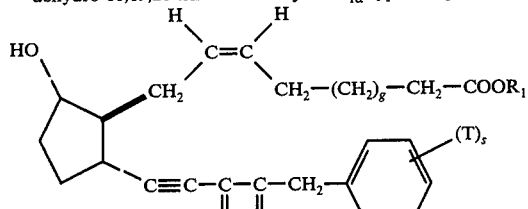

13,14-didehydro-18,19,20-trinor-11-deoxy-8β,12α-
PGF$_{2\alpha}$-type compounds

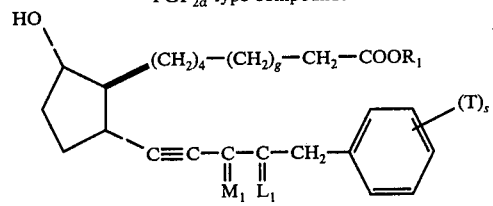

13,14-didehydro-18,19,20-trinor-11-deoxy-8β,12α-
PGF$_{1\alpha}$-type compounds

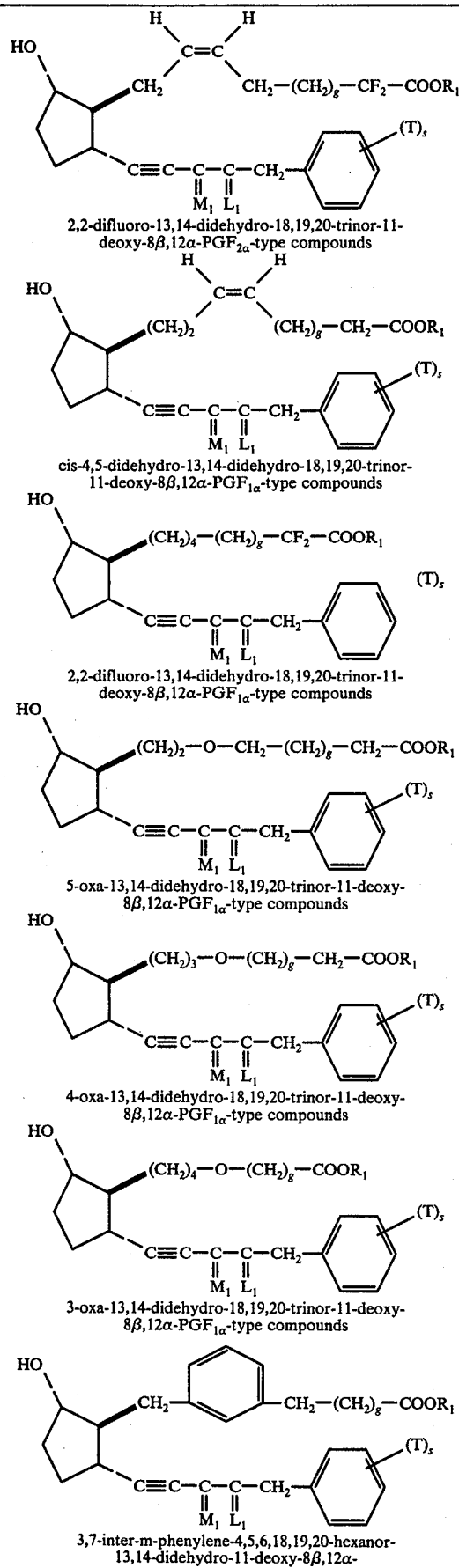

2,2-difluoro-13,14-didehydro-18,19,20-trinor-11-deoxy-8β,12α-$PGF_{2\alpha}$-type compounds cis-4,5-didehydro-13,14-didehydro-18,19,20-trinor-11-deoxy-8β,12α-$PGF_{1\alpha}$-type compounds 2,2-difluoro-13,14-didehydro-18,19,20-trinor-11-deoxy-8β,12α-$PGF_{1\alpha}$-type compounds 5-oxa-13,14-didehydro-18,19,20-trinor-11-deoxy-8β,12α-$PGF_{1\alpha}$-type compounds 4-oxa-13,14-didehydro-18,19,20-trinor-11-deoxy-8β,12α-$PGF_{1\alpha}$-type compounds 3-oxa-13,14-didehydro-18,19,20-trinor-11-deoxy-8β,12α-$PGF_{1\alpha}$-type compounds 3,7-inter-m-phenylene-4,5,6,18,19,20-hexanor-13,14-didehydro-11-deoxy-8β,12α-

Table C-continued

PGF$_{1\alpha}$-type compounds

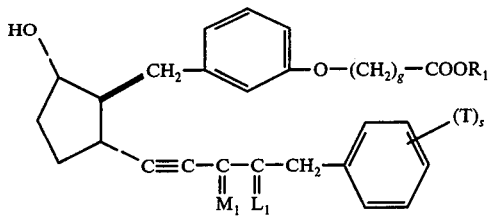

3,7-inter-m-phenylene-4,5,6,18,19,20-hexanor-3-oxa-
13,14-didehydro-11-deoxy-8β,12α-PGF$_{1\alpha}$-type compounds

| Ex. | g | s | T | L$_1$ R$_3$ | R$_4$ | M$_1$ R$_5$ | R$_6$ | ~OR$_6$ | R$_1$ | Name |
|---|---|---|---|---|---|---|---|---|---|---|
| C-1 | 1 | 0 | | hydrogen | hydrogen | hydrogen | hydrogen | α | hydrogen | 17-phenyl |
| C-2 | 1 | 1 | p-fluoro | hydrogen | hydrogen | hydrogen | hydrogen | α | hydrogen | 17-(p-fluorophenyl) |
| C-3 | 1 | 1 | m-chloro | hydrogen | hydrogen | hydrogen | hydrogen | α | hydrogen | 17-(m-chlorophenyl) |
| C-4 | 1 | 1 | m-trifluoromethyl | hydrogen | hydrogen | hydrogen | hydrogen | α | hydrogen | 17-(m-trifluoromethylphenyl) |
| C-5 | 1 | 0 | | hydrogen | hydrogen | methyl | hydrogen | α | hydrogen | 15-methyl-17-phenyl |
| C-6 | 1 | 1 | p-fluoro | hydrogen | hydrogen | methyl | hydrogen | α | hydrogen | 15-methyl-17-(p-fluorophenyl) |
| C-7 | 1 | 1 | m-chloro | hydrogen | hydrogen | methyl | hydrogen | α | hydrogen | 15-methyl-17-(m-chlorophenyl) |
| C-8 | 1 | 1 | m-trifluoromethyl | hydrogen | hydrogen | methyl | hydrogen | α | hydrogen | 15-methyl-17-(m-trifluoromethylphenyl) |
| C-9 | 1 | 0 | | hydrogen | hydrogen | hydrogen | methyl | α | hydrogen | 17-phenyl, 15-methyl ether |
| C-10 | 1 | 1 | p-fluoro | hydrogen | hydrogen | hydrogen | methyl | α | hydrogen | 17-(p-fluorophenyl), 15-methyl ether |
| C-11 | 1 | 1 | m-chloro | hydrogen | hydrogen | hydrogen | methyl | α | hydrogen | 17-(m-chlorophenyl), 15-methyl ether |
| C-12 | 1 | 1 | m-trifluoromethyl | hydrogen | hydrogen | hydrogen | methyl | α | hydrogen | 17-(m-trifluoromethylphenyl), 15-methyl ether |
| C-13 | 1 | 0 | | methyl | methyl | hydrogen | hydrogen | α | hydrogen | 16,16-dimethyl-17-phenyl |
| C-14 | 1 | 1 | p-fluoro | methyl | methyl | hydrogen | hydrogen | α | hydrogen | 16,16-dimethyl-17-(p-fluorophenyl) |
| C-15 | 1 | 1 | m-chloro | methyl | methyl | hydrogen | hydrogen | α | hydrogen | 16,16-dimethyl-17-(m-chlorophenyl) |
| C-16 | 1 | 1 | m-trifluoromethyl | methyl | methyl | hydrogen | hydrogen | α | hydrogen | 16,16-dimethyl-17-(m-trifluoromethylphenyl) |
| C-17 | 1 | 0 | | methyl | methyl | methyl | hydrogen | α | hydrogen | 15,16,16-trimethyl-17-phenyl |
| C-18 | 1 | 1 | p-fluoro | methyl | methyl | methyl | hydrogen | α | hydrogen | 15,16,16-trimethyl-17-(p-fluorophenyl) |
| C-19 | 1 | 1 | m-chloro | methyl | methyl | methyl | hydrogen | α | hydrogen | 15,16,16-trimethyl-17-(m-chlorophenyl) |
| C-20 | 1 | 1 | m-trifluoromethyl | methyl | methyl | methyl | hydrogen | α | hydrogen | 15,16,16-trimethyl-17-(m-trifluoromethylphenyl) |
| C-21 | 1 | 0 | | methyl | methyl | hydrogen | methyl | α | hydrogen | 16,16-dimethyl-17-phenyl, 15-methyl ether |
| C-22 | 1 | 1 | p-fluoro | methyl | methyl | hydrogen | methyl | α | hydrogen | 16,16-dimethyl-17-(p-fluorophenyl), 15-methyl ether |
| C-23 | 1 | 1 | m-chloro | methyl | methyl | hydrogen | methyl | α | hydrogen | 16,16-dimethyl-17-(m-chlorophenyl), 15-methyl ether |
| C-24 | 1 | 1 | m-trifluoromethyl | methyl | methyl | hydrogen | methyl | α | hydrogen | 16,16-dimethyl-17-(m-trifluoromethylphenyl), 15-methyl ether |
| C-25 | 3 | 0 | | hydrogen | hydrogen | hydrogen | hydrogen | α | hydrogen | 2a,2b-dihomo-17-phenyl |
| C-26 | 3 | 1 | p-fluoro | hydrogen | hydrogen | hydrogen | hydrogen | α | hydrogen | 2a,2b-dihomo-17-(p-fluorophenyl) |
| C-27 | 3 | 1 | m-chloro | hydrogen | hydrogen | hydrogen | hydrogen | α | hydrogen | 2a,2b-dihomo-17-(m-chlorophenyl) |
| C-28 | 3 | 1 | m-trifluoromethyl | hydrogen | hydrogen | hydrogen | hydrogen | α | hydrogen | 2a,2b-dihomo-17-(m-trifluoromethylphenyl) |
| C-29 | 3 | 0 | | hydrogen | hydrogen | methyl | hydrogen | α | hydrogen | 2a,2b-dihomo-15-methyl-17-phenyl |
| C-30 | 3 | 1 | p-fluoro | hydrogen | hydrogen | methyl | hydrogen | α | hydrogen | 2a,2b-dihomo-15-methyl-17-(m-fluorophenyl) |
| C-31 | 3 | 1 | m-chloro | hydrogen | hydrogen | methyl | hydrogen | α | hydrogen | 2a,2b-dihomo-15-methyl-17-(m-chlorophenyl) |
| C-32 | 3 | 1 | m-trifluoromethyl | hydrogen | hydrogen | methyl | hydrogen | α | hydrogen | 2a,2b-dihomo-15-methyl-17-(m-trifluoromethylphenyl) |
| C-33 | 1 | 0 | | fluoro | fluoro | hydrogen | hydrogen | α | hydrogen | 16,16-difluoro-17-phenyl |
| C-34 | 1 | 1 | p-fluoro | fluoro | fluoro | hydrogen | hydrogen | α | hydrogen | 16,16-difluoro-17-(p-fluorophenyl) |

Table C-continued

| | | | | | | | | | |
|---|---|---|---|---|---|---|---|---|---|
| C-35 | 1 | 1 | m-chloro | fluoro | fluoro | hydrogen | hydrogen | α | hydrogen | 16,16-difluoro-17-(m-chlorophenyl) |
| C-36 | 1 | 1 | m-trifluoromethyl | fluoro | fluoro | hydrogen | hydrogen | α | hydrogen | 16,16-difluoro-17-(m-trifluoromethylphenyl) |
| C-37 | 1 | 0 | | fluoro | fluoro | methyl | hydrogen | α | hydrogen | 15-methyl-16,16-difluoro-17-phenyl |
| C-38 | 1 | 1 | p-fluoro | fluoro | fluoro | methyl | hydrogen | α | hydrogen | 15-methyl-16,16-difluoro-17-(p-fluorophenyl) |
| C-39 | 1 | 1 | m-chloro | fluoro | fluoro | methyl | hydrogen | α | hydrogen | 15-methyl-16,16-difluoro-17-(m-chlorophenyl) |
| C-40 | 1 | 1 | m-trifluoromethyl | fluoro | fluoro | methyl | hydrogen | α | hydrogen | 15-methyl-16,16-difluoro-17-(m-(trifluoromethylphenyl) |
| C-41 | 1 | 0 | | fluoro | fluoro | hydrogen | methyl | α | hydrogen | 16,16-difluoro-17-phenyl, 15-methyl ether |
| C-42 | 1 | 1 | p-fluoro | fluoro | fluoro | hydrogen | methyl | α | hydrogen | 16,16-difluoro-17-(p-fluorophenyl), 15-methyl ether |
| C-43 | 1 | 1 | m-chloro | fluoro | fluoro | hydrogen | methyl | α | hydrogen | 16,16-difluoro-17-(m-chlorophenyl), 15-methyl ether |
| C-44 | 1 | 1 | m-trifluoromethyl | fluoro | fluoro | hydrogen | methyl | α | hydrogen | 16,16-difluoro-17-(m-trifluoromethylphenyl), 15-methyl ether |

Table D

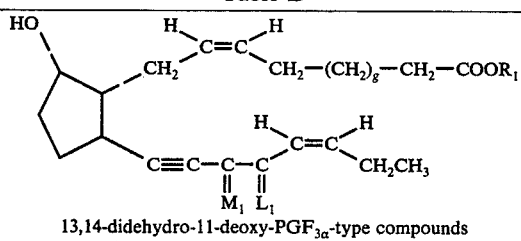

13,14-didehydro-11-deoxy-PGF$_{3\alpha}$-type compounds

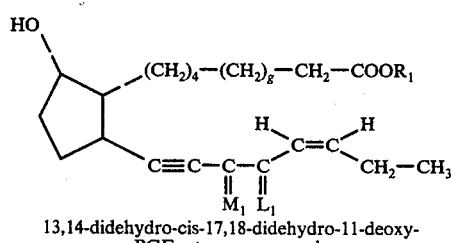

13,14-didehydro-cis-17,18-didehydro-11-deoxy-PGF$_{1\alpha}$-type compounds

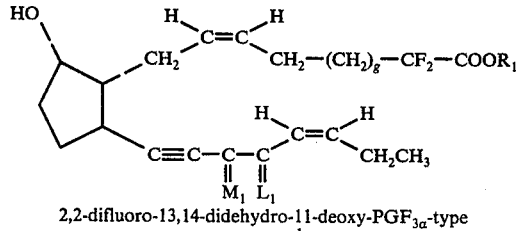

2,2-difluoro-13,14-didehydro-11-deoxy-PGF$_{3\alpha}$-type compounds

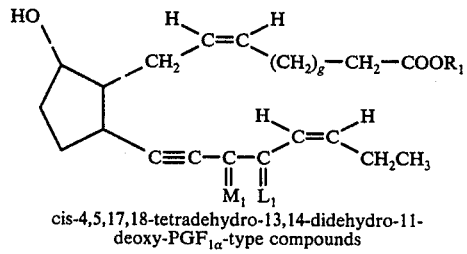

cis-4,5,17,18-tetradehydro-13,14-didehydro-11-deoxy-PGF$_{1\alpha}$-type compounds

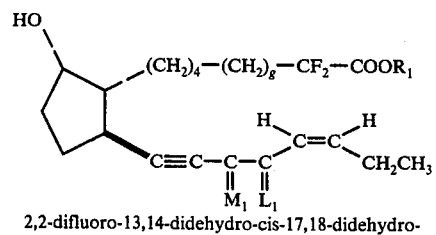

2,2-difluoro-13,14-didehydro-cis-17,18-didehydro-

Table D-continued 11-deoxy-PGF$_{1\alpha}$-type compounds

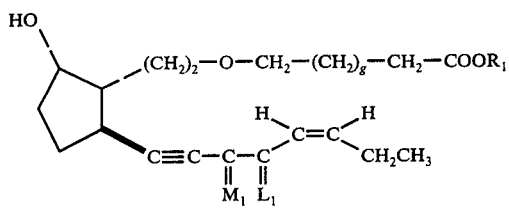

5-oxa-13,14-didehydro-cis-17,18-didehydro-11-deoxy-
PGF$_{1\alpha}$-type compounds

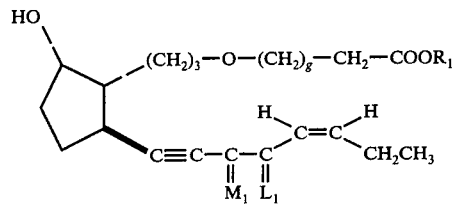

4-oxa-13,14-didehydro-cis-17,18-didehydro-11-
deoxy-PGF$_{1\alpha}$-type compounds

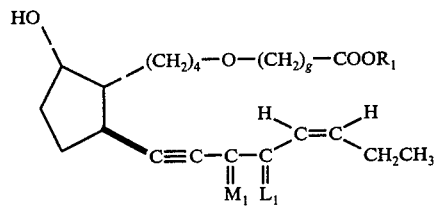

3-oxa-13,14-didehydro-cis-17,18-didehydro-11-
deoxy-PGF$_{1\alpha}$-type compounds

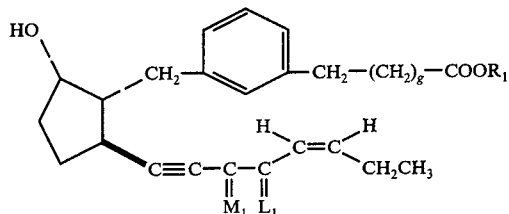

3,7-inter-m-phenylene-4,5,6-trinor-13,14-didehydro-
cis-17,18-didehydro-11-deoxy-PGF$_{1\alpha}$-type compounds

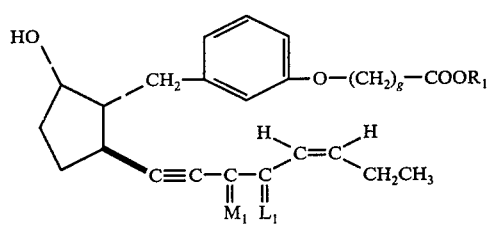

3,7-inter-m-phenylene-4,5,6-trinor-3-oxa-13,14-
didehydro-cis-17,18-didehydro-11-deoxy-PGF$_{1\alpha}$-type
compounds

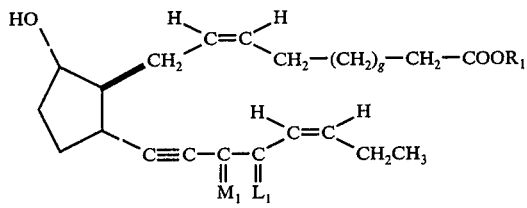

13,14-didehydro-11-deoxy-8$\beta$,12$\alpha$-PGF$_{3\alpha}$-type compounds

Table D-continued

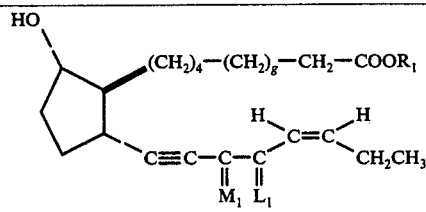

13,14-didehydro-cis-17,18-didehydro-11-deoxy-
8β,12α-PGF$_{1α}$-type compounds

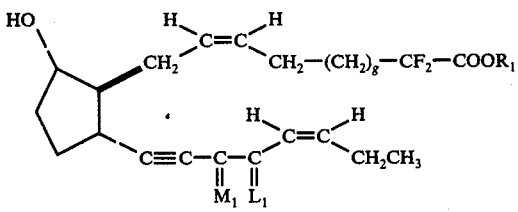

2,2-difluoro-13,14-didehydro-11-deoxy-
8β,12α-PGF$_{3α}$-type compounds

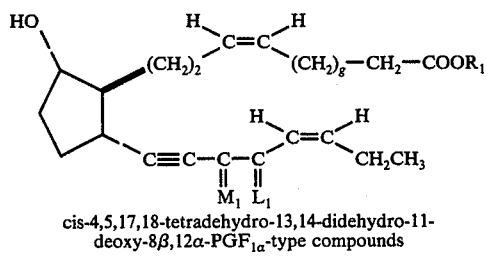

cis-4,5,17,18-tetradehydro-13,14-didehydro-11-
deoxy-8β,12α-PGF$_{1α}$-type compounds

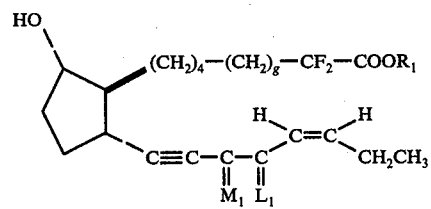

2,2-difluoro-13,14-didehydro-cis-17,18-didehydro-
11-deoxy-8β,12α-PGF$_{1α}$-type compounds

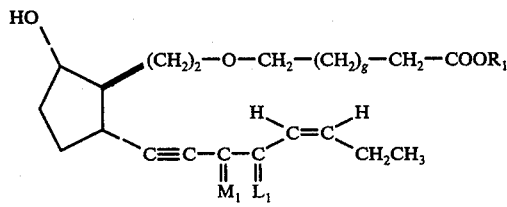

5-oxa-13,14-didehydro-cis-17,18-didehydro-11-
deoxy-8β,12α-PGF$_{1α}$-type compounds

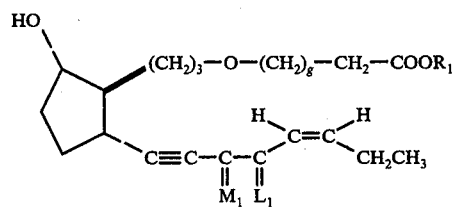

4-oxa-13,14-didehydro-cis-17,18-didehydro-11-
deoxy-8β,12α-PGF$_{1α}$-type compounds

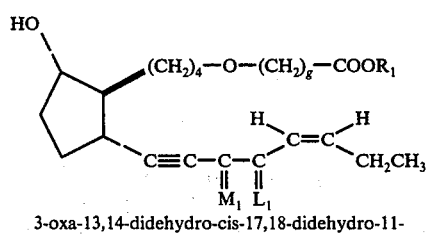

3-oxa-13,14-didehydro-cis-17,18-didehydro-11-

Table D-continued deoxy-8β,12α-PGF$_{1α}$-type compounds

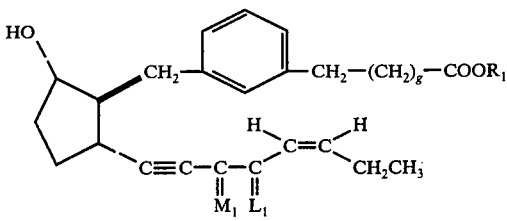

3,7-inter-m-phenylene-4,5,6-trinor-13,14-didehydro-
cis-17,18-didehydro-11-deoxy-8β,12α-PGF$_{1α}$-type compounds

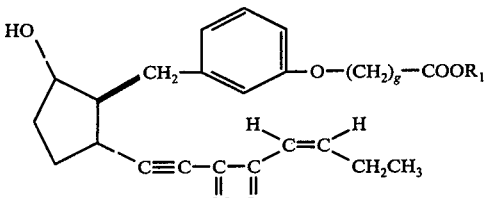

3,7-inter-m-phenylene-4,5,6-trinor-3-oxa-13,14-
didehydro-cis-17,18-didehydro-11-deoxy-8β,12α-
1α-type compounds

| Example | g | L$_1$ | | M$_1$ | | ~OR$_6$ | R$_1$ | Name |
| | | R$_3$ | R$_4$ | R$_5$ | R$_6$ | | | |
|---|---|---|---|---|---|---|---|---|
| D-1 | 1 | methyl | hydrogen | hydrogen | hydrogen | α | hydrogen | 16-methyl |
| D-2 | 1 | methyl | hydrogen | methyl | hydrogen | α | hydrogen | 15,16-methyl |
| D-3 | 1 | methyl | hydrogen | hydrogen | methyl | α | hydrogen | 16-methyl, 15-methyl ether |
| D-4 | 1 | methyl | methyl | hydrogen | hydrogen | α | hydrogen | 16,16-dimethyl |
| D-5 | 1 | methyl | methyl | methyl | hydrogen | α | hydrogen | 15,16,16-trimethyl |
| D-6 | 1 | methyl | methyl | hydrogen | methyl | α | hydrogen | 16,16-dimethyl, 15-methyl ether |
| D-7 | 1 | fluoro | hydrogen | hydrogen | hydrogen | α | hydrogen | 16-fluoro |
| D-8 | 1 | fluoro | hydrogen | methyl | hydrogen | α | hydrogen | 15-methyl-16-fluoro |
| D-9 | 1 | fluoro | hydrogen | hydrogen | methyl | α | hydrogen | 16-fluoro, 15-methyl ether |
| D-10 | 1 | fluoro | fluoro | hydrogen | hydrogen | α | hydrogen | 16,16-difluoro |
| D-11 | 1 | fluoro | fluoro | methyl | hydrogen | α | hydrogen | 15-methyl-16,16-difluoro |
| D-12 | 1 | fluoro | fluoro | hydrogen | methyl | α | hydrogen | 16,16-difluoro, 15-methyl ether |
| D-13 | 1 | hydrogen | hydrogen | hydrogen | hydrogen | α | hydrogen | title compound |
| D-14 | 1 | hydrogen | hydrogen | methyl | hydrogen | α | hydrogen | 15-methyl |
| D-15 | 3 | hydrogen | hydrogen | hydrogen | hydrogen | α | hydrogen | 2a,2b-dihomo |
| D-16 | 3 | hydrogen | hydrogen | methyl | hydrogen | α | hydrogen | 2a,2b-dihomo-15-methyl |
| D-17 | 3 | methyl | methyl | hydrogen | hydrogen | α | hydrogen | 2a,2b-dihomo-16,16-dimethyl |
| D-18 | 3 | methyl | methyl | methyl | hydrogen | α | hydrogen | 2a,2b-dihomo-15,16,16-trimethyl |
| D-19 | 3 | fluoro | fluoro | hydrogen | hydrogen | α | hydrogen | 2a,2b-dihomo-16,16-difluoro |
| D-20 | 3 | fluoro | fluoro | methyl | hydrogen | α | hydrogen | 2a,2b-dihomo-15-methyl-16,16-difluoro |

I claim:

1. A prostaglandin analog of the formula

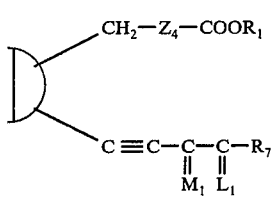

wherein D is

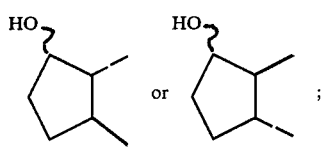

wherein Z$_4$ is
—CH$_2$—O—CH$_2$—(CH$_2$)$_g$—CH$_2$—,
—(CH$_2$)$_2$—O—(CH$_2$)$_g$—CH$_2$—, or
—(CH$_2$)$_3$—O—(CH$_2$)$_g$—; wherein g is one, 2, or 3;

wherein R$_7$ is

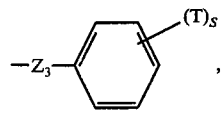

wherein Z$_3$ is oxa or methylene, s is zero, one, 2, or 3, and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl;

wherein L$_1$ is $R_3$⁀$R_4$, $R_3$⁀$R_4$, or a mixture of $R_3$⁀$R_4$ and $R_3$⁀$R_4$, wherein R$_3$ and R$_4$ are hydrogen, methyl, or fluoro, being the same or different with the proviso that one of R$_3$ and R$_4$ is methyl only when the other is hydrogen or methyl, with the further proviso that one or both of R$_3$ and R$_4$ is fluoro only when Z$_3$ is methylene; wherein M$_1$ is

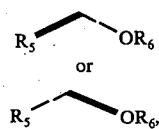

wherein R$_5$ and R$_6$ are hydrogen or methyl, with the proviso that one of R$_5$ and R$_6$ is methyl only when the other is hydrogen; and wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

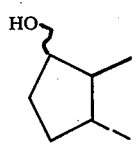

3. A compound according to claim 2, wherein M$_1$ is

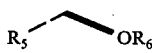

4. A compound according to claim 3, wherein g is one.

5. A compound according to claim 4, wherein R$_3$, R$_4$, R$_5$, and R$_6$ are all hydrogen.

6. 15-epi-5-Oxa-13,14-didehydro-8β,12α-11-deoxy-17-phenyl-18,19,20-trinor-PGF$_{1\alpha}$, methyl ester, a compound according to claim 4.

7. A compound according to claim 2, wherein M$_1$ is

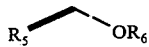

8. compound according to claim 7, wherein g is three.

9. A compound according to claim 7, wherein g is one.

10. A compound according to claim 9, wherein R$_3$ and R$_4$ are both hydrogen.

11. A compound according to claim 10, wherein R$_5$ is methyl.

12. 5-Oxa-15-methyl-13,14-didehydro-8β,12α-11-deoxy-17-phenyl-18,19,20-trinor-PGF$_{1\alpha}$, a compound according to claim 11.

13. 5-Oxa-15-methyl-13,14-didehydro-8β,12α-11-deoxy-17-phenyl-18,19,20-trinor-PGF$_{1\alpha}$, methyl ester, a compound according to claim 11.

14. A compound according to claim 10, wherein R$_6$ is methyl.

15. 5-Oxa-13,14-didehydro-8β,12α-11-deoxy-17-phenyl-18,19,20-trinor-PGF$_{1\alpha}$, 15-methyl ether, a compound according to claim 14.

16. 5-Oxa-13,14-didehydro-8β,12α-11-deoxy-17-phenyl-18,19,20-trinor-PGF$_{1\alpha}$, methyl ester, 15-methyl ether, a compound according to claim 14.

17. A compound according to claim 10, wherein R$_5$ and R$_6$ are both hydrogen.

18. 5-Oxa-13,14-didehydro-8β,12α-11-deoxy-17-phenyl-18,19,20-trinor-PGF$_{1\alpha}$, a compound according to claim 17.

19. 5-Oxa-13,14-didehydro-8β,12α-11-deoxy-17-phenyl-18,19,20-PGF$_{1\alpha}$, methyl ester, a compound according to claim 17.

20. A compound according to claim 9, wherein at least one of R$_3$ and R$_4$ is methyl.

21. A compound according to claim 9, wherein R$_3$ and R$_4$ are both methyl.

22. A compound according to claim 21, wherein R$_5$ is methyl.

23. 5-Oxa-15,16,16-trimethyl-13,14-didehydro-8β,12α-11-deoxy-17-phenyl-18,19,20-trinor-PGF$_{1\alpha}$, methyl ester, a compound according to claim 22.

24. A compound according to claim 21, wherein R$_6$ is methyl.

25. 5-Oxa-16,16-dimethyl-13,14-didehydro-8β,12α-11-deoxy-17-phenyl-18,19,20-trinor-PGF$_{1\alpha}$, methyl ester, 15-methyl ether, a compound according to claim 24.

26. A compound according to claim 21, wherein R$_5$ and R$_6$ are both hydrogen.

27. 5-Oxa-16,16-dimethyl-13,14-didehydro-8β,12α-11-deoxy-17-phenyl-18,19,20-trinor-PGF$_{1\alpha}$, a compound according to claim 26.

28. 5-Oxa-16,16-dimethyl-13,14-didehydro-8β,12α-11-deoxy-17-phenyl-18,19,20-trinor-PGF$_{1\alpha}$, methyl ester, a compound according to claim 26.

29. A compound according to claim 9, wherein at least one of R$_3$ and R$_4$ is fluoro.

30. A compound according to claim 29, wherein R$_3$ and R$_4$ are both fluoro.

31. A compound according to claim 30, wherein R$_5$ is methyl.

32. 5-Oxa-15-methyl-16,16-difluoro-13,14-didehydro-8β,12α-11-deoxy-17-phenyl-18,19,20-trinor-PGF$_{1\alpha}$, methyl ester, a compound according to claim 31.

33. A compound according to claim 30, wherein R$_6$ is methyl.

34. 5-Oxa-16,16-difluoro-13,14-didehydro-8β,12α-11-deoxy-17-phenyl-18,19,20-trinor-PGF$_{1\alpha}$, methyl ester, 15-methyl ether, a compound according to claim 33.

35. A compound according to claim 30, wherein R$_5$ and R$_6$ are both hydrogen.

36. 5-Oxa-16,16-difluoro-13,14-didehydro-8β,12α-11-deoxy-17-phenyl-18,19,20-trinor-PGF$_{1\alpha}$, a compound according to claim 35.

37. 5-Oxa-16,16-difluoro-13,14-didehydro-8β,12α-11-deoxy-17-phenyl-18,19,20-trinor-PGF$_{1\alpha}$, methyl ester, a compound according to claim 35.

38. A compound according to claim 1, wherein D is

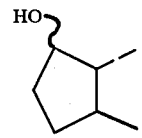

39. A compound according to claim 38, wherein M$_1$ is

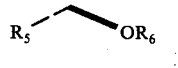

40. A compound according to claim 39, wherein g is one.

41. A compound according to claim 40, wherein $R_3$, $R_4$, $R_5$, and $R_6$ are all hydrogen.

42. 15-epi-5-Oxa-13,14-didehydro-11-deoxy-17-phenyl-18,19,20-trinor-PGF$_1\alpha$, methyl ester, a compound according to claim 41.

43. A compound according to claim 38, wherein $M_1$ is

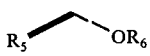

44. A compound according to claim 43, wherein g is three.

45. A compound according to claim 43, wherein g is one.

46. A compound according to claim 45, wherein $R_3$ and $R_4$ are both hydrogen.

47. A compound according to claim 46, wherein $R_5$ is methyl.

48. 5-Oxa-15-methyl-13,14-didehydro-11-deoxy-17-phenyl-18,19,20-trinor-PGF$_1\alpha$, a compound according to claim 47.

49. 5-Oxa-15-methyl-13,14-didehydro-11-deoxy-17-phenyl-18,19,20-trinor-PGF$_1\alpha$, methyl ester, a compond according to claim 47.

50. A compound according to claim 46, wherein $R_6$ is methyl.

51. 5-Oxa-13,14-didehydro-11-deoxy-17-phenyl-18,19,20-trinor-PGF$_1\alpha$, 15-methyl ether, a compound according to claim 50.

52. 5-Oxa-13,14-didehydro-11-deoxy-17-phenyl-18,19,20-trinor-PGF$_1\alpha$, methyl ester, 15-methyl ether, a compound according to claim 50.

53. A compound according to claim 46, wherein $R_5$ and $R_6$ are both hydrogen.

54. 5-Oxa-13,14-didehydro-11-deoxy-17-phenyl-18,19,20-trinor-PGF$_1\alpha$, a compound according to claim 53.

55. 5-Oxa-13,14-didehydro-11-deoxy-17-phenyl-18,19,20-trinor-PGF$_1\alpha$, methyl ester, a compound according to claim 53.

56. A compound according to claim 45, wherein at least one of $R_3$ and $R_4$ is methyl.

57. A compound according to claim 56, wherein $R_3$ and $R_4$ are both methyl.

58. A compound according to claim 57, wherein $R_5$ is methyl.

59. 5-Oxa-15,16,16-trimethyl-13,14-didehydro-11-deoxy-17-phenyl-18,19,20-trinor-PGF$_1\alpha$, methyl ester, a compound according to claim 58.

60. A compound according to claim 57, wherein $R_6$ is methyl.

61. 5-Oxa-16,16-dimethyl-13,14-didehydro-11-deoxy-17-phenyl-18,19,20-trinor-PGF$_1\alpha$, methyl ester, 15-methyl ether, a compound according to claim 60.

62. A compound according to claim 57, wherein $R_5$ and $R_6$ are both hydrogen.

63. 5-Oxa-16,16-dimethyl-13,14-didehydro-11-deoxy-17-phenyl-18,19,20-trinor-PGF$_1\alpha$, a compound according to claim 62.

64. 5-Oxa-16,16-dimethyl-13,14-didehydro-11-deoxy-17-phenyl-18,19,20-trinor-PGF$_1\alpha$, methyl ester, a compound according to claim 62.

65. A compound according to claim 45, wherein at least one of $R_3$ and $R_4$ is fluoro.

66. A compound according to claim 65, wherein $R_3$ and $R_4$ are both fluoro.

67. A compound according to claim 6, wherein $R_5$ is methyl.

68. 5-Oxa-15-methyl-16,16-difluoro-13,14-didehydro-11-deoxy-17-phenyl-18,19,20-trinor-PGF$_1\alpha$, methyl ester, a compound according to claim 67.

69. A compound according to claim 66, wherein $R_6$ is methyl.

70. 5-Oxa-16,16-difluoro-13,14-didehydro-11-deoxy-17-phenyl-18,19,20-trinor-PGF$_1\alpha$, methyl ester, 15-methyl ether, a compound according to claim 69.

71. A compound according to claim 66, wherein $R_5$ and $R_6$ are both hydrogen.

72. 5-Oxa-16,16-difluoro-13,14-didehydro-11-deoxy-17-phenyl-18,19,20-trinor-PGF$_1\alpha$, a compound according to claim 71.

73. 5-Oxa-16,16-difluoro-13,14-didehydro-11-deoxy-17-phenyl-18,19,20-trinor-PGF$_1\alpha$, methyl ester, a compound according to claim 71.

* * * * *

UNITED STATES PATENT OFFICE
CERTIFICATE OF CORRECTION

Patent No. 4,104,474              Dated  1 August 1978

Inventor(s)   Herman W. Smith

It is certified that error appears in the above-identified patent and that said Letters Patent are hereby corrected as shown below:

Columns 133-134, that portion of third through fifth formulas reading

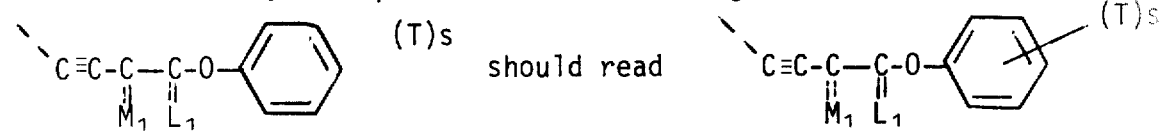

Columns 135-136, "Name" for Example B-8 reading "15-methyl-16-(m-trifluoromethylphenoxy)" should read -- 15-methyl-16-(m-trifluoromethylphenoxy)-17,18,19,20-tetranor --;

Columns 137-138, that portion of the second formula reading

Columns 141-142, that portion of the third formula reading

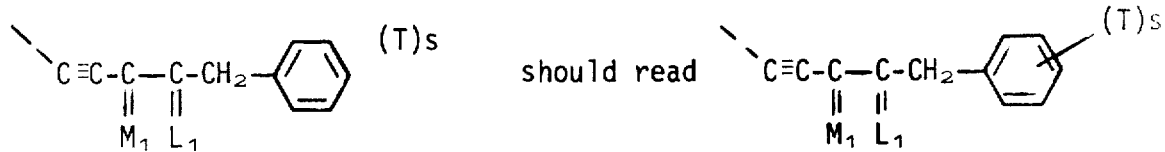

UNITED STATES PATENT OFFICE
CERTIFICATE OF CORRECTION

Patent No.  4,104,474          Dated  1 August 1978

Inventor(s)  Herman W. Smith

It is certified that error appears in the above-identified patent and that said Letters Patent are hereby corrected as shown below:

Columns 145-146, that portion of the fourth formula reading 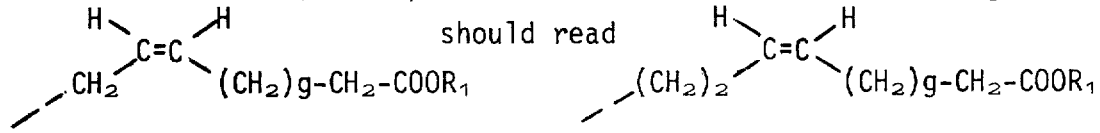

Column 156, line 27, "according to claim 6" should read -- according to claim 66 --.

Signed and Sealed this

*Eighteenth* Day of *August 1981*

[SEAL]

*Attest:*

*Attesting Officer*

GERALD J. MOSSINGHOFF

*Commissioner of Patents and Trademarks*